(12) United States Patent
Parikh

(10) Patent No.: US 8,999,915 B2
(45) Date of Patent: Apr. 7, 2015

(54) METHODS FOR ATTENUATING RELEASE OF INFLAMMATORY MEDIATORS AND PEPTIDES USEFUL THEREIN

(75) Inventor: Indu Parikh, Chapel Hill, NC (US)

(73) Assignee: Biomarck Pharmaceuticals, Ltd., Durham, NC (US)

( * ) Notice: Subject to any disclaimer, the term of this patent is extended or adjusted under 35 U.S.C. 154(b) by 970 days.

(21) Appl. No.: 12/359,892

(22) Filed: Jan. 26, 2009

(65) Prior Publication Data

US 2009/0203620 A1    Aug. 13, 2009

Related U.S. Application Data

(63) Continuation of application No. PCT/US2007/074514, filed on Jul. 26, 2007.

(60) Provisional application No. 60/833,239, filed on Jul. 26, 2006.

(51) Int. Cl.
  *A61K 38/08* (2006.01)
  *A61K 38/17* (2006.01)
  *A61K 38/10* (2006.01)

(52) U.S. Cl.
  CPC ............... *A61K 38/17* (2013.01); *A61K 38/08* (2013.01); *A61K 38/10* (2013.01)

(58) Field of Classification Search
  None
  See application file for complete search history.

(56) References Cited

U.S. PATENT DOCUMENTS

| | | | |
|---|---|---|---|
| 4,753,945 A | 6/1988 | Gilbard et al. | |
| 4,873,346 A | 10/1989 | Anderson | |
| 4,966,848 A * | 10/1990 | Smith et al. | 435/193 |
| 5,223,421 A * | 6/1993 | Smith et al. | 435/193 |
| 5,292,498 A | 3/1994 | Boucher | |
| 5,298,506 A | 3/1994 | Stamler et al. | |
| 5,436,243 A | 7/1995 | Sachs et al. | |
| 5,837,218 A * | 11/1998 | Peers et al. | 424/1.69 |
| 5,849,706 A | 12/1998 | Molina et al. | |
| 5,849,719 A | 12/1998 | Carson et al. | |
| 5,858,784 A | 1/1999 | Debs et al. | |
| 5,858,981 A | 1/1999 | Schreiber et al. | |
| 5,861,502 A | 1/1999 | Prockop et al. | |
| 6,245,320 B1 | 6/2001 | Kim | |
| 6,407,058 B1 | 6/2002 | Staddon et al. | |
| 6,506,779 B1 | 1/2003 | Cheng et al. | |
| 7,265,088 B1 | 9/2007 | Li et al. | |
| 7,524,926 B2 | 4/2009 | Parikh | |
| 7,544,772 B2 | 6/2009 | Takashi et al. | |
| 7,919,469 B2 | 4/2011 | Li et al. | |
| 8,293,870 B2 | 10/2012 | Parikh | |
| 8,492,518 B2 | 7/2013 | Parikh | |
| 8,501,911 B2 | 8/2013 | Li et al. | |
| 8,563,689 B1 | 10/2013 | Takashi et al. | |
| 2001/0033827 A1 | 10/2001 | Kim | |
| 2003/0013652 A1 | 1/2003 | Martin et al. | |
| 2003/0125249 A1 | 7/2003 | Blecha et al. | |
| 2004/0180836 A1 | 9/2004 | Martin et al. | |
| 2006/0040301 A1 | 2/2006 | Deirmengian | |
| 2006/0153834 A1 | 7/2006 | Carbonell et al. | |
| 2006/0205664 A1 | 9/2006 | Parikh | |
| 2006/0217307 A1 | 9/2006 | Takashi et al. | |
| 2008/0020031 A1 | 1/2008 | Li et al. | |
| 2009/0220581 A1 | 9/2009 | Li et al. | |
| 2009/0275520 A1 | 11/2009 | Parikh | |
| 2010/0197607 A1 | 8/2010 | Parikh | |
| 2013/0338085 A1 | 12/2013 | Parikh | |

FOREIGN PATENT DOCUMENTS

| | | |
|---|---|---|
| AU | 766800 | 10/2003 |
| CA | 2287501 A1 | 10/1998 |
| EP | 0 551 200 A1 | 7/1993 |
| EP | 1 154 786 | 8/2000 |
| EP | 1 538 162 A2 | 6/2005 |
| EP | 1 538 162 A3 | 6/2005 |
| JP | 06-502168 A | 3/1994 |
| JP | 2002-538783 A | 11/2002 |
| JP | 2004-049133 A | 2/2004 |
| JP | 2005-519850 A | 7/2005 |
| RU | 2204388 C2 | 5/2003 |
| WO | WO 90/05744 A1 | 5/1990 |
| WO | WO 92/05784 A1 | 4/1992 |
| WO | WO 93/00353 A1 | 1/1993 |
| WO | WO 95/27496 A1 | 10/1995 |

(Continued)

OTHER PUBLICATIONS

Abraham, Office Action, 6 pages, Canada patent appl. No. 2,658,949, Canadian Intellectual Property Office (Mar. 16, 2011).

Takashi et al., "A Peptide Against the N-Terminus of Myristoylated Alanine-Rich C Kinase Substrate Inhibits Degranulation of Human Leukocytes In Vitro," Am. J. Respir. Cell. Mol. Biol. 34:647-652 (2006).

Vandenbogaerde, "Communication," and "Supplementary European Search Report," 7 pages, Europe patent appl. No. 07840538.8, European Patent Office (May 6, 2011).

(Continued)

*Primary Examiner* — Thomas S Heard
(74) *Attorney, Agent, or Firm* — Cooley LLP

(57) ABSTRACT

The present invention includes methods of inhibiting or suppressing cellular secretory processes. More specifically the present invention relates to inhibiting or reducing the release of inflammatory mediators from inflammatory cells by inhibiting the mechanism associated with the release of inflammatory mediators from granules in inflammatory cells. In this regard, the present invention discloses an intracellular signaling mechanism that illustrates several novel intracellular targets for pharmacological intervention in disorders involving secretion of inflammatory mediators from vesicles in inflammatory cells. Peptide fragments and variants thereof of MANS peptide as disclosed in the present invention are useful in such methods.

17 Claims, 13 Drawing Sheets

(56) References Cited

FOREIGN PATENT DOCUMENTS

| | | |
|---|---|---|
| WO | WO 96/18103 A1 | 6/1996 |
| WO | WO 00/50062 A2 | 8/2000 |
| WO | WO 01/20998 A1 | 3/2001 |
| WO | WO 03/000027 A2 | 1/2003 |
| WO | WO 03/000027 A3 | 5/2003 |
| WO | WO 2006/078899 A2 | 7/2006 |
| WO | WO 2006/078899 A3 | 12/2006 |
| WO | WO 2007/103368 A2 | 9/2007 |

OTHER PUBLICATIONS

Chang, "Examiner's first report on patent application No. 2007279193," 2 pages, Australia patent appl. No. 2007279193, IP Australia (Feb. 17, 2010).

Corbett, "Examination Report," 2 pages, New Zealand patent appl. No. 574290, Intellectual Property Office of New Zealand (Jun. 22, 2010).

Heard, "Written Opinion of the International Searching Authority," 3 pages, PCT appl. No. PCT/US07/74514, United States Patent and Trademark Office (mailed Jul. 14, 2008).

"Official Action," 4 pages, Russia patent appl. No. 2009106673/04, Russian Patent Office (Jun. 4, 2010) with translation.

Abdullah et al., "P2u purinoceptor regulation of mucin secretion in SPOC1 cells, a goblet cell line from the airways," Biochem. J. vol. 316, 1996, pp. 943-951.

Abdullah et al., "Protein kinase C and Ca2+ activation of mucin secretion in airway goblet cells," Am. Physiol. Soc. 273:L201-L210 (1997).

Aderem, "The MARCKS family of protein kinase-C substrates," Biochem. Soc. Trans. 23:587-591 (1995).

Adler et al., "Effects of inflammatory mediators and drugs on mucus secretion and mucociliary function," Res. Immunol. 149(3):245-248 (1998).

Adler et al., "Hypersecretion of Mucin in Response to inflammatory Mediators by Guinea Piog Tracheal Epithelial Cells In Vitro Is Blocked by Inhibition of Nitric Oxide Synthase," Am. J. Respir. Cell Mol. Biol. 13:526-530 (1995).

Adler et al., "Myristoylated alanine-rich C-kinase substrate protein: A major intracellular regulatory molecule controlling secretion of mucin by human airway goblet cells," Chest 117(5 suppl. 1):266S-267S (2000).

Aigner et al., "Depletion of 43-kD growth associated protein in primary sensory neurons leads to diminished formation and spreading of growth cones," J. Cell Biol. 123(2):417-429 (1993).

Aragona et al., "Effects of a stable analogue pf PGE2 (11-deoxy-13, 14-didehydro-16 (S)Methylester Methyl PGE2: FCE20700) on the secretory processes of conjunctival goblet cells of rabbit," Exp. Eye Res. 45(5):647-654 (1987).

Barnes, P.J., "Current and future therapies for airway mucus hypersecretion," Novartis Found Symp. 248:237-253 (2002).

Blackshear et al., "The MARCKS family of cellular protein kinase C substrates," J. Biol. Chem. 268(3):1501-1504 (1993).

Bouffard et al., National Center for Biotechnology Information Database, Accession No. G20124. Sep. 28, 1998.

Calle et al., "Glucose-induced phosphorylation of myristoylated alanine-rich C kinase substrate (MARCKS) in isolated rat pancreatic islets," J. Biol. Chem. 267(26):18723-18727 (1992).

Coffey et al., "Glutamate exocytosis and MARCKS phosphorylation are enhanced by a metabotopic glutamate receptor coupled to a protein kinase C synergistically activated by diacylglycerol and arachidonic acid," J. Neurochem. 63(4):1303-1310 (1994).

Cross et al., "Antioxidant Protection: A Function of Tracheobronchial and Gastrointestinal Mucus," The Lancet, Jun. 16,1984, pp. 1328-1329.

Dizier et al., "Genome screen for asthma and related phenotypes in the French EGEA study," American Journal Respiratory and Critical Care Medicine 162:1812-1818 (2000).

Dray-Charier et al., "Regulation of mucin secretion in human gallbladder epithelial cells: Predominant role of calcium and protein kinase C," Gastroenterology 112(3):978-990 (1997).

Driot et al., "Beneficial effects of a retinoic acid analog, CBS-211 A, on an experimental model of keraoconjunctivitis Sicca.," Invest. Opthalmol. Vis. Sci. 33(1):190-195 (1992).

Elzagallaai, A., et al. "Platelet Secretion Induced by Phorbol Esters Stimulation is Mediated Though Phosphorylation of MARCKS: a MARCKS-Derived Peptide Blocks MARCKS Phosphorylation and Serotonin Release without Affecting Pleckstrin Phosphorylation," Hemostatis, Thrombosis, and Vascular Biology. 95(3):894-902. (Feb. 1, 2000).

European Search Report for application No. 02756467.3 dated Sep. 3, 2004.

Fischer et al., "Tumor Necrosis Factor-α Stimulates Mucin Secretion and Cyclic GMP Production by Guinea Pig Tracheal Epithelial Cells In Vitro," Am. J. Respir. Cell Mol. Biol.. vol. 20. 1999, pp. 413-422.

Garcher et al., "CA 19-9 ELISA test: A new method for studying mucus changes in tears," Br. J. Ophthalmol. 82(1):88-90 (1998).

Gipson et al., "Cellular origin of mucins of the ocular surface tear film," Adv. Exp. Med. Biol. 438:221-227 (1998).

Graff et al., "Protein Kinase C Substrate and Inhibitor Characteristics of Peptides Derived from the Myristoylated Alanine-rich C Kinase Substrate (MARCKS) Protein Phosphorylation Site Domain," J. Biol. Chem. 266(22):14390-14398 (1991).

Harlan et al., "The human myristoylated alanine-rich C kinase substrate (MARCKS) gene (MACS)," J. Biol. Chem. 266(22):14399-14405 (1991).

Huse, "Partial European Search Report," 4 pages, from European Patent application No. 04024019.4, European Patent Office, The Hague, The Netherlands (mailed May 3, 2005).

International Search Report corresponding to PCT/US02/22270 mailed on Jan. 22, 2003.

International Search Report corresponding to PCT/US07/05688 mailed on Feb. 24, 2009.

International Search Report for PCT/US03/21963; mailed Sep. 9, 2004.

International Search Report for PCT/US07/74514; mailed Jul. 14, 2008.

Kessler et al., "Stimulation of goblet cell mucous secretion by activation of nerves in rat conjunctiva," Curr. Eye Res. 14(11):985-992 (1995).

Kim et al., "Airway goblet cell mucin: its structure and regulation of secretion," Eur. Resp. J. 10(11):2644-2649 (1997).

Kim et al., "Airway Mucus," Eur. Respir. J. vol. 10, 1997, p. 1438.

King et al., "Alteration of Airway Reactivity by Mucus, Respiration Physiology," vol. 62, 1985, pp. 47-59.

Ko et al., "ATP-induced mucin release from cultured airway goblet cells involves, in part, activation of protein kinase C," Am. J. Resp. Cell Mol. Biol. 16:194-198 (1997).

Krunkosky et al., "Effects of TNFα on Expression of ICAM-1 in Human Airway Epithelial Cells In Vitro," Am. J. Respir. Cell Mol. Biol., vol. 22, 2000, pp. 685-692.

Larivee et al., "Platelet-Activating Factor Induces Airway Mucin Release via Activation of Protein Kinase C: Evidence of Translocation of Protein Kinase C to Membranes," Am. J. Respir. Cell Mol. Biol., vol. 11 ,1994, pp. 194-205.

Lethem et al., "Nucleotide Regulation of Goblet Cells in Human Airway Epithelial Explants: Normal Exocytosis in Cystic Fibrosis," Am. J. Respir. Cell Mol. Biol., vol. 9, 1993, pp. 315-322.

Li, Y., et al., "MACKS Protein is a Key Molecule Regulation Mucin Secretion by Human Airway Epithelial Cells in Vitro," The Journal of Biological Chemistry. 276(44):40982-40990. (Nov. 2, 2001).

Linsen et al., "Physiology of the lacrimal system," Bull. Soc. Belge. Ophtalmol. 238:35-44 (1990).

Liu et al., "Arginine vasopressin (AVP) causes the reversible phosphorylation of the myristoylated alanine-rich C kinase substrate (MARCKS) protein in the ovine anterior pituitary: evidence that MARCKS phosphorylation is associated with adrenocorticotropin (ACTH) secretion," Mol. Cell. Endocrinol. 105:217-226 (1994).

Liu et al., "Arginine vasopressin (AVP) causes the reversible phosphorylation of the myristoylated alanine-rich C kinase substrate (MARCKS) protein in the ovine anterior pituitary: evidence that MARCKS phosphorylation is associated with adrenocorticotropin (ACTH) secretion," Mol. Cell. Endocrinol. 101:247-256 (1994).

(56) References Cited

OTHER PUBLICATIONS

Lu et al., "Regulation of angiotensin II-induced neuromodulation by MARCKS in brain neurons," J. Cell Biol. 142(1):217-227 (1998).
Mastropasqua et al., "Tear deficiency in Fuchs' intermediate uveitis," Can. J. Ophthalmol. 31(1):18-20 (1996).
Murray et al., National Center for Biotechnology Information Database, Accession No. G08525. Feb. 5, 1997.
Murray et al., National Center for Biotechnology Information Database, Accession No. G08539. Feb. 5, 1997.
Myat et al., "Identification of the basolateral targeting determinant of a peripheral membrane protein, MacMARCKS, in polarized cells," Current Biology 8(12):677-683 (1998).
Nakamura et al., "Mucin-like glycoprotein secretion is mediated by cyclic-AMP and protein kinase C signal transduction pathways in rat corneal epithelium," Exp. Eye Res. 66(5):513-519 (1998).
Nichols et al., "Demonstration of the mucous layer of the tear film by electron microscopy," Invest. Ophthalmol. Vis. Sci. 26(4):464-473 (1985).
Prescott et al, "Chronic Mucus Hypersecretion in COPD and Death From Pulmonary Infection," Eur. Respir. J., vol. 8, 1995, pp. 1333-1338.
Ralph, "Conjunctival goblet cell density in normal subjects and in dry eye syndromes," Invest. Ophthalmol. Vis. Sci. 14(4):299-302 (1975).
Raufman et al., "Expression and phosphorylation of a MARCKS-Like Protein in Gastric Chief Cells: Further evidence for modulation of pepsinogen secretion by interaction of $Ca^{2+}$/Calmodulin with protein kinase C," J. Cell. Biochem. 64:514-523 (1997).
Rogers, "Mucus hypersecretion in chronic obstructive pulmonary disease. Chronic Obstructive Pulmonary Disease: Pathogenesis to Treatment," Novartis Foundation. Symposium 234. vol. 234. (2001).
Rogers, D.F. "Airway Goblet Cell Hyperplasia in Asthma: Hypersecretory and Anti-Inflammatory?" Clinical and Experimental Allergy. Editorial 32: 1124-1127 (2002).
Rogers, D.F. "Pulmonary mucus: Pediatric Perspective," Pediatric Pulmonology 36:178-188 (2003).
Shellans et al., "Conjunctival goblet cell response to vasoconstrictor use," J. Ocul. Pharrnacol. 5(3):217-220 (1989).
Singer et al., "A MARCKS-related peptide blocks mucus hypersecretion in a moue model of asthma," Nat. Med. 10:193-196 (2004).
Steiger et al., "Concurrent Increases in the Storage and Release of Mucin-like Molecules by Rat Airway Epithelial Cells in Response to Bacterial Endotoxin," Am. J. Respir. Cell Mol. Biol., vol. 12, 1995, pp. 307-314.
Stein, "International Search Report," 5 pages, from intenational patent application PCT/US00/05050, European Patent Office, Rijswijk, The Netherlands (mailed Sep. 9, 2000).
Stormshak et al., "Dynamics of molecular mechanisms underlying ovarian oxytocin secretion," J. Reprod. Fertil. Suppl. 49:379-390 (1995).
Stumpo et al., "Molecular cloning, characterization, and expression of a cDNA encoding the '80-87-kDA' myristoylated alanine-rich C kinase substrate: A major cellular substrate for protein kinase C," Proc. Natl. Acad. Sci. USA 86:4012-4016 (1989).
Thelen et al., "Regulation by phosphorylation of the reversible association of a myristoylated protein kinase C substrate with the plasma membrane," Nature 351:320-322 (1991).
Thelen et al., "Tumor necrosis factor alpha modifies agonist-dependent responses in human neutrophils by inducing the synthesis and myristoylation of a specific protein kinase C substrate," Proc. Natl. Acad. Sci. USA 87(15):5603-5607 (1990).
Thornton et al., "Identification of Two Glycoforms of the MUC5B Mucin in Human Respiratory Mucus," The Journal of Biological Chemistry, vol. 272, No. 14, Apr. 4, 1997, pp. 9561-9566.
Tseng "Topical tretinoin treatment for severe dry-eye disorders," J. Am. Acad. Dermatol. 15(4 part 2):860-866 (1986).
Vergeres et al., "The myristoyl moiety of myristoylated alanine-rich C kinase substrate (MARCKS) and MARCKS-related protein is embedded in the membrane," J. Biol. Chem. 270(34):19879-19887 (1995).
Vishwanath et al., "Adherence of Pseudomonas aeruginosa to Human Tracheobronchial Mucin," Infection and Immunity, vol. 45, No. 1, Jul. 1984, pp. 197-202.
Ward, P.A. and Mulligan M.S., "Blocking of adhesion molecules in vivo as anti-inflammatory therapy." Ther. Immunol. 1(3):165-171 (1994).
Wjst et al., "A genome-wide search for linkage to asthma," Genomics 58:1-8, 1999.
Wright et al., "Oxidant stress stimulates mucin secretion and PLC in airway epithelium via a nitric oxide-dependent mechanism," American J. Physiol., vol. 271, pp. L854-L861 (1996).
Xu et al., "Genome-wide screen and identification of gene-gene interactions for asthma-susceptibility in three U.S. populations: Collaborative study on the genetics of asthma," American Journal of Human Genetics. 68:1437-1446 (2001).
Zhao, Y., et al. "Role of MARCKS in regulating endothelial cell proliferation." Am J Physiol Cell Physiol. 279:C1611-C1620. (2000).
Matsubara et al., "Direct Involvement of Protein Myristoylation in Myristoylated Alanine-rich C Kinase Substrate (MARCKS)-Calmodulin Interaction" Journal of Biological Chemistry, 278:48898 (2003).
Felix, "Site-Specific Poly(ethylene glycol)ylation of Peptides," ACS Symposium Series 680:218-238 (1997).
"Decision on Grant," 8 pages, from RU patent appl. No. 2008139414/14, Russian Patent Office (mailed May 11, 2011) with translation attached.
"Official Action," 9 pages, from RU patent appl. No. 2008139414/14, Russian Patent Office (mailed Jun. 3, 2010) with translation attached.
Abbas et al., "Granulocytes," $3^{rd}$ ed. Cellular and Molecular Immunology, pp. 26-27, WB Saunders Co., Philadelphia (1997).
Akbiyik et al., "In vitro and in vivo inhibition of myeloperoxidase with 5-fluorouracil," Eur. J. Clin. Pharmacol. 57:631-636 (2001).
Ali et al., "Vasopressin-induced activation of Protein kinase C in renal epithelial cells," Biochim. Biophys. Acta. 1402:188-196 (1998).
Ansfield, "A Less Toxic Fluorouracil Dosage Schedule," J. Am. Med. Assoc. 190:686-688 (1964).
Battersby et al., "Toward Larger Chemical Libraries: Encoding with Fluorescent Colloids in Combinatorial Chemistry," J. Am. Chem. Soc. 122:2138-2139 (2000).
Brinckerhoff et al., "Terminal Modifications Inhibit Proteolytic Degradation of an Immunogenic MART-$1_{27-35}$ Peptide: Implications for Peptide Vaccines," Int. J. Canc. 83(3):326-334 (1999).
Brooks et al., "MARCKS functions as a novel growth suppressor in cells of melanocyte origin," Carcinogenesis 17(4):683-689 (1996).
Brownlee, "Examiner's report No. 2 on patent application No. 2007223983," 2 pages, Australia patent appl. No. 2007223983, IP Australia (Feb. 4, 2011).
Case et al., "Lack of Efficacy of Acetaminophen in Treating Symptomatic Knee Osteoarthritis," Arch. Intern. Med. 163:169-178 (2003).
Daly, "Examination Report," 4 pages, Singapore patent appl. No. 200705330-9, Australian Patent Office (mailed Feb. 10, 2010).
Daly, "Examiner's first report on patent application No. 2006206331," 2 pages, Australia patent appl. No. 2006206331, Australia Patent Office (Dec. 14, 2010).
Daly, "Search Report," 3 pages, Singapore patent appl. No. 200705330-9, Australian Patent Office (mailed Jul. 31, 2008).
Daly, "Written Opinion," 4 pages, Singapore patent appl. No. 200705330-9, Australian Patent Office (mailed Jul. 31, 2008).
Deck, "Communication pursuant to Article 96(2) EPC," 5 pages, Europe patent appl. No. 00912034.6, European Patent Office (Apr. 25, 2002).
Deck, "International Preliminary Examination Report," 6 pages, PCT appl. No. PCT/US00/05050, European Patent Office (Nov. 27, 2000).
Desai, "Examiner's first report on patent application No. 2007223983," 3 pages, Australia patent appl. No. 2007223983, IP Australia (Aug. 24, 2009).
Dr. Shlomo Cohen & Co., Translation and Summary of Office Action issued in related Israel Patent Appl. No. 184731, 8 pages (emailed Mar. 5, 2010).

(56) References Cited

OTHER PUBLICATIONS

Epps, "Office Action Summary," 7 pages, U.S. Appl. No. 09/256,154, United States Patent and Trademark Office (mailed Feb. 3, 2000).
Epps-Ford, "Office Action Summary," 11 pages, U.S. Appl. No. 09/914,020, United States Patent and Trademark Office (mailed Jun. 6, 2005).
Epps-Ford, "Office Action Summary," 11 pages, U.S. Appl. No. 09/914,020, United States Patent and Trademark Office (mailed Mar. 22, 2007).
Epps-Ford, "Office Action Summary," 13 pages, U.S. Appl. No. 09/914,020, United States Patent and Trademark Office (mailed Feb. 23, 2004).
Epps-Ford, "Office Action Summary," 14 pages, U.S. Appl. No. 09/914,020, United States Patent and Trademark Office (mailed Dec. 7, 2005).
Epps-Ford, "Office Action Summary," 9 pages, U.S. Appl. No. 09/914,020, United States Patent and Trademark Office (mailed Aug. 28, 2006).
Epps-Smith, "Office Action Summary," 12 pages, U.S. Appl. No. 11/838,589, United States Patent and Trademark Office (mailed Jul. 19, 2010).
European Search Report, EP Appl. No. 11171749.2, 11 pages (Mar. 16, 2012).
Fujimoto, Official Action, 4 pages, Canada patent appl. No. 2,452,123, Canadian Intellectual Property Office (Sep. 22, 2009).
Gleich, "Mechanisms of eosinophil-associated inflammation," J. Allergy Clin. Immunol. 105(4):651-663 (2000).
Graff et al., "Myristoylated and Nonmyristoylated Forms of a Protein Are Phosphorylated by Protein Kinase C," Science 246(4929):503-506 (1989).
Grosskopf, "Communication pursuant to Article 94(3) EPC," 2 pages, European patent appl. No. 02756467.3, European Patent Office (May 5, 2009).
Grosskopf, "Communication pursuant to Article 94(3) EPC," 2 pages, European patent appl. No. 02756467.3, European Patent Office (Nov. 24, 2009).
Grosskopf, "Communication pursuant to Article 94(3) EPC," 3 pages, European patent appl. No. 02756467.3, European Patent Office (Jul. 9, 2010).
Grosskopf, "Communication pursuant to Article 94(3) EPC," 3 pages, European patent appl. No. 02756467.3, European Patent Office (Jun. 1, 2010).
Grosskopf, "Communication pursuant to Article 96(2) EPC," 3 pages, European patent appl. No. 02756467.3, European Patent Office (Oct. 20, 2006).
Grosskopf, "Supplementary European Search Report," 4 pages, European patent appl. No. 02756467.3, European Patent Office (Nov. 2, 2004).
Grosskopf, "Supplementary Partial European Search Report," 4 pages, European patent appl. No. 02756467.3, European Patent Office (Sep. 3, 2004).
Grosskopf, "Supplementary Partial European Search Report," 5 pages, European patent appl. No. 02756467.3, European Patent Office (Jul. 30, 2004).
Haddad, "International Preliminary Examination Report," 4 pages, PCT appl. No. PCT/US02/22270, IPEA/US United States Patent and Trademark Office (Apr. 22, 2005).
Haddad, "Office Action Summary," 10 pages, U.S. Appl. No. 10/180,753, United States Patent and Trademark Office (mailed Nov. 19, 2003).
Haddad, "Office Action Summary," 12 pages, U.S. Appl. No. 10/802,644, United States Patent and Trademark Office (mailed Nov. 30, 2004).
Haddad, "Office Action Summary," 12 pages, U.S. Appl. No. 10/802,644, United States Patent and Trademark Office (mailed Oct. 21, 2004).
Haddad, "Office Action Summary," 12 pages, U.S. Appl. No. 10/802,644, United States Patent and Trademark Office (mailed Oct. 6, 2006).
Haddad, "Office Action Summary," 14 pages, U.S. Appl. No. 10/180,753, United States Patent and Trademark Office (mailed Jul. 1, 2003).
Haddad, "Office Action Summary," 15 pages, U.S. Appl. No. 10/802,644, United States Patent and Trademark Office (mailed Jan. 11, 2006).
Haddad, "Office Action Summary," 8 pages, U.S. Appl. No. 10/802,644, United States Patent and Trademark Office (mailed Jun. 29, 2005).
Haddad, "Written Opinion," 5 pages, PCT appl. No. PCT/US02/22270, IPEA/US United States Patent and Trademark Office (Jun. 16, 2004).
Hoff et al., "Effects of glucocorticoids on the TPA-induced monocytic differentiation," J. Leukoc. Biol. 52:173-182 (1992).
Huse, "Communication pursuant to Article 96(2) EPC," 4 pages, Europe patent appl. No. 04024019.4, European Patent Office (Mar. 22, 2006).
Huse, "Communication pursuant to Article 96(2) EPC," 5 pages, Europe patent appl. No. 04024019.4, European Patent Office (Mar. 15, 2007).
Ito, "Office Action," 6 pages, Japan patent appl. No. 2000-600672, Japan Patent Office (mailed Mar. 24, 2010).
Koelsch et al., "Acetaminophen (paracetamol) inhibits myeloperoxidase-catalyzed oxidant production and biological damage at therapeutically achievable concentrations," Biochem. Pharmacol. 79:1156-1164 (2010).
Kuby, "Granulocytic Cells," $3^{rd}$ ed. Immunology, p. 67, WH Freeman & Co., New York (1997).
Lindner, "International Preliminary Report on Patentability," 6 pages, PCT appl. No. PCT/US2007/005688, The International Bureau of WIPO (Mar. 10, 2009).
Lukton, "Office Action Summary," 4 pages, U.S. Appl. No. 11/367,449, United States Patent and Trademark Office (mailed Aug. 6, 2008).
Lukton, "Office Action Summary," 7 pages, U.S. Appl. No. 11/834,446, United States Patent and Trademark Office (mailed Dec. 2, 2010).
Lukton, "Office Action Summary," 7 pages, U.S. Appl. No. 11/834,446, United States Patent and Trademark Office (mailed May 26, 2010).
Lukton, Office Action, 3 pages, U.S. Appl. No. 12/430,624, United States Patent and Trademark Office (Jun. 2, 2011).
Lukton, Office Action, 4 pages, U.S. Appl. No. 12/430,662, United States Patent and Trademark Office (Apr. 28, 2011).
Matsuura, "Office Action," 2 pages, Japan patent appl. No. 2003-506483, Japan Patent Office (Apr. 3, 2009) with translation attached.
Matsuura, "Office Action," 3 pages, Japan patent appl. No. 2003-506483, Japan Patent Office (Aug. 19, 2008) with translation attached.
McCool et al., "The T84 human colonic adenocarcinoma cell line produces mucin in culture and releases it in response to various secretagogues," Biochem J. 267:491-500 (1990).
Millecamps and Coderre, "Rats with chronic post-ischemia pain exhibit an analgesic sensitivity profile similar to human patients with complex regional pain syndrome—type I," Eur. J. Pharmacol. 583:97-102 (2008).
Office Action, CA appl. No. 2,595,406, 3 pages (Jan. 21, 2013).
Office Action, CA appl. No. 2,595,406, 3 pages (Jan. 7, 2014).
Office Action, CN 200680009056.7, 6 pages (Jan. 8, 2010).
Office Action, CN 200680009056.7, 4 pages (Dec. 14, 2010).
Office Action, CN 200680009056.7, 3 pages (Dec. 23, 2011).
Office Action, EP appl. No. 06719011.6, 2 pages (Jun. 29, 2009).
Office Action, IN appl. No. 2989/KOLNP/2007, 2 pages (Nov. 21, 2013).
Office Action, JP appl. No. 2007-552286, 4 pages (Jun. 9, 2011).
Office Action, KR appl. No. 10-2007-7018950, 5 pages (Jan. 16, 2013).
Office Action, KR appl. No. 10-2007-7018950, 4 pages (Aug. 30, 2013).
Office Action, NZ appl. No. 560412, 2 pages (Feb. 21, 2008).
Office Action, NZ appl. No. 577196, 2 pages (Sep. 10, 2010).
Office Action, NZ appl. No. 577196, 2 pages (May 26, 2011).
Office Action, RU appl. No. 2007131424/13, 2 pages (Dec. 7, 2009).

(56) References Cited

OTHER PUBLICATIONS

Office Action, RU appl. No. 2007131424/13, 2 pages (Jul. 21, 2010).
Office Action, U.S. Appl. No. 11/335,564, 6 pages (Jul. 10, 2008).
Office Action, U.S. Appl. No. 11/834,446, 3 pages (Apr. 11, 2012).
Office Action, U.S. Appl. No. 12/430,662, 4 pages (Nov. 16, 2011).
Office Action, U.S. Appl. No. 12/430,662, 4 pages (Nov. 15, 2012).
Office Action, U.S. Appl. No. 12/430,662, 4 pages (Jul. 10, 2012).
Office Action, U.S. Appl. No. 12/430,624, 4 pages (Nov. 21, 2011).
Office Action, U.S. Appl. No. 12/478,491, 6 pages (Oct. 4, 2011).
Office Action, U.S. Appl. No. 12/478,491, 7 pages (Apr. 10, 2012).
Office Action, U.S. Appl. No. 12/478,491, 6 pages (Dec. 13, 2012).
Partial European Search Report, EP Appl. No. 11171749.2, 6 pages (Nov. 25, 2011).
Pellegrini, "Supplementary European Search Report," 5 pages, European patent appl. No. 07752392.6, European Patent Office (Jun. 6, 2012).
Predel et al., "Isolation and structural elucidation of eight kinins from the retrocerebral complex of the American Cockroach, *Periplaneta americana*," Regulatory Peptides: 71(3):199-205 (1997).
Pubmed MeSH Tree for Granulocyte:(http://www.ncbi.nlm.nih.gov/mesh/68006098?ordinalpos=1&itool=EntrezSystem2.PEntrez.Mesh.Mesh_ResultsPanel.Mesh_RVDocSum) 3 pages.
Reuhman, "Examination Report," 2 pages, New Zealand patent appl. No. 570938, Intellectual Property Office of New Zealand (May 17, 2010).
Rodriguez, "International Search Report," 7 pages, PCT appl. No. PCT/US2006/002032, European Patent Office (mailed Sep. 27, 2006).
Rodriguez, "Written Opinion of the International Searching Authority," 11 pages, PCT appl. No. PCT/US2006/002032, European Patent Office (mailed Sep. 27, 2006).
Salvino, Official Action, 4 pages, Canada patent appl. No. 2,366,951, Canadian Intellectual Property Office (Apr. 7, 2009).
Seki et al., "Binding of Myristoylated Alanine-Rich Protein Kinase C Substrate to Phosphoinositides Attenuates the Phosphoroylation by Protein Kinase C," Arch. Biochem. Biophys. 326(2):193-201 (1996).
Sitzia and Huggins, "Side Effects of Cyclophosphamide, Methotrexate, and 5-Fluorouracil (CMF) Chemotherapy for Breast Cancer," Cancer Practice 6:13-21 (1998).
Steel and Hanrahan, "Muscarinic-induced mucin secretin and intracellular signaling by hamster tracheal goblet cells," Am. J. Physiol. Lung Cell Mol. Physiol. 272:230-237 (1997).
Sutherland, "Examiner's first report on patent application No. 2008200379," 2 pages, Australia patent appl. No. 2008200379, IP Australia (Jul. 31, 2009).
Theron et al., "Inhibitory Effects of Non-steroidal Anti-inflammatory Drugs on Human Myeloperoxidase," S. Afr. Med. J. 56:670-675 (1979).

\* cited by examiner

```
                        SEQUENCE LISTING

<160> NUMBER OF SEQ ID NOS: 252

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 1

Gly Ala Gln Phe Ser Lys Thr Ala Ala Lys Gly Glu Ala Ala Ala Glu
1               5                   10                  15

Arg Pro Gly Glu Ala Ala Val Ala
            20

<210> SEQ ID NO 2
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 2

Gly Ala Gln Phe Ser Lys Thr Ala Ala Lys Gly Glu Ala Ala Ala Glu
1               5                   10                  15

Arg Pro Gly Glu Ala Ala Val
            20

<210> SEQ ID NO 3
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 3

Ala Gln Phe Ser Lys Thr Ala Ala Lys Gly Glu Ala Ala Ala Glu Arg
1               5                   10                  15

Pro Gly Glu Ala Ala Val Ala
            20

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
```

```
                           modified

<400> SEQUENCE: 4

Gly Ala Gln Phe Ser Lys Thr Ala Ala Lys Gly Glu Ala Ala Ala Glu
1               5                   10                  15

Arg Pro Gly Glu Ala Ala
            20

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 5

Ala Gln Phe Ser Lys Thr Ala Ala Lys Gly Glu Ala Ala Ala Glu Arg
1               5                   10                  15

Pro Gly Glu Ala Ala Val
            20

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 6

Gln Phe Ser Lys Thr Ala Ala Lys Gly Glu Ala Ala Ala Glu Arg Pro
1               5                   10                  15

Gly Glu Ala Ala Val Ala
            20

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 7

Gly Ala Gln Phe Ser Lys Thr Ala Ala Lys Gly Glu Ala Ala Ala Glu
1               5                   10                  15

Arg Pro Gly Glu Ala
            20

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: Peptide may or may not be C-term and/or N-term
      modified

<400> SEQUENCE: 8

Ala Gln Phe Ser Lys Thr Ala Ala Lys Gly Glu Ala Ala Ala Glu Arg
1               5                   10                  15

Pro Gly Glu Ala Ala
            20

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 9

Gln Phe Ser Lys Thr Ala Ala Lys Gly Glu Ala Ala Ala Glu Arg Pro
1               5                   10                  15

Gly Glu Ala Ala Val
            20

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 10

Phe Ser Lys Thr Ala Ala Lys Gly Glu Ala Ala Ala Glu Arg Pro Gly
1               5                   10                  15

Glu Ala Ala Val Ala
            20

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 11

Gly Ala Gln Phe Ser Lys Thr Ala Ala Lys Gly Glu Ala Ala Ala Glu
1               5                   10                  15

Arg Pro Gly Glu
            20

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Peptide may or may not be C-term and/or N-term
      modified

<400> SEQUENCE: 12

Ala Gln Phe Ser Lys Thr Ala Ala Lys Gly Glu Ala Ala Ala Glu Arg
1               5                   10                  15

Pro Gly Glu Ala
            20

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 13

Gln Phe Ser Lys Thr Ala Ala Lys Gly Glu Ala Ala Ala Glu Arg Pro
1               5                   10                  15

Gly Glu Ala Ala
            20

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 14

Phe Ser Lys Thr Ala Ala Lys Gly Glu Ala Ala Ala Glu Arg Pro Gly
1               5                   10                  15

Glu Ala Ala Val
            20

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 15

Ser Lys Thr Ala Ala Lys Gly Glu Ala Ala Ala Glu Arg Pro Gly Glu
1               5                   10                  15

Ala Ala Val Ala
            20

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<223> OTHER INFORMATION: Peptide may or may not be C-term and/or N-term
      modified

<400> SEQUENCE: 16

Gly Ala Gln Phe Ser Lys Thr Ala Ala Lys Gly Glu Ala Ala Ala Glu
1               5                   10                  15

Arg Pro Gly

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 17

Ala Gln Phe Ser Lys Thr Ala Ala Lys Gly Glu Ala Ala Ala Glu Arg
1               5                   10                  15

Pro Gly Glu

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 18

Gln Phe Ser Lys Thr Ala Ala Lys Gly Glu Ala Ala Ala Glu Arg Pro
1               5                   10                  15

Gly Glu Ala

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 19

Phe Ser Lys Thr Ala Ala Lys Gly Glu Ala Ala Ala Glu Arg Pro Gly
1               5                   10                  15

Glu Ala Ala

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term modified

<400> SEQUENCE: 20

Ser Lys Thr Ala Ala Lys Gly Glu Ala Ala Ala Glu Arg Pro Gly Glu
1               5                   10                  15

Ala Ala Val

<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 21

Lys Thr Ala Ala Lys Gly Glu Ala Ala Ala Glu Arg Pro Gly Glu Ala
1               5                   10                  15

Ala Val Ala

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 22

Gly Ala Gln Phe Ser Lys Thr Ala Ala Lys Gly Glu Ala Ala Ala Glu
1               5                   10                  15

Arg Pro

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 23

Ala Gln Phe Ser Lys Thr Ala Ala Lys Gly Glu Ala Ala Ala Glu Arg
1               5                   10                  15

Pro Gly

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 24

```
Gln Phe Ser Lys Thr Ala Ala Lys Gly Glu Ala Ala Ala Glu Arg Pro
1               5                   10                  15

Gly Glu

<210> SEQ ID NO 25
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 25

Phe Ser Lys Thr Ala Ala Lys Gly Glu Ala Ala Ala Glu Arg Pro Gly
1               5                   10                  15

Glu Ala

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 26

Ser Lys Thr Ala Ala Lys Gly Glu Ala Ala Ala Glu Arg Pro Gly Glu
1               5                   10                  15

Ala Ala

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 27

Lys Thr Ala Ala Lys Gly Glu Ala Ala Ala Glu Arg Pro Gly Glu Ala
1               5                   10                  15

Ala Val

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 28

Thr Ala Ala Lys Gly Glu Ala Ala Ala Glu Arg Pro Gly Glu Ala Ala
1               5                   10                  15
```

Val Ala

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 29

Gly Ala Gln Phe Ser Lys Thr Ala Ala Lys Gly Glu Ala Ala Ala Glu
1               5                   10                  15

Arg

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 30

Ala Gln Phe Ser Lys Thr Ala Ala Lys Gly Glu Ala Ala Ala Glu Arg
1               5                   10                  15

Pro

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 31

Gln Phe Ser Lys Thr Ala Ala Lys Gly Glu Ala Ala Ala Glu Arg Pro
1               5                   10                  15

Gly

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 32

Phe Ser Lys Thr Ala Ala Lys Gly Glu Ala Ala Ala Glu Arg Pro Gly
1               5                   10                  15

Glu

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 33

Ser Lys Thr Ala Ala Lys Gly Glu Ala Ala Ala Glu Arg Pro Gly Glu
1               5                   10                  15

Ala

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 34

Lys Thr Ala Ala Lys Gly Glu Ala Ala Ala Glu Arg Pro Gly Glu Ala
1               5                   10                  15

Ala

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 35

Thr Ala Ala Lys Gly Glu Ala Ala Ala Glu Arg Pro Gly Glu Ala Ala
1               5                   10                  15

Val

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 36

Ala Ala Lys Gly Glu Ala Ala Ala Glu Arg Pro Gly Glu Ala Ala Val
1               5                   10                  15

Ala

<210> SEQ ID NO 37
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 37

Gly Ala Gln Phe Ser Lys Thr Ala Ala Lys Gly Glu Ala Ala Ala Glu
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 38

Ala Gln Phe Ser Lys Thr Ala Ala Lys Gly Glu Ala Ala Ala Glu Arg
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 39

Gln Phe Ser Lys Thr Ala Ala Lys Gly Glu Ala Ala Ala Glu Arg Pro
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 40

Phe Ser Lys Thr Ala Ala Lys Gly Glu Ala Ala Ala Glu Arg Pro Gly
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 41
```

```
Ser Lys Thr Ala Ala Lys Gly Glu Ala Ala Ala Glu Arg Pro Gly Glu
1               5                   10                  15
```

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 42

```
Lys Thr Ala Ala Lys Gly Glu Ala Ala Ala Glu Arg Pro Gly Glu Ala
1               5                   10                  15
```

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 43

```
Thr Ala Ala Lys Gly Glu Ala Ala Ala Glu Arg Pro Gly Glu Ala Ala
1               5                   10                  15
```

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 44

```
Ala Ala Lys Gly Glu Ala Ala Ala Glu Arg Pro Gly Glu Ala Ala Val
1               5                   10                  15
```

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 45

```
Ala Lys Gly Glu Ala Ala Ala Glu Arg Pro Gly Glu Ala Ala Val Ala
1               5                   10                  15
```

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: Peptide may or may not be C-term and/or N-term
      modified

<400> SEQUENCE: 46

Gly Ala Gln Phe Ser Lys Thr Ala Ala Lys Gly Glu Ala Ala Ala
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 47

Ala Gln Phe Ser Lys Thr Ala Ala Lys Gly Glu Ala Ala Ala Glu
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 48

Gln Phe Ser Lys Thr Ala Ala Lys Gly Glu Ala Ala Ala Glu Arg
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 49

Phe Ser Lys Thr Ala Ala Lys Gly Glu Ala Ala Ala Glu Arg Pro
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 50

Ser Lys Thr Ala Ala Lys Gly Glu Ala Ala Ala Glu Arg Pro Gly
1               5                   10                  15

<210> SEQ ID NO 51
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 51

Lys Thr Ala Ala Lys Gly Glu Ala Ala Ala Glu Arg Pro Gly Glu
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 52

Thr Ala Ala Lys Gly Glu Ala Ala Ala Glu Arg Pro Gly Glu Ala
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 53

Ala Ala Lys Gly Glu Ala Ala Ala Glu Arg Pro Gly Glu Ala Ala
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 54

Ala Lys Gly Glu Ala Ala Ala Glu Arg Pro Gly Glu Ala Ala Val
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 55
```

```
Lys Gly Glu Ala Ala Ala Glu Arg Pro Gly Glu Ala Ala Val Ala
1               5                   10                  15

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 56

Gly Ala Gln Phe Ser Lys Thr Ala Ala Lys Gly Glu Ala Ala
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 57

Ala Gln Phe Ser Lys Thr Ala Ala Lys Gly Glu Ala Ala Ala
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 58

Gln Phe Ser Lys Thr Ala Ala Lys Gly Glu Ala Ala Ala Glu
1               5                   10

<210> SEQ ID NO 59
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 59

Phe Ser Lys Thr Ala Ala Lys Gly Glu Ala Ala Ala Glu Arg
1               5                   10

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<223> OTHER INFORMATION: Peptide may or may not be C-term and/or N-term
      modified

<400> SEQUENCE: 60

Ser Lys Thr Ala Ala Lys Gly Glu Ala Ala Ala Glu Arg Pro
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 61

Lys Thr Ala Ala Lys Gly Glu Ala Ala Ala Glu Arg Pro Gly
1               5                   10

<210> SEQ ID NO 62
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 62

Thr Ala Ala Lys Gly Glu Ala Ala Ala Glu Arg Pro Gly Glu
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 63

Ala Ala Lys Gly Glu Ala Ala Ala Glu Arg Pro Gly Glu Ala
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 64

Ala Lys Gly Glu Ala Ala Ala Glu Arg Pro Gly Glu Ala Ala
1               5                   10

-continued

```
<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 65

Lys Gly Glu Ala Ala Ala Glu Arg Pro Gly Glu Ala Ala Val
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 66

Gly Glu Ala Ala Ala Glu Arg Pro Gly Glu Ala Ala Val Ala
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 67

Gly Ala Gln Phe Ser Lys Thr Ala Ala Lys Gly Glu Ala
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 68

Ala Gln Phe Ser Lys Thr Ala Ala Lys Gly Glu Ala Ala
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified
```

```
<400> SEQUENCE: 69

Gln Phe Ser Lys Thr Ala Ala Lys Gly Glu Ala Ala Ala
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 70

Phe Ser Lys Thr Ala Ala Lys Gly Glu Ala Ala Ala Glu
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 71

Ser Lys Thr Ala Ala Lys Gly Glu Ala Ala Ala Glu Arg
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 72

Lys Thr Ala Ala Lys Gly Glu Ala Ala Ala Glu Arg Pro
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 73

Thr Ala Ala Lys Gly Glu Ala Ala Ala Glu Arg Pro Gly
1               5                   10

<210> SEQ ID NO 74
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 74

Ala Ala Lys Gly Glu Ala Ala Ala Glu Arg Pro Gly Glu
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 75

Ala Lys Gly Glu Ala Ala Ala Glu Arg Pro Gly Glu Ala
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 76

Lys Gly Glu Ala Ala Ala Glu Arg Pro Gly Glu Ala Ala
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 77

Gly Glu Ala Ala Ala Glu Arg Pro Gly Glu Ala Ala Val
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 78

Glu Ala Ala Ala Glu Arg Pro Gly Glu Ala Ala Val Ala
1               5                   10
```

```
<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 79

Gly Ala Gln Phe Ser Lys Thr Ala Ala Lys Gly Glu
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 80

Ala Gln Phe Ser Lys Thr Ala Ala Lys Gly Glu Ala
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 81

Gln Phe Ser Lys Thr Ala Ala Lys Gly Glu Ala Ala
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 82

Phe Ser Lys Thr Ala Ala Lys Gly Glu Ala Ala Ala
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified
```

<400> SEQUENCE: 83

Ser Lys Thr Ala Ala Lys Gly Glu Ala Ala Ala Glu
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 84

Lys Thr Ala Ala Lys Gly Glu Ala Ala Ala Glu Arg
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 85

Thr Ala Ala Lys Gly Glu Ala Ala Ala Glu Arg Pro
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 86

Ala Ala Lys Gly Glu Ala Ala Ala Glu Arg Pro Gly
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 87

Ala Lys Gly Glu Ala Ala Ala Glu Arg Pro Gly Glu
1               5                   10

<210> SEQ ID NO 88
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 88

Lys Gly Glu Ala Ala Ala Glu Arg Pro Gly Glu Ala
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 89

Gly Glu Ala Ala Ala Glu Arg Pro Gly Glu Ala Ala
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 90

Glu Ala Ala Ala Glu Arg Pro Gly Glu Ala Ala Val
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 91

Ala Ala Ala Glu Arg Pro Gly Glu Ala Ala Val Ala
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 92

Gly Ala Gln Phe Ser Lys Thr Ala Ala Lys Gly
1               5                   10
```

```
<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 93

Ala Gln Phe Ser Lys Thr Ala Ala Lys Gly Glu
1               5                   10

<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 94

Gln Phe Ser Lys Thr Ala Ala Lys Gly Glu Ala
1               5                   10

<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 95

Phe Ser Lys Thr Ala Ala Lys Gly Glu Ala Ala
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 96

Ser Lys Thr Ala Ala Lys Gly Glu Ala Ala Ala
1               5                   10

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
```

-continued

```
      modified

<400> SEQUENCE: 97

Lys Thr Ala Ala Lys Gly Glu Ala Ala Ala Glu
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 98

Thr Ala Ala Lys Gly Glu Ala Ala Ala Glu Arg
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 99

Ala Ala Lys Gly Glu Ala Ala Ala Glu Arg Pro
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 100

Ala Lys Gly Glu Ala Ala Ala Glu Arg Pro Gly
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 101

Lys Gly Glu Ala Ala Ala Glu Arg Pro Gly Glu
1               5                   10

<210> SEQ ID NO 102
<211> LENGTH: 11
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 102

Gly Glu Ala Ala Ala Glu Arg Pro Gly Glu Ala
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 103

Glu Ala Ala Ala Glu Arg Pro Gly Glu Ala Ala
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 104

Ala Ala Ala Glu Arg Pro Gly Glu Ala Ala Val
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 105

Ala Ala Glu Arg Pro Gly Glu Ala Ala Val Ala
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 106

Gly Ala Gln Phe Ser Lys Thr Ala Ala Lys

```
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 107

Ala Gln Phe Ser Lys Thr Ala Ala Lys Gly
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 108

Gln Phe Ser Lys Thr Ala Ala Lys Gly Glu
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 109

Phe Ser Lys Thr Ala Ala Lys Gly Glu Ala
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 110

Ser Lys Thr Ala Ala Lys Gly Glu Ala Ala
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: Peptide may or may not be C-term and/or N-term
      modified

<400> SEQUENCE: 111

Lys Thr Ala Ala Lys Gly Glu Ala Ala Ala
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 112

Thr Ala Ala Lys Gly Glu Ala Ala Ala Glu
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 113

Ala Ala Lys Gly Glu Ala Ala Ala Glu Arg
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 114

Ala Lys Gly Glu Ala Ala Ala Glu Arg Pro
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 115

Lys Gly Glu Ala Ala Ala Glu Arg Pro Gly
1               5                   10

<210> SEQ ID NO 116
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 116

Gly Glu Ala Ala Ala Glu Arg Pro Gly Glu
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 117

Glu Ala Ala Ala Glu Arg Pro Gly Glu Ala
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 118

Ala Ala Ala Glu Arg Pro Gly Glu Ala Ala
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 119

Ala Ala Glu Arg Pro Gly Glu Ala Ala Val
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 120
```

Ala Glu Arg Pro Gly Glu Ala Ala Val Ala
1               5                   10

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 121

Gly Ala Gln Phe Ser Lys Thr Ala Ala
1               5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 122

Ala Gln Phe Ser Lys Thr Ala Ala Lys
1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 123

Gln Phe Ser Lys Thr Ala Ala Lys Gly
1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 124

Phe Ser Lys Thr Ala Ala Lys Gly Glu
1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: Peptide may or may not be C-term and/or N-term
      modified

<400> SEQUENCE: 125

Ser Lys Thr Ala Ala Lys Gly Glu Ala
1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 126

Lys Thr Ala Ala Lys Gly Glu Ala Ala
1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 127

Thr Ala Ala Lys Gly Glu Ala Ala Ala
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 128

Ala Ala Lys Gly Glu Ala Ala Ala Glu
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 129

Ala Lys Gly Glu Ala Ala Ala Glu Arg
1               5

<210> SEQ ID NO 130
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 130

Lys Gly Glu Ala Ala Ala Glu Arg Pro
1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 131

Gly Glu Ala Ala Ala Glu Arg Pro Gly
1               5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 132

Glu Ala Ala Ala Glu Arg Pro Gly Glu
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 133

Ala Ala Ala Glu Arg Pro Gly Glu Ala
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 134
```

```
Ala Ala Glu Arg Pro Gly Glu Ala Ala
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 135

Ala Glu Arg Pro Gly Glu Ala Ala Val
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 136

Glu Arg Pro Gly Glu Ala Ala Val Ala
1               5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 137

Gly Ala Gln Phe Ser Lys Thr Ala
1               5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 138

Ala Gln Phe Ser Lys Thr Ala Ala
1               5

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                                       peptide
<220> FEATURE:
<223> OTHER INFORMATION: Peptide may or may not be C-term and/or N-term
      modified

<400> SEQUENCE: 139

Gln Phe Ser Lys Thr Ala Ala Lys
1               5

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 140

Phe Ser Lys Thr Ala Ala Lys Gly
1               5

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 141

Ser Lys Thr Ala Ala Lys Gly Glu
1               5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 142

Lys Thr Ala Ala Lys Gly Glu Ala
1               5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 143

Thr Ala Ala Lys Gly Glu Ala Ala
1               5
```

-continued

```
<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 144

Ala Ala Lys Gly Glu Ala Ala Ala
1               5

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 145

Ala Lys Gly Glu Ala Ala Ala Glu
1               5

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 146

Lys Gly Glu Ala Ala Ala Glu Arg
1               5

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 147

Gly Glu Ala Ala Ala Glu Arg Pro
1               5

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified
```

```
<400> SEQUENCE: 148

Glu Ala Ala Ala Glu Arg Pro Gly
1               5

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 149

Ala Ala Ala Glu Arg Pro Gly Glu
1               5

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 150

Ala Ala Glu Arg Pro Gly Glu Ala
1               5

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 151

Ala Glu Arg Pro Gly Glu Ala Ala
1               5

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 152

Glu Arg Pro Gly Glu Ala Ala Val
1               5

<210> SEQ ID NO 153
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 153

Arg Pro Gly Glu Ala Ala Val Ala
1               5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 154

Gly Ala Gln Phe Ser Lys Thr
1               5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 155

Ala Gln Phe Ser Lys Thr Ala
1               5

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 156

Gln Phe Ser Lys Thr Ala Ala
1               5

<210> SEQ ID NO 157
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 157

Phe Ser Lys Thr Ala Ala Lys
1               5
```

-continued

```
<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 158

Ser Lys Thr Ala Ala Lys Gly
1               5

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 159

Lys Thr Ala Ala Lys Gly Glu
1               5

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 160

Thr Ala Ala Lys Gly Glu Ala
1               5

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 161

Ala Ala Lys Gly Glu Ala Ala
1               5

<210> SEQ ID NO 162
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified
```

<400> SEQUENCE: 162

Ala Lys Gly Glu Ala Ala Ala
1               5

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 163

Lys Gly Glu Ala Ala Ala Glu
1               5

<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 164

Gly Glu Ala Ala Ala Glu Arg
1               5

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 165

Glu Ala Ala Ala Glu Arg Pro
1               5

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 166

Ala Ala Ala Glu Arg Pro Gly
1               5

<210> SEQ ID NO 167
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 167

Ala Ala Glu Arg Pro Gly Glu
1               5

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 168

Ala Glu Arg Pro Gly Glu Ala
1               5

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 169

Glu Arg Pro Gly Glu Ala Ala
1               5

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 170

Arg Pro Gly Glu Ala Ala Val
1               5

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 171

Pro Gly Glu Ala Ala Val Ala
1               5
```

```
<210> SEQ ID NO 172
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 172

Gly Ala Gln Phe Ser Lys
1               5

<210> SEQ ID NO 173
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 173

Ala Gln Phe Ser Lys Thr
1               5

<210> SEQ ID NO 174
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 174

Gln Phe Ser Lys Thr Ala
1               5

<210> SEQ ID NO 175
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 175

Phe Ser Lys Thr Ala Ala
1               5

<210> SEQ ID NO 176
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
```

-continued modified

<400> SEQUENCE: 176

Ser Lys Thr Ala Ala Lys
1               5

<210> SEQ ID NO 177
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 177

Lys Thr Ala Ala Lys Gly
1               5

<210> SEQ ID NO 178
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 178

Thr Ala Ala Lys Gly Glu
1               5

<210> SEQ ID NO 179
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 179

Ala Ala Lys Gly Glu Ala
1               5

<210> SEQ ID NO 180
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 180

Ala Lys Gly Glu Ala Ala
1               5

<210> SEQ ID NO 181
<211> LENGTH: 6
<212> TYPE: PRT

<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 181

Lys Gly Glu Ala Ala Ala
1               5

<210> SEQ ID NO 182
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 182

Gly Glu Ala Ala Ala Glu
1               5

<210> SEQ ID NO 183
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 183

Glu Ala Ala Ala Glu Arg
1               5

<210> SEQ ID NO 184
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 184

Ala Ala Ala Glu Arg Pro
1               5

<210> SEQ ID NO 185
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 185

Ala Ala Glu Arg Pro Gly

-continued

```
1               5

<210> SEQ ID NO 186
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 186

Ala Glu Arg Pro Gly Glu
1               5

<210> SEQ ID NO 187
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 187

Glu Arg Pro Gly Glu Ala
1               5

<210> SEQ ID NO 188
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 188

Arg Pro Gly Glu Ala Ala
1               5

<210> SEQ ID NO 189
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 189

Pro Gly Glu Ala Ala Val
1               5

<210> SEQ ID NO 190
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

-continued

```
<223> OTHER INFORMATION: Peptide may or may not be C-term and/or N-term
      modified

<400> SEQUENCE: 190

Gly Glu Ala Ala Val Ala
1               5

<210> SEQ ID NO 191
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 191

Gly Ala Gln Phe Ser
1               5

<210> SEQ ID NO 192
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 192

Ala Gln Phe Ser Lys
1               5

<210> SEQ ID NO 193
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 193

Gln Phe Ser Lys Thr
1               5

<210> SEQ ID NO 194
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 194

Phe Ser Lys Thr Ala
1               5

<210> SEQ ID NO 195
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 195

Ser Lys Thr Ala Ala
1               5

<210> SEQ ID NO 196
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 196

Lys Thr Ala Ala Lys
1               5

<210> SEQ ID NO 197
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 197

Thr Ala Ala Lys Gly
1               5

<210> SEQ ID NO 198
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 198

Ala Ala Lys Gly Glu
1               5

<210> SEQ ID NO 199
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 199
```

Ala Lys Gly Glu Ala
1               5

<210> SEQ ID NO 200
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 200

Lys Gly Glu Ala Ala
1               5

<210> SEQ ID NO 201
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 201

Gly Glu Ala Ala Ala
1               5

<210> SEQ ID NO 202
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 202

Glu Ala Ala Ala Glu
1               5

<210> SEQ ID NO 203
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 203

Ala Ala Ala Glu Arg
1               5

<210> SEQ ID NO 204
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: Peptide may or may not be C-term and/or N-term
      modified

<400> SEQUENCE: 204

Ala Ala Glu Arg Pro
1               5

<210> SEQ ID NO 205
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 205

Ala Glu Arg Pro Gly
1               5

<210> SEQ ID NO 206
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 206

Glu Arg Pro Gly Glu
1               5

<210> SEQ ID NO 207
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 207

Arg Pro Gly Glu Ala
1               5

<210> SEQ ID NO 208
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 208

Pro Gly Glu Ala Ala
1               5

<210> SEQ ID NO 209
```

-continued

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 209

Gly Glu Ala Ala Val
1               5

<210> SEQ ID NO 210
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 210

Glu Ala Ala Val Ala
1               5

<210> SEQ ID NO 211
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 211

Gly Ala Gln Phe
1

<210> SEQ ID NO 212
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 212

Ala Gln Phe Ser
1

<210> SEQ ID NO 213
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 213
```

Gln Phe Ser Lys
1

<210> SEQ ID NO 214
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 214

Phe Ser Lys Thr
1

<210> SEQ ID NO 215
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 215

Ser Lys Thr Ala
1

<210> SEQ ID NO 216
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 216

Lys Thr Ala Ala
1

<210> SEQ ID NO 217
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 217

Thr Ala Ala Lys
1

<210> SEQ ID NO 218
<211> LENGTH: 4
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Peptide may or may not be C-term and/or N-term
      modified

<400> SEQUENCE: 218

Ala Ala Lys Gly
1

<210> SEQ ID NO 219
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 219

Ala Lys Gly Glu
1

<210> SEQ ID NO 220
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 220

Lys Gly Glu Ala
1

<210> SEQ ID NO 221
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 221

Gly Glu Ala Ala
1

<210> SEQ ID NO 222
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 222

Glu Ala Ala Ala
1

```
<210> SEQ ID NO 223
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 223

Ala Ala Ala Glu
1

<210> SEQ ID NO 224
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 224

Ala Ala Glu Arg
1

<210> SEQ ID NO 225
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 225

Ala Glu Arg Pro
1

<210> SEQ ID NO 226
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 226

Glu Arg Pro Gly
1

<210> SEQ ID NO 227
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified
```

```
<400> SEQUENCE: 227

Arg Pro Gly Glu
1

<210> SEQ ID NO 228
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 228

Pro Gly Glu Ala
1

<210> SEQ ID NO 229
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 229

Gly Glu Ala Ala
1

<210> SEQ ID NO 230
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 230

Glu Ala Ala Val
1

<210> SEQ ID NO 231
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 231

Ala Ala Val Ala
1

<210> SEQ ID NO 232
<211> LENGTH: 24
<212> TYPE: PRT
<213> ORGANISM: Artificial Sequence
<220> FEATURE:
```

-continued

```
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 232

Gly Thr Ala Pro Ala Ala Glu Gly Ala Gly Ala Glu Val Lys Arg Ala
1               5                   10                  15

Ser Ala Glu Ala Lys Gln Ala Phe
            20

<210> SEQ ID NO 233
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 233

Gly Lys Gln Phe Ser Lys Thr Ala Ala Lys Gly Glu
1               5                   10

<210> SEQ ID NO 234
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 234

Gly Ala Gln Phe Ser Lys Thr Lys Ala Lys Gly Glu
1               5                   10

<210> SEQ ID NO 235
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 235

Gly Lys Gln Phe Ser Lys Thr Lys Ala Lys Gly Glu
1               5                   10

<210> SEQ ID NO 236
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 236
```

```
Gly Ala Gln Ala Ser Lys Thr Ala Ala Lys
1               5                   10

<210> SEQ ID NO 237
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 237

Gly Ala Gln Ala Ser Lys Thr Ala Ala Lys Gly Glu
1               5                   10

<210> SEQ ID NO 238
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 238

Gly Ala Glu Phe Ser Lys Thr Ala Ala Lys Gly Glu
1               5                   10

<210> SEQ ID NO 239
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 239

Gly Ala Gln Phe Ser Lys Thr Ala Ala Ala Gly Glu
1               5                   10

<210> SEQ ID NO 240
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 240

Gly Ala Gln Phe Ser Lys Thr Ala Ala Lys Ala Glu
1               5                   10

<210> SEQ ID NO 241
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Peptide may or may not be C-term and/or N-term
      modified

<400> SEQUENCE: 241

Gly Ala Gln Phe Ser Lys Thr Ala Ala Lys Gly Ala
1               5                   10

<210> SEQ ID NO 242
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 242

Ala Ala Gln Phe Ser Lys Thr Ala Ala Lys
1               5                   10

<210> SEQ ID NO 243
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 243

Gly Ala Ala Phe Ser Lys Thr Ala Ala Lys
1               5                   10

<210> SEQ ID NO 244
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 244

Gly Ala Gln Phe Ala Lys Thr Ala Ala Lys
1               5                   10

<210> SEQ ID NO 245
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 245

Gly Ala Gln Phe Ser Ala Thr Ala Ala Lys
1               5                   10

<210> SEQ ID NO 246
```

-continued

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 246

Lys Ala Ala Thr Lys Ser Phe Gln Ala Gly
1               5                   10

<210> SEQ ID NO 247
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 247

Gly Ala Gln Phe Ser Lys Ala Ala Ala Lys
1               5                   10

<210> SEQ ID NO 248
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 248

Gly Ala Gln Phe Ser Lys Thr Ala Ala Ala
1               5                   10

<210> SEQ ID NO 249
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 249

Gly Ala Gln Phe Ser Ala Thr Ala Ala Ala
1               5                   10

<210> SEQ ID NO 250
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 250
```

```
Gly Ala Gln Ala Ser Lys Thr Ala
1               5

<210> SEQ ID NO 251
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 251

Ala Ala Gly Glu
1

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide may or may not be C-term and/or N-term
      modified

<400> SEQUENCE: 252

Gly Lys Ala Ser Gln Phe Ala Lys Thr Ala
1               5                   10
```

US 8,999,915 B2

METHODS FOR ATTENUATING RELEASE OF INFLAMMATORY MEDIATORS AND PEPTIDES USEFUL THEREIN

CROSS REFERENCE TO RELATED APPLICATION

The present application is a continuation of International Application No. PCT/US2007/074514, filed Jul. 26, 2007, which claims priority to U.S. Provisional Ser. No. 60/833,239 filed Jul. 26, 2006, each of which is incorporated in its entirety by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: BMRK 004 01US SeqList.txt, date recorded: Mar. 30, 2009, file size 80 kilobytes).

FIELD OF INVENTION

The present invention relates to peptides or peptide compositions and methods of their use to attenuate (or inhibit or reduce) the stimulated release of mediators of inflammation from inflammatory cells during inflammation. The present invention also relates to use of these peptides or peptide compositions to modulate an intracellular signaling mechanism regulating the secretion of inflammatory mediators from inflammatory cells.

BACKGROUND OF THE INVENTION

Inflammatory leukocytes synthesize a number of inflammatory mediators that are isolated intracellularly and stored in cytoplasmic membrane-bound granules. Examples of such mediators include, but are not limited to, myeloperoxidase [MPO] in neutrophils (see, for example, Borregaard N, Cowland J B. Granules of the human neutrophilic polymorphonuclear leukocyte. *Blood* 1997; 89:3503-3521), eosinophil peroxidase [EPO] and major basic protein [MBP] in eosinophils (see, for example, Gleich G J. Mechanisms of eosinophil-associated inflammation. *J Allergy Clin Immunol* 2000; 105:651-663), lysozyme in monocytes/macrophages (see, for example, Hoff T, Spencker T, Emmendoerffer A., Goppelt-Struebe M. Effects of glucocorticoids on the TPA-induced monocytic differentiation. *J Leukoc Biol* 1992; 52:173-182; and Balboa M A, Saez Y, Balsinde J. Calcium-independent phospholipase A2 is required for lysozyme secretion in U937 promonocytes. *J Immunol* 2003; 170:5276-5280), and granzyme in natural killer (NK) cells and cytotoxic lymphocytes (see, for example, Bochan M R, Goebel W S, Brahmi Z. Stably transfected antisense granzyme B and perforin constructs inhibit human granule-mediated lytic ability. *Cell Immunol* 1995; 164:234-239; Gong J H., Maki G, Klingemann H G. Characterization of a human cell line (NK-92) with phenotypical and functional characteristics of activated natural killer cells. *Leukemia* 1994; 8:652-658; Maki G, Klingemann H G, Martinson J A, Tam Y K. Factors regulating the cytotoxic activity of the human natural killer cell line, NK-92. *J Hematother Stem Cell Res* 2001; 10:369-383; and Takayama H, Trenn G, Sitkovsky M V. A novel cytotoxic T lymphocyte activation assay. *J Immunol Methods* 1987; 104: 183-190). Such mediators are released at sites of injury and contribute to inflammation and tissue repair such as in the lung and elsewhere. It is known that leukocytes release these granules via an exocytotic mechanism (see, for example, Burgoyne R D, Morgan A. Secretory granule exocytosis. *Physiol Rev* 2003; 83:581-632; and Logan M R, Odemuyiwa S O, Moqbel R. Understanding exocytosis in immune and inflammatory cells: the molecular basis of mediator secretion. *J Allergy Clin Immunol* 2003; 111: 923-932), but regulatory molecules and specific pathways involved in the exocytotic process have not been fully described.

Several exogenous stimuli can provoke degranulation of leukocytes via a pathway that involves activation of protein kinase C and subsequent phosphorylation events (see, for example, Burgoyne R D, Morgan A. Secretory granule exocytosis. *Physiol Rev* 2003; 83:581-632; Logan M R, Odemuyiwa S O, Moqbel R. Understanding exocytosis in immune and inflammatory cells: the molecular basis of mediator secretion. *J Allergy Clin Immunol* 2003; 111: 923-932; Smolen J E, Sandborg R R. Ca2+-induced secretion by electropermeabilized human neutrophils: the roles of Ca2+, nucleotides and protein kinase C. *Biochim Biophys Acta* 1990; 1052:133-142; Niessen H W, Verhoeven A J. Role of protein phosphorylation in the degranulation of electropermeabilized human neutrophils. *Biochim. Biophys. Acta* 1994; 1223:267-273; and Naucler C, Grinstein S, Sundler R., Tapper H. Signaling to localized degranulation in neutrophils adherent to immune complexes. *J Leukoc Biol* 2002; 71:701-710).

MARKS protein (where MARCKS as used herein means "Myristoylated Alanine-Rich C Kinase Substrate"), is a ubiquitous phosphorylation target of protein kinase C (PKC), and is highly expressed in leukocytes (see, for example, Aderem A A, Albert K A, Keum M M, Wang J K, Greengard P, Cohn Z A. Stimulus-dependent myristoylation of a major substrate for protein kinase C. *Nature* 1988; 332:362-364; Thelen M, Rosen A, Nairn A C, Aderem A. Regulation by phosphorylation of reversible association of a myristoylated protein kinase C substrate with the plasma membrane. *Nature* 1991; 351:320-322; and Hartwig J H, Thelen M, Rosen A, Janmey P A, Nairn A C, Aderem A. MARCKS is an actin filament crosslinking protein regulated by protein kinase C and calcium-calmodulin. *Nature* 1992; 356:618-622. MARCKS protein is mechanistically involved in a process of exocytotic secretion of mucin by goblet cells that line respiratory airways (see, for example, Li et al., *J Biol Chem* 2001; 276: 40982-40990; and Singer et al., *Nat Med* 2004; 10:193-196). MARCKS is myristoylated via an amide bond at the N-terminal amino acid in the MARCKS protein's amino acid sequence at the alpha-amine position of the glycine which resides at the N-terminus (i.e., at position 1) of amino acid sequence. In airway epithelial cells, the myristoylated N-terminal region of MARCKS appears to be integral to the secretory process. By the N-terminus of the MARCKS protein is meant the MANS peptide which contains Myristoyl-GAQF-SKTAAKGEAAAERPGEAAVA (SEQ ID NO: 1), which are L-amino acids. Additionally, the peptide fragments of the MANS peptide disclosed herein, also preferably are composed of L-amino acids. The mechanism appears to involve binding of MARCKS, a myristoylated protein, to membranes of intracellular granules.

An N-terminal myristoylated peptide from the N-terminus of MARCKS has been shown to block both mucin secretion and binding of MARCKS to mucin granule membranes in goblet cells (see, for example, Singer et al., Nat Med 2004; 10:193-196). This peptide contains 24 amino acids of the MARCKS protein beginning with the N-terminal glycine of the MARCKS protein which is myristoylated via an amide bond and is known as myristoylated alpha-N-terminal sequence (MANS); i.e., Myristoyl-GAQFSK-TAAKGEAAAERPGEAAVA (SEQ ID NO: 1). Also Vergeres et al., *J. Biochem.* 1998, 330; 5-11, discloses that the N-terminal glycine residue of MARCKS proteins is myristoylated via a reaction catalyzed by myristoyl CoA:protein N-myristoyl transferase (NMT).

In inflammatory diseases, such as asthma, COPD and chronic bronchitis; in genetic diseases such as cystic fibrosis; in allergic conditions (atopy, allergic inflammation); in bronchiectasis; and in a number of acute, infectious respiratory illnesses such as pneumonia, rhinitis, influenza or the common cold, arthritis or auto-immune diseases, inflammatory cells are usually found in or migrate to areas of injury or infection associated with inflammatory disease states, especially in or to respiratory passages or airways of patients suffering from such diseases. These inflammatory cells can contribute greatly to the pathology of diseases via tissue damage done by inflammatory mediators released from these cells. One example of such tissue damage or destruction via this chronic inflammation occurs in cystic fibrosis patients where mediators released from neutrophils (e.g., myeloperoxidase [MPO]) induce the desquamation of the airway epithelial tissue.

MARCKS, a protein of approximately 82 kD, has three evolutionarily-conserved regions (Aderem et al., Nature 1988; 332:362-364; Thelen et al., Nature 1991; 351:320-322; Hartwig et al., Nature 1992; 356:618-622; Seykora et al., J Biol Chem 1996; 271:18797-18802): an N-terminus, a phosphorylation site domain (or PSD), and a multiple homology 2 (MH2) domain. Human MARCKS cDNA and protein is known and reported by Harlan et al., *J. Biol. Chem.* 1991, 266:14399 (GenBank Accession No. M68956) and also by Sakai et al., *Genomics* 1992, 14: 175. These sequences are also provided in a WO 00/50062, which is incorporated in its entirety by reference. The N-terminus, an alpha-amino acid sequence comprising 24 amino acid residues with a myristic acid moiety attached via an amide bond to the N-terminal glycine residue is involved in binding of MARCKS to membranes in cells (Seykora et al., J Biol Chem 1996; 271:18797-18802) and possibly to calmodulin (Matsubara et al., J Biol Chem 2003; 278:48898-48902). This 24 amino acid sequence is known as the MANS peptide.

SUMMARY OF THE INVENTION

Involvement of MARCKS protein in release of inflammatory mediators from the granules of infiltrating leukocytes is relevant to inflammation in diseases in all tissues and organs, including lung diseases characterized by airway inflammation, such as asthma, COPD and cystic fibrosis. However, inflammation and mucus secretion in the airways are two separate and independent processes (Li et al., *J Biol Chem.* 2001; 276:40982-40990; Singer et al., *Nat Med* 2004; 10:193-196). While mucus production and secretion can be provoked by a number of factors, including mediators released by inflammatory cells, there is no known direct link whereby excess mucus causes inflammation.

In one aspect of this invention, the MANS peptide can play a role in the reducing the rate and/or amount of release of inflammatory mediators granules or vesicles in inflammatory leukocytes.

In another aspect, peptides derived from the MARCKS N-terminus, especially from the 24 amino acid N-terminal sequence, i.e., active contiguous peptide fragments derived from within the N-terminal 1-to-24 amino acid sequence of MARCKS having a glycine at position 1, as well as N-terminal amides of such fragments, such as N-terminal acetic acid amides of such fragments, and/or as well as C-terminal amides of such fragments, such as C-terminal amides of ammonia, can inhibit or reduce the rate and/or amount of release of inflammatory mediators from inflammatory leukocytes. Such inhibition or reduction in release comprises inhibition of a MARCKS-related release of inflammatory mediators from inflammatory leukocytes.

In another aspect, peptides derived from the MARCKS N-terminus, especially from the 1-to-24 amino acid N-terminal sequence, i.e., active contiguous peptide fragments derived from within the N-terminal 1 to 24 amino acid sequence of MARCKS having a glycine at position 1, as well as N-terminal amides of such fragments such as N-terminal acetic acid amides of such fragments, and as well as C-terminal amides of such fragments such as C-terminal amides of ammonia, can inhibit the rate of release and/or amount of release of inflammatory mediators such as those identified herein in this invention, by inhibiting the process of degranulation in inflammatory leucocytes.

In another aspect, the MANS peptide and active fragments thereof, and active amides of such fragments as described herein, can compete for membrane binding in inflammatory cells with native MARCKS protein to attenuate (lessen or reduce) MARCKS-related release of mediators of inflammation from granules or vesicles containing such mediators of inflammation in such inflammatory cells.

Leukocyte cell types and model cell types that secrete specific granule contents in response to phorbol ester induced activation of PKC are useful for in vitro demonstration of efficacy of peptides of this invention and of substituted peptides (e.g., alpha-N-amides, C-terminal amides and esters) of this invention.

The attenuation of release of membrane-bound inflammatory mediators by compounds and compositions of this invention can be demonstrated using human leukocyte cell lines. For example, neutrophils isolated from human blood can be used to demonstrate attenuation or inhibition of release of myeloperoxidase (MPO). The human promyelocytic cell line HL-60 clone 15 can be used to demonstrate attenuation of release or inhibition of release or secretion of eosinophil peroxidase (EPO) by compounds and compositions of this invention (see, for example, Fischkoff S A. Graded increase in probability of eosinophilic differentiation of HL-60 promyelocytic leukemia cells induced by culture under alkaline conditions. Leuk Res 1988; 12:679-686; Rosenberg H F, Ackerman S J, Tenen D G. Human eosinophil cationic protein: molecular cloning of a cytotoxin and helminthotoxin with ribonuclease activity. J Exp Med 1989; 170:163-176; Tiffany H L, Li F, Rosenberg H F. Hyperglycosylation of eosinophil ribonucleases in a promyelocytic leukemia cell line and in differentiated peripheral blood progenitor cells. J Leukoc Biol 1995; 58:49-54; and Badewa A P, Hudson C E, Heiman A S. Regulatory effects of eotaxin, eotaxin-2, and eotaxin-3 on eosinophil degranulation and superoxide anion generation. Exp Biol Med 2002; 227:645-651). The monocytic leukemia cell line U937 can be used to demonstrate attenuation of release or inhibition of release or secretion of lysozyme by compounds and compositions of this invention (see, for example, Hoff T, Spencker T, Emmendoerffer A., Goppelt-Struebe M. Effects of glucocorticoids on the TPA-induced monocytic differentiation. J Leukoc Biol 1992; 52:173-182; Balboa M A, Saez Y, Balsinde J. Calcium-independent phospholipase A2 is required for lysozyme secretion in U937 promonocytes. J Immunol 2003; 170:5276-5280; and Sundstrom C, Nilsson K. Establishment and characterization of a human histiocytic lymphoma cell line (U-937). Int J Cancer 1976; 17:565-577). The lymphocyte natural killer cell line NK-92 can be used to demonstrate attenuation or inhibition of release of granzyme by compounds and compositions of this invention (see, for example, Gong J H., Maki G, Klingemann H G. Characterization of a human cell line (NK-92) with phenotypical and functional characteristics of activated natural killer cells. Leukemia 1994; 8:652-658; Maki G, Klingemann H G, Martinson J A, Tam Y K. Factors regulating the cytotoxic activity of the human natural killer cell line, NK-92. J Hematother Stem Cell Res 2001; 10:369-383; and Takayama H, Trenn G, Sitkovsky M V. A novel cytotoxic T lymphocyte activation assay. J Immunol Methods 1987; 104: 183-190). In an in vitro method to inhibit or attenuate the release of a mediator of inflammation such as those described herein, each of the cell types is preincubated with a peptide compound or peptide composition of this invention over a range of concentrations followed by incubation of these cells by a stimulator of release of inflammatory mediators, such as phorbol ester. The percent of inhibition of release of a mediator of inflammation is determined as compared to the release of the mediator in the absence of the peptide compound or peptide composition, such as in a spectrophotometric readout of a concentration of the mediator released.

To demonstrate the importance of the relative amino acid sequence positioning in the peptides of the invention, the relative ability to inhibit or reduce the amount of inflammatory mediator released by a peptide which is identical to the 24 amino acid sequence of the MARCKS protein N-terminus region (i.e., the MANS-myristoylated alpha-N-terminal sequence peptide) was compared to the ability to inhibit or reduce the amount of inflammatory mediator released by a peptide containing the same 24 amino acid residues present in MANS but which are sequenced in a random order (i.e., an RNS peptide, otherwise referred to as a "Random N-terminal sequence peptide") with respect to the sequence order in MANS. In each of the cell types examined, the MANS peptide, but not the RNS peptide, attenuated release of inflammatory mediators in a concentration-dependent manner over a time course of 0.5-3.0 hrs. These results suggest that the relative amino acid sequence positioning in the peptides of the invention which are in the order found in the MARCKS protein, specifically its N-terminal region, and more specifically its 24 amino acid residue N-terminal region are involved in at least one intracellular pathway dealing with the inhibition of leukocyte degranulation.

The invention relates to a new use for the 24 amino acid peptide sequence, and to the alpha-N-terminal acetylated peptide sequence, the myristoylated polypeptide, also known as the MANS peptide, and to active fragments thereof, which active fragments can be selected from the group of peptides having from 4 to 23 contiguous amino acid residues of the MANS peptide amino acid sequence, and which fragments may be N-terminal-myristoylated if they do not begin with the N-terminal glycine at position 1 in SEQ ID NO: 1, or which may be N-terminal-acylated with C2 to C12 acyl groups, including N-terminal-acetylated, and/or C-terminal amidated with an NH2 group.

The invention also relates to a new method for blocking MARCKS-related cellular secretory processes, especially those that involve the MARCKS-related release of inflammatory mediators from inflammatory cells, whose stimulatory pathways involve the protein kinase C (PKC) substrate MARCKS protein and release of contents from intracellular vesicles or granules.

The present invention is directed to a method of inhibiting the exocytotic release of at least one inflammatory mediator from at least one inflammatory cell comprising contacting the at least one inflammatory cell, which cell comprises at least one inflammatory mediator contained within a vesicle inside the cell, with at least one peptide selected from the group consisting of a MANS peptide and an active fragment thereof as described herein in an effective amount to reduce the release of the inflammatory mediator from the inflammatory cell as compared to the release of the inflammatory mediator from the same type of inflammatory cell that would occur in the absence of the at least one peptide.

The present invention is further directed to a method of inhibiting the release of at least one inflammatory mediator from at least one inflammatory cell in a tissue or fluid of a subject comprising the administration to the subject's tissue and/or fluid, which comprises at least one inflammatory cell comprising at least one inflammatory mediator contained within a vesicle inside the cell, a therapeutically effective amount of a pharmaceutical composition comprising at least one peptide selected from the group consisting of a MANS peptide and an active fragment thereof in a therapeutically effective amount to reduce the release of the inflammatory mediator from at least one inflammatory cell as compared to release of the inflammatory mediator from at least one of the same type of inflammatory cell that would occur in the absence of the at least one peptide. More specifically, inhibiting the release of an inflammatory mediator comprises blocking or reducing the release of an inflammatory mediator from the inflammatory cell.

More particularly, the present invention includes a method of reducing inflammation in a subject comprising the administration of a therapeutically effective amount of a pharmaceutical composition comprising a MANS peptide (i.e., N-myristoyl-GAQFSKTAAKGEAAAERPGEAAVA (SEQ ID NO: 1)) or an active fragment thereof. The active fragment is at least four and preferably at least six amino acids in length. As used herein, an "active fragment" of a MARCKS protein is one that affects (inhibits or reduces) MARCKS protein-mediated release, such as MARCKS protein-mediated release of an inflammatory mediator. An active fragment can be selected from the group consisting of GAQFSKTAAKGEAAAERPGEAAV (SEQ ID NO: 2); GAQFSKTAAKGEAAAERPGEAA (SEQ ID NO: 4); GAQFSKTAAKGEAAAERPGEA (SEQ ID NO: 7); GAQFSKTAAKGEAAAERPGE (SEQ ID NO: 11); GAQFSKTAAKGEAAAERPG (SEQ ID NO: 16); GAQFSKTAAKGEAAAERP (SEQ ID NO: 22); GAQFSKTAAKGEAAAER (SEQ ID NO: 29); GAQFSKTAAKGEAAAE (SEQ ID NO: 37); GAQFSKTAAKGEAAA (SEQ ID NO: 46); GAQFSKTAAKGEAA (SEQ ID NO: 56); GAQFSKTAAKGEA (SEQ ID NO: 67); GAQFSKTAAKGE (SEQ ID NO: 79); GAQFSKTAAKG (SEQ ID NO: 92); GAQFSKTAAK (SEQ ID NO: 106); GAQFSKTAA (SEQ ID NO: 121); GAQFSKTA (SEQ ID NO: 137); GAQFSKT (SEQ ID NO: 154); GAQFSK (SEQ ID NO: 172); GAQFS (SEQ ID NO: 191) and GAQF (SEQ ID NO: 211). These peptides, instead of containing a myristoyl moiety at the N-terminal amino acid, either contain no chemical moiety or a non-myristoyl chemical moiety at the N-terminal amino acid and/or a chemical moiety at the C-terminal amino acid, such as an N-terminal acetyl group and/or a C-terminal amide group as described herein. The presence of the hydrophobic N-terminal myristoyl moiety in the MANS peptides and N-terminal myristoylated fragments thereof can enhance their compatibility with and presumably their permeability to plasma membranes, and potentially enable the peptides to be taken up by cells. The hydrophobic insertion of a myristoyl group into a membrane lipid bilayer can provide a partition coefficient or apparent association constant with lipids of up to $10^4$ $M^{-1}$ or a unitary Gibbs free binding energy of about 8 kcal/mol (see, for example, Peitzsch, R. M., and McLaughlin, S. 1993, Binding of acylated peptides and fatty acids to phospholipid vesicles: pertinence to myristoylated proteins. Biochemistry. 32: 10436-10443) which is sufficient, at least in part, to permit a partitioning of the MANS peptide and of myristoylated MANS peptide fragments into the plasma membrane of a cell while additional functional groups and their interactions within the MANS peptide (which is myristoylated) and within myristoylated MANS peptide fragments can potentiate their relative membrane permeabilities. The fragments can each exhibit partition coefficients and membrane affinities that are representative of their respective structure. The fragments can be prepared by methods of peptide synthesis known in the art, such as by solid phase peptide synthesis (see, for example, the methods described in Chan, Weng C. and White, Peter D. Eds., Fmoc Solid Phase Peptide Synthesis: A Practical Approach, Oxford University Press, New York, N.Y. (2000); and Lloyd-Williams, P. et al. Chemical Approaches to the Synthesis of Peptides and Proteins (1997)) and purified by methods known in the art, such as by high pressure liquid chromatography. Molecular weight of each peptide can be confirmed by mass spectroscopy with each showing a peak with an appropriate molecular mass. Efficacy of the individual peptides and of combinations of individual peptides (for example, combinations of 2 of the peptides, combinations of 3 of the peptides, combinations of 4 of the peptides) in the methods of this disclosure can be readily determined without undue experimentation using the procedures described in the examples disclosed herein. A preferred combination will comprise two of the peptides; a preferred molar ratio of the peptides can be from 50:50 (i.e., 1:1) to 99.99 to 0.01, which ratio can be readily determined using the procedures described in the examples disclosed herein.

Preferably the MANS peptide or active fragment thereof is contained in a pharmaceutical composition which is useful to block inflammation. The present invention also includes methods for inhibiting a cellular secretory process in a subject comprising the administration of a therapeutically effective amount of a compound comprising a MANS peptide or an active fragment thereof, that inhibits an inflammatory mediator in a subject. The administration is generally selected from the group consisting of topical administration, parenteral administration, rectal administration, pulmonary administration, inhalation and nasal or oral administration, wherein pulmonary administration generally includes either an aerosol, a dry powder inhaler, a metered dose inhaler, or a nebulizer.

Administration of a composition comprising a degranulation-inhibiting amount of the MANS peptide or a degranulation-inhibiting amount of an active fragment thereof, such as a pharmaceutical composition of the MANS peptide or an active fragment thereof, for human or animal use provides the MANS peptide or active fragment thereof at least to the site in or on a tissue or to a fluid-containing layer in contact with the surface of a tissue where an inflammatory granulocytic cell resides or into which an inflammatory granulocytic cell will invade, thus enabling the MANS peptide or an active fragment thereof to contact the inflammatory granulocytic cell. In one aspect, administration of such a composition can be made at the first onset or first detection of inflammation or first perception of inflammation by the human or animal or at the first perceptible change in the level of inflammation in a human or animal to reduce the amount of inflammation that would otherwise occur in the absence of the MANS peptide or active fragment thereof. In another aspect, administration can be made during an ongoing inflammation of a tissue in the human or animal to reduce the amount of additional inflammation that would otherwise occur in the absence of the MANS peptide or active fragment thereof. While the amount and frequency of dose can be determined by clinical evaluation and be a function of the disease or source of inflammation and the extent of tissue involved and the age and size of the patient, it is anticipated that dosing of a pharmaceutical composition can be repeated after 3 to 8 hours, preferably after 6 to 8 hours after the first administration of the pharmaceutical composition.

The present invention also includes methods of reducing inflammation in a subject comprising the administration of a therapeutically effective amount of a compound that inhibits the MARCKS-related release of inflammatory mediators, whereby the release of at least one inflammatory mediator in the subject is reduced compared to that which would occur in the absence of said treatment. As used herein "reducing" generally means a lessening of the effects of inflammation. Preferably, release of inflammatory mediators are inhibited or blocked by the methods disclosed.

Another embodiment of the present invention includes methods of reducing inflammation in a subject comprising administering a therapeutically effective amount of a compound that inhibits the MARCKS-related release of inflammatory mediators, whereby the inflammation in the subject is reduced compared to that which would occur in the absence of said treatment. The present invention also discloses methods of reducing or inhibiting inflammation in a subject comprising the administration of a therapeutically effective amount of a MANS peptide or an active fragment thereof effective to inhibit an inflammatory mediator at the inflammation site. The term "inhibiting" means a reduction in the amount of inflammatory mediator secretion. The term "completely inhibiting" means a reduction to zero in the amount of inflammatory mediator secretion. Again, as stated above, the active fragment is at least four and preferably at least six amino acids in length. The term "exocytotic process" means exocytosis, i.e., a process of cellular secretion or excretion in which substances contained in a vesicle, which vesicle resides inside a cell, are discharged from the cell by fusion of the vesicular membrane of the vesicle with the outer cell membrane. "Degranulation" means the release of cellular granule contents. The term "degranulation-inhibiting" means a reduction in the release of the inflammatory mediators contained within the granules of the inflammatory cell. Thus, a degranulation-inhibiting amount of the MANS peptide and/or an active fragment thereof is the amount of these peptides that is sufficient to reduce the release of the inflammatory mediators contained in the granules as compared to release in the absence of the same peptide.

In the reference peptide, GAQFSKTAAKGEAAAER-PGEAAVA (SEQ ID NO: 1), at the N-terminal position of the reference peptide, G is at position 1; adjacent to G at position 1 is A at position 2; adjacent to A at position 2 is Q at position 3; adjacent to Q at position 3 is F at position 4; adjacent to F at position 4 is S at position 5; adjacent to S at position 5 is K at position 6; adjacent to K at position 6 is T at position 7; adjacent to T at position 7 is A at position 8; adjacent to A at position 8 is A at position 9; adjacent to A at position 9 is K at position 10; adjacent to K at position 10 is G at position 11; adjacent to G at position 11 is E at position 12; adjacent to E at position 12 is A at position 13; adjacent to A at position 13 is A at position 14; adjacent to A at position 14 is A at position 15; adjacent to A at position 15 is E at position 16; adjacent to E at position 16 is R at position 17; adjacent to R at position 17 is P at position 18; adjacent to P at position 18 is G at position 19; adjacent to G at position 19 is E at position 20;

adjacent to E at position 20 is A at position 21; adjacent to A at position 21 is A at position 22; adjacent to A at position 22 is V at position 23; and adjacent to V at position 23 is A at position 24, wherein position 24 is the C-terminal position of the reference peptide.

A "variant" of a reference peptide or a variant of a 4 to 23 amino acid segment of a reference peptide is a peptide which has an amino acid sequence which differs from the amino acid sequence of the reference peptide or from the amino acid sequence of the segment of the reference peptide, respectively, in at least one amino acid position in the reference peptide or reference peptide segment amino acid sequence, respectively, but which retains mucin- or mucus-inhibiting activity, which activity is typically between 0.1 to 10 times the activity of the reference peptide or segment, respectively, preferably between 0.2 to 6 times the activity of the reference peptide or segment, respectively, more preferably between 0.3 to 5 times the activity of the reference peptide or segment, respectively. A "variant" of a reference amino acid sequence or a variant of a 4 to 23 amino acid segment of a reference amino acid sequence is an amino acid sequence that differs by at least one amino acid from the reference amino acid sequence or from the segment of the reference amino acid sequence, respectively, but has an amino acid sequence of a peptide that retains mucin- or mucus-inhibiting activity of the peptide or segment, respectively, encoded by the reference amino acid sequence, which activity is typically between 0.1 to 10 times the activity of the peptide or segment, respectively, of the reference sequence, preferably between 0.2 to 6 times the activity of the peptide or segment of the reference sequence, respectively, more preferably between 0.3 to 5 times the activity of the peptide or segment of the reference sequence, respectively. A substitution variant peptide or a substitution variant amino acid sequence may vary (i.e., differ) from a reference peptide or reference amino acid sequence by one or more amino acid substitutions in the reference amino acid sequence; a deletion variant peptide or a deletion variant amino acid sequence may vary (i.e., differ) from a reference peptide or reference amino acid sequence by one or more amino acid deletions in the reference amino acid sequence; and an addition variant peptide or an addition valiant amino acid sequence may vary (i.e., differ) from a reference peptide sequence or reference amino acid sequence by one or more amino acid additions in the reference sequence. A variant peptide or variant amino acid sequence can result from a substitution of one or more amino acids (e.g., substitution of at least 1, 2, 3, 4, 5, 6, 7, or 8 amino acids) in a reference sequence, or can result from a deletion of one or more amino acids (e.g., deletion of at least 1, 2, 3, 4, 5, 6, 7, or 8 amino acids) in a reference sequence, or can result from an addition of one or more amino acids (e.g., addition of at least 1, 2, 3, 4, 5, 6, 7, or 8 amino acids) in a reference sequence, or a combination thereof in any order. A substitution variant 4 to 23 amino acid peptide segment or a substitution variant 4 to 23 amino acid segment sequence may vary (i.e., differ) from a reference 4 to 23 amino acid peptide segment or reference 4 to 23 amino acid segment sequence by one or more amino acid substitutions in the reference amino acid segment sequence; a deletion variant 4 to 23 amino acid peptide segment or a 4 to 22 amino acid deletion variant amino acid segment sequence may vary (i.e., differ) from a 5 to 23 reference peptide segment or a 5 to 23 amino acid reference amino acid segment sequence by one or more amino acid deletions in the reference amino acid segment sequence; and an 4 to 23 amino acid addition valiant peptide or a 4 to 23 amino acid addition variant amino acid sequence may vary (i.e., differ) from a 4 to 22 amino acid reference peptide sequence or a 4 to 22 amino acid reference amino acid sequence by one or more amino acid additions in the reference sequence. A 4 to 23 amino acid variant peptide or a 4 to 23 amino acid variant amino acid sequence can result from a substitution of one or more amino acids (e.g., substitution of at least 1, 2, 3, 4, 5, 6, 7, 8 amino acids) in a 4 to 23 amino acid segment of a reference amino acid sequence, or can result from a deletion of one or more amino acids (e.g., deletion of at least 1, 2, 3, 4, 5, 6, 7, or 8 amino acids) in a respectively larger reference amino acid sequence, or can result from an addition of one or more amino acids (e.g., addition of at least 1, 2, 3, 4, 5, 6, 7, or 8 amino acids) in a respectively smaller reference amino acid sequence, or from a combination thereof. Preferably, a variant peptide or amino acid sequence varies from a reference peptide or from a segment of a reference peptide or from a reference amino acid sequence or from a segment of a reference amino acid sequence, respectively, by less than 10 amino acid substitutions, deletions, and/or additions; more preferably less than 8 amino acid substitutions, deletions, and/or additions; even more preferably less than 6 amino acid substitutions, deletions, and/or additions; and even more preferably less than 5 amino acid substitutions, deletions, and/or additions; and yet even more preferably less than 4 amino acid substitutions, deletions, and/or additions. Most preferably the variant amino acid sequence differs from a reference peptide or segment amino acid sequence by one or two or three amino acids.

"Sequence identity" means, with respect to amino acid sequences of two peptides, the number of positions with identical amino acids divided by the number of amino acids in the shorter of the two sequences.

"Substantially identical" means, with respect to comparison of the amino acid sequences of two peptides or comparison of the amino acid sequences of two peptide segments (e.g. segments of a reference peptide amino acid sequence), that the amino acid sequence of the peptides or segments of peptides have at least 75% sequence identity, preferably at least 80% sequence identity, more preferably at least 90% sequence identity, and most preferably at least 95% sequence identity.

The term "peptide" as used herein includes the peptide as well as pharmaceutically acceptable salts of the peptide.

An "isolated" peptide, as used herein, means a naturally-occurring peptide that has been separated or substantially separated from the cellular components (e.g., nucleic acids and other peptides) that naturally accompany it by purification, recombinant synthesis, or chemical synthesis, and also encompasses non-naturally-occurring recombinantly or chemically synthesized peptides that have been purified or substantially purified from cellular components, biological materials, chemical precursors, or other chemicals.

The following three-letter and one-letter amino acid abbreviations are used throughout the text: Alanine: (Ala) A; Arginine: (Arg) R; Asparagine: (Asn) N; Aspartic acid: (Asp) D; Cysteine: (Cys) C; Glutamine: (Gln) Q; Glutamic acid: (Glu) E; Glycine: (Gly) G; Histidine: (His) H; Isoleucine: (Ile) I; Leucine: (Leu) L; Lysine: (Lys) K; Methionine: (Met) M; Phenylalanine: (Phe) F; Proline: (Pro) P; Serine: (Ser) S; Threonine: (Thr) T; Tryptophan: (Trp) W; Tyrosine: (Tyr) Y; Valine: (Val) V. Additional three letter symbols of amino acids useful herein include, in brackets, (Hyp) for hydroxyproline, (Nle) for norleucine, (Orn) for ornithine, (Pyr) for pyroglutamic acid and (Sar) for sarcosine. By convention, the amino (or N-terminal) end of a peptide appears at the left end of a written amino acid sequence of the peptide and the carboxy (or C-terminal) end appears at the right end of a written amino acid sequence. The amino acid sequence of a peptide can be written in single letter symbols to represent the amino acids which are covalently linked by peptide amide bonds in the peptide.

Active fragments of the MANS peptide can be useful in the prevention or reduction in amount of inflammation in a tissue in an animal caused by inflammatory mediators. Active fragments of the MANS peptide also can be useful in the prevention or reduction in amount of tissue damage in an animal produced or caused by inflammatory mediators. An active fragment of the MANS peptide is composed of at least 4 contiguous amino acids and no more than 23 contiguous amino acids of the MANS peptide (SEQ ID NO: 1). The term "active fragment" within the context of the present invention is intended to encompass those fragments of the MANS peptides that are capable of preventing or reducing the release of inflammatory mediators from an inflammatory cell. The reduction of release of inflammatory mediators by the active figments can range from at least 5% to at least 99% reduction as compared to a reference peptide, such as MANS peptide.

Table 1 contains a list of amino acid sequences in single letter abbreviation format together with a respectively corresponding peptide number and SEQ ID NO. The reference peptide amino acid sequence (MANS peptide) is listed as peptide 1. Amino acid sequences of peptides of the invention having an amino acid sequence of from 4 to 23 contiguous amino acids of the reference amino acid sequence are listed as peptides 2 to 231, together with the amino acid sequence of a random N-terminal sequence (RNS) comprising amino acids of the MANS peptide as peptide 232. Amino acid sequences of representative variants of amino acid sequences of peptides of the invention as described herein and are also listed as peptides 233 to 245 and 247 to 251. This variant peptides listed are not intended to be a limiting group of peptides, but are presented only to serve as representative examples of variant peptides of the invention. Also presented is a representative reverse amino acid sequence (peptide 246) and a representative random amino acid sequence of peptide (peptide 232) of the invention. The reverse and random amino acid sequences in the table are not intended to be representative of the invention.

Table 1 contains a listing of peptides of this invention and their respective amino acid sequences and corresponding SEQ ID NOS.

TABLE 1

Peptides and Amino Acid Sequences

| Peptide No. | Sequence | Sequence ID No. |
|---|---|---|
| peptide 1 | GAQFSKTAAKGEAAAERPGEAAVA | SEQ ID NO. 1 |
| peptide 2 | GAQFSKTAAKGEAAAERPGEAAV | SEQ ID NO. 2 |
| peptide 3 | AQFSKTAAKGEAAAERPGEAAVA | SEQ ID NO. 3 |
| peptide 4 | GAQFSKTAAKGEAAAERPGEAA | SEQ ID NO. 4 |
| peptide 5 | AQFSKTAAKGEAAAERPGEAAV | SEQ ID NO. 5 |
| peptide 6 | QFSKTAAKGEAAAERPGEAAVA | SEQ ID NO. 6 |
| peptide 7 | GAQFSKTAAKGEAAAERPGEA | SEQ ID NO. 7 |
| peptide 8 | AQFSKTAAKGEAAAERPGEAA | SEQ ID NO. 8 |
| peptide 9 | QFSKTAAKGEAAAERPGEAAV | SEQ ID NO. 9 |
| peptide 10 | FSKTAAKGEAAAERPGEAAVA | SEQ ID NO. 10 |
| peptide 11 | GAQFSKTAAKGEAAAERPGE | SEQ ID NO. 11 |
| peptide 12 | AQFSKTAAKGEAAAERPGEA | SEQ ID NO. 12 |
| peptide 13 | QFSKTAAKGEAAAERPGEAA | SEQ ID NO. 13 |
| peptide 14 | FSKTAAKGEAAAERPGEAAV | SEQ ID NO. 14 |
| peptide 15 | SKTAAKGEAAAERPGEAAVA | SEQ ID NO. 15 |
| peptide 16 | GAQFSKTAAKGEAAAERPG | SEQ ID NO. 16 |
| peptide 17 | AQFSKTAAKGEAAAERPGE | SEQ ID NO. 17 |
| peptide 18 | QFSKTAAKGEAAAERPGEA | SEQ ID NO. 18 |
| peptide 19 | FSKTAAKGEAAAERPGEAA | SEQ ID NO. 19 |
| peptide 20 | SKTAAKGEAAAERPGEAAV | SEQ ID NO. 20 |
| peptide 21 | KTAAKGEAAAERPGEAAVA | SEQ ID NO. 21 |
| peptide 22 | GAQFSKTAAKGEAAAERP | SEQ ID NO. 22 |
| peptide 23 | AQFSKTAAKGEAAAERPG | SEQ ID NO. 23 |
| peptide 24 | QFSKTAAKGEAAAERPGE | SEQ ID NO. 24 |
| peptide 25 | FSKTAAKGEAAAERPGEA | SEQ ID NO. 25 |
| peptide 26 | SKTAAKGEAAAERPGEAA | SEQ ID NO. 26 |
| peptide 27 | KTAAKGEAAAERPGEAAV | SEQ ID NO. 27 |
| peptide 28 | TAAKGEAAAERPGEAAVA | SEQ ID NO. 28 |
| peptide 29 | GAQFSKTAAKGEAAAER | SEQ ID NO. 29 |
| peptide 30 | AQFSKTAAKGEAAAERP | SEQ ID NO. 30 |
| peptide 31 | QFSKTAAKGEAAAERPG | SEQ ID NO. 31 |
| peptide 32 | FSKTAAKGEAAAERPGE | SEQ ID NO. 32 |
| peptide 33 | SKTAAKGEAAAERPGEA | SEQ ID NO. 33 |
| peptide 34 | KTAAKGEAAAERPGEAA | SEQ ID NO. 34 |
| peptide 35 | TAAKGEAAAERPGEAAV | SEQ ID NO. 35 |
| peptide 36 | AAKGEAAAERPGEAAVA | SEQ ID NO. 36 |
| peptide 37 | GAQFSKTAAKGEAAAE | SEQ ID NO. 37 |
| peptide 38 | AQFSKTAAKGEAAAER | SEQ ID NO. 38 |
| peptide 39 | QFSKTAAKGEAAAERP | SEQ ID NO. 39 |
| peptide 40 | FSKTAAKGEAAAERPG | SEQ ID NO. 40 |
| peptide 41 | SKTAAKGEAAAERPGE | SEQ ID NO. 41 |
| peptide 42 | KTAAKGEAAAERPGEA | SEQ ID NO. 42 |
| peptide 43 | TAAKGEAAAERPGEAA | SEQ ID NO. 43 |
| peptide 44 | AAKGEAAAERPGEAAV | SEQ ID NO. 44 |
| peptide 45 | AKGEAAAERPGEAAVA | SEQ ID NO. 45 |
| peptide 46 | GAQFSKTAAKGEAAA | SEQ ID NO. 46 |
| peptide 47 | AQFSKTAAKGEAAAE | SEQ ID NO. 47 |
| peptide 48 | QFSKTAAKGEAAAER | SEQ ID NO. 48 |

TABLE 1-continued

Peptides and Amino Acid Sequences

| Peptide No. | Sequence | Sequence ID No. |
|---|---|---|
| peptide 49 | FSKTAAKGEAAAERP | SEQ ID NO. 49 |
| peptide 50 | SKTAAKGEAAAERPG | SEQ ID NO. 50 |
| peptide 51 | KTAAKGEAAAERPGE | SEQ ID NO. 51 |
| peptide 52 | TAAKGEAAAERPGEA | SEQ ID NO. 52 |
| peptide 53 | AAKGEAAAERPGEAA | SEQ ID NO. 53 |
| peptide 54 | AKGEAAAERPGEAAV | SEQ ID NO. 54 |
| peptide 55 | KGEAAAERPGEAAVA | SEQ ID NO. 55 |
| peptide 56 | GAQFSKTAAKGEAA | SEQ ID NO. 56 |
| peptide 57 | AQFSKTAAKGEAAA | SEQ ID NO. 57 |
| peptide 58 | QFSKTAAKGEAAAE | SEQ ID NO. 58 |
| peptide 59 | FSKTAAKGEAAAER | SEQ ID NO. 59 |
| peptide 60 | SKTAAKGEAAAERP | SEQ ID NO. 60 |
| peptide 61 | KTAAKGEAAAERPG | SEQ ID NO. 61 |
| peptide 62 | TAAKGEAAAERPGE | SEQ ID NO. 62 |
| peptide 63 | AAKGEAAAERPGEA | SEQ ID NO. 63 |
| peptide 64 | AKGEAAAERPGEAA | SEQ ID NO. 64 |
| peptide 65 | KGEAAAERPGEAAV | SEQ ID NO. 65 |
| peptide 66 | GEAAAERPGEAAVA | SEQ ID NO. 66 |
| peptide 67 | GAQFSKTAAKGEA | SEQ ID NO. 67 |
| peptide 68 | AQFSKTAAKGEAA | SEQ ID NO. 68 |
| peptide 69 | QFSKTAAKGEAAA | SEQ ID NO. 69 |
| peptide 70 | FSKTAAKGEAAAE | SEQ ID NO. 70 |
| peptide 71 | SKTAAKGEAAAER | SEQ ID NO. 71 |
| peptide 72 | KTAAKGEAAAERP | SEQ ID NO. 72 |
| peptide 73 | TAAKGEAAAERPG | SEQ ID NO. 73 |
| peptide 74 | AAKGEAAAERPGE | SEQ ID NO. 74 |
| peptide 75 | AKGEAAAERPGEA | SEQ ID NO. 75 |
| peptide 76 | KGEAAAERPGEAA | SEQ ID NO. 76 |
| peptide 77 | GEAAAERPGEAAV | SEQ ID NO. 77 |
| peptide 78 | EAAAERPGEAAVA | SEQ ID NO. 78 |
| peptide 79 | GAQFSKTAAKGE | SEQ ID NO. 79 |
| peptide 80 | AQFSKTAAKGEA | SEQ ID NO. 80 |
| peptide 81 | QFSKTAAKGEAA | SEQ ID NO. 81 |
| peptide 82 | FSKTAAKGEAAA | SEQ ID NO. 82 |
| peptide 83 | SKTAAKGEAAAE | SEQ ID NO. 83 |
| peptide 84 | KTAAKGEAAAER | SEQ ID NO. 84 |
| peptide 85 | TAAKGEAAAERP | SEQ ID NO. 85 |
| peptide 86 | AAKGEAAAERPG | SEQ ID NO. 86 |
| peptide 87 | AKGEAAAERPGE | SEQ ID NO. 87 |
| peptide 88 | KGEAAAERPGEA | SEQ ID NO. 88 |
| peptide 89 | GEAAAERPGEAA | SEQ ID NO. 89 |
| peptide 90 | EAAAERPGEAAV | SEQ ID NO. 90 |
| peptide 91 | AAAERPGEAAVA | SEQ ID NO. 91 |
| peptide 92 | GAQFSKTAAKG | SEQ ID NO. 92 |
| peptide 93 | AQFSKTAAKGE | SEQ ID NO. 93 |
| peptide 94 | QFSKTAAKGEA | SEQ ID NO. 94 |
| peptide 95 | FSKTAAKGEAA | SEQ ID NO. 95 |
| peptide 96 | SKTAAKGEAAA | SEQ ID NO. 96 |
| peptide 97 | KTAAKGEAAAE | SEQ ID NO. 97 |
| peptide 98 | TAAKGEAAAER | SEQ ID NO. 98 |
| peptide 99 | AAKGEAAAERP | SEQ ID NO. 99 |
| peptide 100 | AKGEAAAERPG | SEQ ID NO. 100 |
| peptide 101 | KGEAAAERPGE | SEQ ID NO. 101 |
| peptide 102 | GEAAAERPGEA | SEQ ID NO. 102 |
| peptide 103 | EAAAERPGEAA | SEQ ID NO. 103 |
| peptide 104 | AAAERPGEAAV | SEQ ID NO. 104 |
| peptide 105 | AAERPGEAAVA | SEQ ID NO. 105 |
| peptide 106 | GAQFSKTAAK | SEQ ID NO. 106 |
| peptide 107 | AQFSKTAAKG | SEQ ID NO. 107 |
| peptide 108 | QFSKTAAKGE | SEQ ID NO. 108 |
| peptide 109 | FSKTAAKGEA | SEQ ID NO. 109 |
| peptide 110 | SKTAAKGEAA | SEQ ID NO. 110 |
| peptide 111 | KTAAKGEAAA | SEQ ID NO. 111 |
| peptide 112 | TAAKGEAAAE | SEQ ID NO. 112 |
| peptide 113 | AAKGEAAAER | SEQ ID NO. 113 |
| peptide 114 | AKGEAAAERP | SEQ ID NO. 114 |
| peptide 115 | KGEAAAERPG | SEQ ID NO. 115 |
| peptide 116 | GEAAAERPGE | SEQ ID NO. 116 |
| peptide 117 | EAAAERPGEA | SEQ ID NO. 117 |
| peptide 118 | AAAERPGEAA | SEQ ID NO. 118 |
| peptide 119 | AAERPGEAAV | SEQ ID NO. 119 |
| peptide 120 | AERPGEAAVA | SEQ ID NO. 120 |
| peptide 121 | GAQFSKTAA | SEQ ID NO. 121 |
| peptide 122 | AQFSKTAAK | SEQ ID NO. 122 |
| peptide 123 | QFSKTAAKG | SEQ ID NO. 123 |

TABLE 1-continued

Peptides and Amino Acid Sequences

| Peptide No. | Sequence | Sequence ID No. |
|---|---|---|
| peptide 124 | FSKTAAKGE | SEQ ID NO. 124 |
| peptide 125 | SKTAAKGEA | SEQ ID NO. 125 |
| peptide 126 | KTAAKGEAA | SEQ ID NO. 126 |
| peptide 127 | TAAKGEAAA | SEQ ID NO. 127 |
| peptide 128 | AAKGEAAAE | SEQ ID NO. 128 |
| peptide 129 | AKGEAAAER | SEQ ID NO. 129 |
| peptide 130 | KGEAAAERP | SEQ ID NO. 130 |
| peptide 131 | GEAAAERPG | SEQ ID NO. 131 |
| peptide 132 | EAAAERPGE | SEQ ID NO. 132 |
| peptide 133 | AAAERPGEA | SEQ ID NO. 133 |
| peptide 134 | AAERPGEAA | SEQ ID NO. 134 |
| peptide 135 | AERPGEAAV | SEQ ID NO. 135 |
| peptide 136 | ERPGEAAVA | SEQ ID NO. 136 |
| peptide 137 | GAQFSKTA | SEQ ID NO. 137 |
| peptide 138 | AQFSKTAA | SEQ ID NO. 138 |
| peptide 139 | QFSKTAAK | SEQ ID NO. 139 |
| peptide 140 | FSKTAAKG | SEQ ID NO. 140 |
| peptide 141 | SKTAAKGE | SEQ ID NO. 141 |
| peptide 142 | KTAAKGEA | SEQ ID NO. 142 |
| peptide 143 | TAAKGEAA | SEQ ID NO. 143 |
| peptide 144 | AAKGEAAA | SEQ ID NO. 144 |
| peptide 145 | AKGEAAAE | SEQ ID NO. 145 |
| peptide 146 | KGEAAAER | SEQ ID NO. 146 |
| peptide 147 | GEAAAERP | SEQ ID NO. 147 |
| peptide 148 | EAAAERPG | SEQ ID NO. 148 |
| peptide 149 | AAAERPGE | SEQ ID NO. 149 |
| peptide 150 | AAERPGEA | SEQ ID NO. 150 |
| peptide 151 | AERPGEAA | SEQ ID NO. 151 |
| peptide 152 | ERPGEAAV | SEQ ID NO. 152 |
| peptide 153 | RPGEAAVA | SEQ ID NO. 153 |
| peptide 154 | GAQFSKT | SEQ ID NO. 154 |
| peptide 155 | AQFSKTA | SEQ ID NO. 155 |
| peptide 156 | QFSKTAA | SEQ ID NO. 156 |
| peptide 157 | FSKTAAK | SEQ ID NO. 157 |
| peptide 158 | SKTAAKG | SEQ ID NO. 158 |
| peptide 159 | KTAAKGE | SEQ ID NO. 159 |
| peptide 160 | TAAKGEA | SEQ ID NO. 160 |
| peptide 161 | AAKGEAA | SEQ ID NO. 161 |
| peptide 162 | AKGEAAA | SEQ ID NO. 162 |
| peptide 163 | KGEAAAE | SEQ ID NO. 163 |
| peptide 164 | GEAAAER | SEQ ID NO. 164 |
| peptide 165 | EAAAERP | SEQ ID NO. 165 |
| pepride 166 | AAAERPG | SEQ ID NO. 166 |
| peptide 167 | AAERPGE | SEQ ID NO. 167 |
| peptide 168 | AERPGEA | SEQ ID NO. 168 |
| peptide 169 | ERPGEAA | SEQ ID NO. 169 |
| peptide 170 | RPGEAAV | SEQ ID NO. 170 |
| peptide 171 | PGEAAVA | SEQ ID NO. 171 |
| peptide 172 | GAQFSK | SEQ ID NO. 172 |
| peptide 173 | AQFSKT | SEQ ID NO. 173 |
| peptide 174 | QFSKTA | SEQ ID NO. 174 |
| peptide 175 | FSKTAA | SEQ ID NO. 175 |
| peptide 176 | SKTAAK | SEQ ID NO. 176 |
| peptide 177 | KTAAKG | SEQ ID NO. 177 |
| peptide 178 | TAAKGE | SEQ ID NO. 178 |
| peptide 179 | AAKGEA | SEQ ID NO. 179 |
| peptide 180 | AKGEAA | SEQ ID NO. 180 |
| peptide 181 | KGEAAA | SEQ ID NO. 181 |
| peptide 182 | GEAAAE | SEQ ID NO. 182 |
| peptide 183 | EAAAER | SEQ ID NO. 183 |
| peptide 184 | AAAERP | SEQ ID NO. 184 |
| peptide 185 | AAERPG | SEQ ID NO. 185 |
| peptide 186 | AERPGE | SEQ ID NO. 186 |
| peptide 187 | ERPGEA | SEQ ID NO. 187 |
| peptide 188 | RPGEAA | SEQ ID NO. 188 |
| peptide 189 | PGEAAV | SEQ ID NO. 189 |
| peptide 190 | GEAAVA | SEQ ID NO. 190 |
| peptide 191 | GAQFS | SEQ ID NO. 191 |
| peptide 192 | AQFSK | SEQ ID NO. 192 |
| peptide 193 | QFSKT | SEQ ID NO. 193 |
| peptide 194 | FSKTA | SEQ ID NO. 194 |
| peptide 195 | SKTAA | SEQ ID NO. 195 |
| peptide 196 | KTAAK | SEQ ID NO. 196 |
| peptide 197 | TAAKG | SEQ ID NO. 197 |
| peptide 198 | AAKGE | SEQ ID NO. 198 |

TABLE 1-continued

Peptides and Amino Acid Sequences

| Peptide No. | Sequence | Sequence ID No. |
|---|---|---|
| peptide 199 | AKGEA | SEQ ID NO. 199 |
| peptide 200 | KGEAA | SEQ ID NO. 200 |
| peptide 201 | GEAAA | SEQ ID NO. 201 |
| peptide 202 | EAAAE | SEQ ID NO. 202 |
| peptide 203 | AAAER | SEQ ID NO. 203 |
| peptide 204 | AAERP | SEQ ID NO. 204 |
| peptide 205 | AERPG | SEQ ID NO. 205 |
| peptide 206 | ERPGE | SEQ ID NO. 206 |
| peptide 207 | RPGEA | SEQ ID NO. 207 |
| peptide 208 | PGEAA | SEQ ID NO. 208 |
| peptide 209 | GEAAV | SEQ ID NO. 209 |
| peptide 210 | EAAVA | SEQ ID NO. 210 |
| peptide 211 | GAQF | SEQ ID NO. 211 |
| peptide 212 | AQFS | SEQ ID NO. 212 |
| peptide 213 | QFSK | SEQ ID NO. 213 |
| peptide 214 | FSKT | SEQ ID NO. 214 |
| peptide 215 | SKTA | SEQ ID NO. 215 |
| peptide 216 | KTAA | SEQ ID NO. 216 |
| peptide 217 | TAAK | SEQ ID NO. 217 |
| peptide 218 | AAKG | SEQ ID NO. 218 |
| peptide 219 | AKGE | SEQ ID NO. 219 |
| peptide 220 | KGEA | SEQ ID NO. 220 |
| peptide 221 | GEAA | SEQ ID NO. 221 |
| peptide 222 | EAAA | SEQ ID NO. 222 |
| peptide 223 | AAAE | SEQ ID NO. 223 |
| peptide 224 | AAER | SEQ ID NO. 224 |
| peptide 225 | AERP | SEQ ID NO. 225 |
| peptide 226 | ERPG | SEQ ID NO. 226 |
| peptide 227 | RPGE | SEQ ID NO. 227 |
| peptide 228 | PGEA | SEQ ID NO. 228 |
| peptide 229 | GEAA | SEQ ID NO. 229 |
| peptide 230 | EAAV | SEQ ID NO. 230 |
| peptide 231 | AAVA | SEQ ID NO. 231 |
| peptide 232 | GTAPAAEGAGAEVKRASAEAKQAF | SEQ ID NO. 232 |
| peptide 233 | GKQFSKTAAKGE | SEQ ID NO. 233 |
| peptide 234 | GAQFSKTKAKGE | SEQ ID NO. 234 |
| peptide 235 | GKQFSKTKAKGE | SEQ ID NO. 235 |
| peptide 236 | GAQASKTAAK | SEQ ID NO. 236 |
| peptide 237 | GAQASKTAAKGE | SEQ ID NO. 237 |
| peptide 238 | GAEFSKTAAKGE | SEQ ID NO. 238 |
| peptide 239 | GAQFSKTAAAGE | SEQ ID NO. 239 |
| peptide 240 | GAQFSKTAAKAE | SEQ ID NO. 240 |
| peptide 241 | GAQFSKTAAKGA | SEQ ID NO. 241 |
| peptide 242 | AAQFSKTAAK | SEQ ID NO. 242 |
| peptide 243 | GAAFSKTAAK | SEQ ID NO. 243 |
| peptide 244 | GAQFAKTAAK | SEQ ID NO. 244 |
| peptide 245 | GAQFSATAAK | SEQ ID NO. 245 |
| peptide 246 | KAATKSFQAG | SEQ ID NO. 246 |
| peptide 247 | GAQFSKAAAK | SEQ ID NO. 247 |
| peptide 248 | GAQFSKTAAA | SEQ ID NO. 248 |
| peptide 249 | GAQFSATAAA | SEQ ID NO. 249 |
| peptide 250 | GAQASKTA | SEQ ID NO. 250 |
| peptide 251 | AAGE | SEQ ID NO. 251 |
| peptide 252 | GKASQFAKTA | SEQ ID NO. 252 |

An amino acid sequence of a peptide listed in Table 1 can be chemically modified. For example, if an amino acid sequence of a peptide listed in Table 1 is chemically modified at the N-terminal amine to form an amide with a carboxylic acid, the resulting peptide is sometimes referred to herein by a combination of an identifier for the carboxylic acid as a prefix linked by a hyphen to the peptide number. For example, with respect to peptide 79 as an example, an N-terminal myristoylated peptide 79 may sometimes be referred to herein as "myristoylated-peptide 79" or "myr-peptide 79"; an N-terminal acetylated peptide 79 may sometimes be referred to herein as "acetyl-peptide 79" or "Ac-peptide 79". A cyclic version of peptide 79 may be referred to as "cyclic-peptide 79" or "cyc-peptide 79". Also, for example, if an amino acid sequence of a peptide listed in Table 1 is chemically modified at the C-terminal carboxylic group, for example by an amine such as ammonia to form a C-terminal amide, the resulting peptide is sometimes referred to herein by a combination of an identifier for the amine residue as a suffix linked by a hyphen to the peptide number. Thus, for example, a C-terminal amide of peptide 79 can be sometimes referred to as "peptide-NH2". When the N-terminal amine of the peptide (e.g., peptide 79) is chemically modified by, for example, a myristoyl group and the C-terminal carboxylic group is chemically modified by, for example, an ammonia group to form an amide as above, the resulting peptide can be sometimes referred to, using both prefix and suffix notation, as "myr-peptide 79-NH2".

The invention involves peptides having amino acid sequences comprising less than 24 amino acids with amino acid sequences related to the amino acid sequence of MANS peptide (i.e., the MANS peptide is myristoyl-peptide 1 and the reference 24-amino acid sequence of the MANS peptide is peptide 1). The peptides of the current invention consist of amino acid sequences containing less than 24 amino acids, and may consist of from 8 to 14, from 10 to 12, from 9 to 14, from 9 to 13, from 10 to 13, from 10 to 14, at least 9, at least 10, or the like amino acids. The peptides are typically straight chains, but may be cyclic peptides as well. In addition, the peptides may be isolated peptides.

With respect to peptide 1 (SEQ ID NO: 1), the reference 24 amino acid sequence, a segment of 23 continuous amino acids of the reference amino acid sequence is sometimes referred to herein as a 23-mer. Analogously, a segment of 22 continuous amino acids of the reference sequence is sometimes referred to herein as a 22-mer; a 21 amino acid sequence as a 21-mer; a 20 amino acid sequence as a 20-mer; a 19 amino acid sequence as a 19-mer; an 18 amino acid sequence as an 18-mer; a 17 amino acid sequence as a 17-mer; a 16 amino acid sequence as a 16-mer; a 15 amino acid sequence as a 15-mer; a 14 amino acid sequence as a 14-mer; a 13 amino acid sequence as a 13-mer; a 12 amino acid sequence as a 12-mer; an 11 amino acid sequence as an 1-mer; a 10 amino acid sequence as a 10-mer; a 9 amino acid sequence as a 9-mer; an 8 amino acid sequence as an 8-mer; a 7 amino acid sequence as a 7-mer; a 6 amino acid sequence as a 6-mer; a 5 amino acid sequence as a 5-mer; and a 4 amino acid sequence as a 4-mer. In one aspect, any of these "4- to 23-mer" amino acid sequences, which are themselves peptides (sometimes herein denoted as H2N-peptide-COOH), can be independently chemically modified, for example, by chemical modification, which chemical modification can be selected from the group consisting of (i) amide formation at the N-terminal amine group (H2N-peptide-) such as with, for example, a C1 or preferably with a C2 (acetic acid) to C22 carboxylic acid; (ii) amide formation at the C-terminal carboxylic group (-peptide-COOH) such as with, for example, ammonia or with a C1 to C22 primary or secondary amine; and (iii) a combination of thereof.

The peptides have an amino acid sequence selected from the group consisting of (a) an amino acid sequence having from 4 to 23 contiguous amino acids of the reference sequence, peptide 1; (b) a sequence substantially similar to the amino acid sequence defined in (a); and (c) a variant of the amino acid sequence defined in (a), which variant is selected from the group consisting of a substitution variant, a deletion variant, an addition variant, and combinations thereof. In some embodiments, the peptides have an amino acid sequence selected from the group consisting of: (a) an amino acid sequence having from 8 to 14 contiguous amino acids of the reference sequence, peptide 1; (b) an amino acid sequence substantially identical to the sequence defined in (a); and (c) a valiant of the amino acid sequence defined in (a), which variant is selected from the group consisting of a substitution variant, a deletion variant, an addition variant, and combinations thereof. In yet other embodiments, the peptides have an amino acid sequence selected from the group consisting of: (a) an amino acid sequence having from 10 to 12 contiguous amino acids of the reference sequence, peptide 1; (b) an amino acid sequence substantially identical to the sequence defined in (a); and (c) a variant of the amino acid sequence defined in (a), which variant is selected from the group consisting of a substitution variant, a deletion variant, an addition variant, and combinations thereof. In further embodiments, the peptides have an amino acid sequence having at least 9, at least 10, from 9 to 14, from 9 to 13, from 10 to 13, from 10 to 14, or the like contiguous amino acids of the reference sequence, peptide 1; an amino acid sequence substantially identical thereto; or a variant thereof, which variant is selected from the group consisting of a substitution variant, a deletion variant, an addition valiant, and combinations thereof. As explained further below, one or more of the amino acids of the peptides (e.g., the N-terminal and/or C-terminal amino acids) may be optionally independently chemically modified; in some embodiments, one or more amino acids of a peptide will be chemically modified while in other embodiments none of the amino acids of the peptide will be chemically modified. In one aspect, preferred modification can occur at the amine (—NH$_2$) group of the N-terminal amino acid of the peptide or peptide segment (which amine group would form a peptide amide bond if present internally within a peptide sequence rather than at the N-terminal position). In another aspect, preferred modification can occur at the carboxy (—COOH) group of the C-terminal amino acid of the peptide or peptide segment (which carboxy group would form a peptide amide bond if present internally within a peptide sequence rather than at the C-terminal position). In another aspect, preferred modification can occur at both the N-terminal amine (—NH$_2$) group and at the C-terminal carboxylic (—COOH) group.

In some embodiments, the amino acid sequence of the peptide begins from the N-terminal amino acid of the reference sequence peptide 1. For example, the peptides may have an amino acid sequence selected from the group consisting of (a) an amino acid sequence having from 4 to 23 contiguous amino acids of the reference sequence peptide 1, wherein the amino acid sequence begins from the N-terminal amino acid of the reference sequence (i.e., peptide 2, peptide 4, peptide 7, peptide 11, peptide 16, peptide 22, peptide 29, peptide 37, peptide 46, peptide 56, peptide 67, peptide 79, peptide 92, peptide 106, peptide 121, peptide 137, peptide 154, peptide 172, peptide 191, or peptide 211); (b) a sequence substantially similar to the amino acid sequence defined in (a); and (c) a variant of the amino acid sequence defined in (a). These peptides contain no chemical moiety or a chemical moiety on the N-terminal glycine other than a myristoyl group. Preferably, the chemical moiety is an acyl group, in the form of an amide bond, such as an acetyl group, or alkyl group.

In other embodiments, the amino acid sequence of the peptide ends at the C-terminal amino acid of the reference sequence peptide 1. For example, the peptides may have an amino acid sequence selected from the group consisting of (a) an amino acid sequence having from 4 to 23 contiguous amino acids of the reference sequence peptide 1, wherein the amino acid sequence ends at the C-terminal amino acid of the reference sequence (i.e., peptide 3, peptide 6, peptide 10, peptide 15, peptide 21, peptide 28, peptide 36, peptide 45, peptide 55, peptide 66, peptide 78, peptide 91, peptide 105, peptide 120, peptide 136, peptide 153, peptide 171, peptide 190, peptide 210, or peptide 231); (b) a sequence substantially similar to the amino acid sequence defined in (a); and (c) a variant of the amino acid sequence defined in (a).

In other embodiments, the amino acid sequence of the peptide does not begin at the N-terminal amino acid of the reference sequence, peptide 1, (SEQ ID NO: 1) but rather begins at the amino acid at position 2 through the amino acid at position 21 of the reference sequence peptide 1. For example, the peptides may have an amino acid sequence selected from the group consisting of (a) an amino acid sequence having from 4 to 23 contiguous amino acids of the reference sequence peptide 1, wherein the amino acid sequence begins at any amino acid between position 2 through position 21 of the reference sequence. These peptides may be between 4 and 23 contiguous amino acids long and may represent peptides in the middle of the reference sequence, peptide 1; (b) a sequence substantially similar to the amino acid sequence defined in (a); and (c) a variant of the amino acid sequence defined in (a). These peptides are disclosed in Tables 1 or 2. These peptides may contain no covalently bound chemical moiety or a chemical moiety on the N-terminal amino acid which is not the N-terminal glycine from or equivalent to the N-terminal glycine of the amino acid sequence SEQ ID NO: 1. Preferably, the chemical moiety is an acyl group, such as an acetyl group or a myristoyl group, in the form of an amide bond, or an alkyl group.

Peptide amino acid sequences which are useful in the current invention to inhibit mucin hypersecretion in a mammal, and which are useful to reduce the amount of mucin hypersecretion in a mammal, and which are useful in the methods of inhibition of mucin hypersecretion and in the methods of reduction of mucin hypersecretion include amino acid sequences of isolated peptides and amino acid sequences of peptides which optionally contain N-terminal- and/or C-terminal-chemically modified groups of the current invention, which peptide amino acid sequences are selected from the group consisting of the 23-mers (i.e., peptides having a 23 amino acid sequence): peptide 2; and peptide 3; the 22-mers (i.e., peptides having a 22 amino acid sequence): peptide 4; peptide 5; and peptide 6; the 21-mers (i.e., peptides having a 21 amino acid sequence): peptide 7; peptide 8; peptide 9; and peptide 10; the 20-mers (i.e., peptides having a 20 amino acid sequence): peptide 11; peptide 12; peptide 13; peptide 14; and peptide 15; the 19-mers (i.e., peptides having a 19 amino acid sequence): peptide 16; peptide 17; peptide 18; peptide 19; peptide 20; and peptide 21; the 18-mers (i.e., peptides having a 18 amino acid sequence): peptide 22; peptide 23; peptide 25; peptide 26; peptide 27; and peptide 28; the 17-mers (i.e., peptides having a 17 amino acid sequence): peptide 29; peptide 30; peptide 31; peptide 32; peptide 33; peptide 34; peptide 35; and peptide 36; the 16-mers (i.e., peptides having a 16 amino acid sequence): peptide 37; peptide 38; peptide 39; peptide 40; peptide 41; peptide 42; peptide 43; peptide 44; and peptide 45; the 15-mers (i.e., peptides having a 15 amino acid sequence): peptide 46; peptide 47; peptide 48; peptide 49; peptide 50; peptide 51; peptide 52; peptide 53; peptide 54; and peptide 55; the 14-mers (i.e., peptides having a 14 amino acid sequence): peptide 56; peptide 57; peptide 58; peptide 59; peptide 60; peptide 61; peptide 62; peptide 63; peptide 64; peptide 65; and peptide 66; the 13-mers (i.e., peptides having a 13 amino acid sequence): peptide 67; peptide 68; peptide 69; peptide 70; peptide 71; peptide 72; peptide 73; peptide 74; peptide 75; peptide 76; peptide 77; and peptide 78; the 12-mers (i.e., peptides having a 12 amino acid sequence): peptide 79; peptide 80; peptide 81; peptide 82; peptide 83; peptide 84; peptide 85; peptide 86; peptide 87; peptide 88; peptide 89; peptide 90; and peptide 91; the 11-mers (i.e., peptides having a 11 amino acid sequence): peptide 92; peptide 93; peptide 94; peptide 95; peptide 96; peptide 97; peptide 98; peptide 99; peptide 100; peptide 101; peptide 102; peptide 103; peptide 104; and peptide 105; the 10-mers (i.e., peptides having a 10 amino acid sequence): peptide 106; peptide 107; peptide 108; peptide 109; peptide 110; peptide 111; peptide 112; peptide 113; peptide 114; peptide 115; peptide 116; peptide 117; peptide 118; peptide 119; and peptide 120; the 9-mers (i.e., peptides having a 9 amino acid sequence): peptide 121; peptide 122; peptide 123; peptide 124; peptide 125; peptide 126; peptide 127; peptide 128; peptide 129; peptide 130; peptide 131; peptide 132; peptide 133; peptide 134; peptide 135; and peptide 136; the 8-mers (i.e., peptides having a 8 amino acid sequence): peptide 137; peptide 138; peptide 139; peptide 140; peptide 141; peptide 142; peptide 143; peptide 144; peptide 145; peptide 146; peptide 147; peptide 148; peptide 149; peptide 150; peptide 151; peptide 152; and peptide 153; the 7-mers (i.e., peptides having a 7 amino acid sequence): peptide 154; peptide 155; peptide 156; peptide 157; peptide 158; peptide 159; peptide 160; peptide 161; peptide 162; peptide 163; peptide 164; peptide 165; peptide 166; peptide 167; peptide 168; peptide 169; peptide 170; and peptide 171; the 6-mers (i.e., peptides having a 6 amino acid sequence): peptide 172; peptide 173; peptide 174; peptide 175; peptide 176; peptide 177; peptide 178; peptide 179; peptide 180; peptide 181; peptide 182; peptide 183; peptide 184; peptide 185; peptide 186; peptide 187; peptide 188; peptide 189; and peptide 190; the 5-mers (i.e., peptides having a 5 amino acid sequence): peptide 191; peptide 192; peptide 193; peptide 194; peptide 195; peptide 196; peptide 197; peptide 198; peptide 199; peptide 200; peptide 201; peptide 202; peptide 203; peptide 204; peptide 205; peptide 206; peptide 207; peptide 208; peptide 209; and peptide 210; and the 4-mers (i.e., peptides having a 4 amino acid sequence): peptide 211; peptide 212; peptide 213; peptide 214; peptide 215; peptide 216; peptide 217; peptide 218; peptide 219; peptide 220; peptide 221; peptide 222; peptide 223; peptide 224; peptide 225; peptide 226; peptide 227; peptide 228; peptide 229; peptide 230; and peptide 231.

Preferred amino acid sequences of isolated peptides and of N-terminal- and/or C-terminal-chemically modified peptides of the current invention are selected from the group consisting of the 23-mers: peptide 2; and peptide 3; the 22-mers: peptide 4; peptide 5; and peptide 6; the 21-mers: peptide 7; peptide 8; peptide 9; and peptide 10; the 20-mers: peptide 11; peptide 12; peptide 13; peptide 14; and peptide 15; the 19-mers: peptide 16; peptide 17; peptide 18; peptide 19; peptide 20; and peptide 21; the 18-mers: peptide 22; peptide 23; peptide 24; peptide 25; peptide 26; peptide 27; and peptide 28; the 17-mers: peptide 29; peptide 30; peptide 31; peptide 32; peptide 33; peptide 34; peptide 35; and peptide 36; the 16-mers: peptide 37; peptide 38; peptide 39; peptide 40; peptide 41; peptide 42; peptide 43; peptide 44; and peptide 45; the 15-mers: peptide 46; peptide 47; peptide 48; peptide 49; peptide 50; peptide 51; peptide 52; peptide 53; and peptide 54; the 14-mers: peptide 56; peptide 57; peptide 58; peptide 59; peptide 60; peptide 61; peptide 62; peptide 63; and peptide 64; the 13-mers: peptide 67; peptide 68; peptide 69; peptide 70; peptide 71; peptide 72; peptide 73; peptide 74; and peptide 75; the 12-mers: peptide 79; peptide 80; peptide 81; peptide 82; peptide 83; peptide 84; peptide 85; peptide 86; and peptide 87; the 11-mers: peptide 92; peptide 93; peptide 94; peptide 95; peptide 96; peptide 97; peptide 98; peptide 99; and peptide 100; the 10-mers: peptide 106; peptide 107; peptide 108; peptide 109; peptide 110; peptide 111; peptide 112; peptide 113; and peptide 114; the 9-mers: peptide 122; peptide 123; peptide 124; peptide 125; peptide 126; peptide 127; peptide 128; and peptide 129; the 8-mers: peptide 139; peptide 140; peptide 141; peptide 142; peptide 143; peptide 144; and peptide 145; the 7-mers: peptide 157; peptide 158; peptide 159; peptide 160; peptide 161; and peptide 162; the 6-mers: peptide 176; peptide 177; peptide 178; peptide 179; and peptide 180; the 5-mers: peptide 196; peptide 197; peptide 198; and peptide 199; and the 4-mers: peptide 217; and peptide 219.

More preferred amino acid sequences of isolated peptides and of N-terminal- and/or C-terminal-chemically modified peptides of the current invention are selected from the group consisting of the 23-mers: peptide 2; and peptide 3; the 22-mers: peptide 4; peptide 5; and peptide 6; the 21-mers: peptide 7; peptide 8; peptide 9; and peptide 10; the 20-mers: peptide 11; peptide 12; peptide 13; peptide 14; and peptide 15; the 19-mers: peptide 16; peptide 17; peptide 18; peptide 19; peptide 20; and peptide 21; the 18-mers: peptide 22; peptide 23; peptide 24; peptide 25; peptide 26; peptide 27;

and peptide 28; the 17-mers: peptide 29; peptide 30; peptide 31; peptide 32; peptide 33; peptide 34; peptide 35; and peptide 36; the 16-mers: peptide 37; peptide 38; peptide 39; peptide 40; peptide 41; peptide 42; peptide 43; peptide 44; and peptide 45; the 15-mers: peptide 46; peptide 47; peptide 48; peptide 49; peptide 50; peptide 51; peptide 52; peptide 53; and peptide 54; the 14-mers: peptide 56; peptide 57; peptide 58; peptide 59; peptide 60; peptide 61; peptide 62; peptide 63; and peptide 64; the 13-mers: peptide 67; peptide 68; peptide 69; peptide 70; peptide 71; peptide 72; peptide 73; peptide 74; peptide 80; peptide 81; peptide 82; peptide 83; peptide 84; peptide 85; peptide 86; and peptide 87; the 11-mers: peptide 92; peptide 93; peptide 94; peptide 95; peptide 96; peptide 97; peptide 98; peptide 99; and peptide 100; the 10-mers: peptide 106; peptide 108; peptide 109; peptide 110; peptide 111; peptide 112; peptide 113; and peptide 114; the 9-mers: peptide 124; peptide 125; peptide 126; peptide 127; peptide 128; and peptide 129; the 8-mers: peptide 141; peptide 142; peptide 143; peptide 144; and peptide 145; the 7-mers: peptide 159; peptide 160; peptide 161; and peptide 162; the 6-mers: peptide 178; peptide 179; and peptide 180; the 5-mers: peptide 198; and peptide 199; and the 4-mer: peptide 219.

In yet other embodiments, the amino acid sequence of the peptide includes the contiguous residues A, K, G, and E as in peptide 219 of the reference sequence peptide 1. For example, the peptides may have an amino acid sequence selected from the group consisting of (a) an amino acid sequence having from 4 to 23 contiguous amino acids of the reference sequence peptide 1, wherein the amino acid sequence of the peptide includes the contiguous residues A, K, G, and E as in peptide 219 of the reference peptide 1 (e.g., peptide 219, peptide 45, peptide 79, peptide 67, peptide 80, etc.); (b) a sequence substantially similar to the amino acid sequence defined in (a); and (c) a variant of the amino acid sequence defined in (a).

Examples of peptide segments which contain the amino acid sequence AKGE of the reference peptide amino acid sequence, peptide 1, include (a) the 23-mers: peptide 2; and peptide 3; the 22-mers: peptide 4; peptide 5; and peptide 6; the 11-mers: peptide 7; peptide 8; peptide 9; and peptide 10; the 20-mers: peptide 1; peptide 12; peptide 13; peptide 14; and peptide 15; the 19-mers: peptide 16; peptide 17; peptide 18; peptide 19; peptide 20; and peptide 21; the 18-mers: peptide 22; peptide 23; peptide 24; peptide 25; peptide 26; peptide 27; and peptide 28; the 17-mers: peptide 29; peptide 30; peptide 31; peptide 32; peptide 33; peptide 34; peptide 35; and peptide 36; the 16-mers: peptide 37; peptide 38; peptide 39; peptide 40; peptide 41; peptide 42; peptide 43; peptide 44; and peptide 45; the 15-mers: peptide 46; peptide 47; peptide 48; peptide 49; peptide 50; peptide 51; peptide 52; peptide 53; and peptide 54; the 14-mers: peptide 56; peptide 57; peptide 58; peptide 59; peptide 60; peptide 61; peptide 62; peptide 63; and peptide 64; the 13-mers: peptide 67; peptide 68; peptide 69; peptide 70; peptide 71; peptide 72; peptide 73; peptide 74; and peptide 75; the 12-mers: peptide 79; peptide 80; peptide 81; peptide 82; peptide 83; peptide 84; peptide 85; peptide 86; and peptide 87; the 11-mers: peptide 93; peptide 94; peptide 95; peptide 96; peptide 97; peptide 98; peptide 99; and peptide 100; the 10-mers: peptide 108; peptide 109; peptide 110; peptide 111; peptide 112; peptide 113; and peptide 114; the 9-mers: peptide 124; peptide 125; peptide 126; peptide 127; peptide 128; and peptide 129; the 8-mers: peptide 141; peptide 142; peptide 143; peptide 144; and peptide 145; the 7-mers: peptide 159; peptide 160; peptide 161; and peptide 162; the 6-mers: peptide 178; peptide 179; and peptide 180; the 5-mers: peptide 198; and peptide 199; and the 4-mer: peptide 219, (b) a sequence substantially similar to the amino acid sequence defined in (a); and (c) a variant of the amino acid sequence defined in (a), which variant is selected from the group consisting of a substitution variant, a deletion variant, an addition variant, and combinations thereof, wherein the segment comprises or consists of from 4 to 23 contiguous amino acids.

In another embodiment, preferred peptide sequences have an amino acid sequence selected from the group consisting of (a) an amino acid sequence having from 10 to 23 contiguous amino acids of the reference sequence, peptide 1; (b) a sequence substantially similar to the amino acid sequence defined in (a); and (c) a variant of the amino acid sequence defined in (a), which variant is selected from the group consisting of a substitution variant, a deletion valiant, an addition variant, and combinations thereof, wherein the preferred amino acid sequences comprise the 23-mer: peptide 2; the 22-mer: peptide 4; the 21-mer: peptide 7; the 20-mer: peptide 11; the 19-mer: peptide 16; the 18-mer: peptide 22; the 7-mer: peptide 29; the 16-mer: peptide 37; the 15-mer: peptide 46; the 14-mer: peptide 56; the 13-mer: peptide 67; the 12-mer: peptide 79; the 11-mer: peptide 92; and the 10-mer: peptide 106.

In further embodiments, the amino acid sequence of the peptide begins from the N-terminal amino acid of the reference sequence peptide 1 and includes the contiguous residues A, K, G, and E as in peptide 219 of the reference sequence peptide 1, while in other embodiments the amino acid sequence of the peptide ends at the C-terminal amino acid of the reference sequence peptide 1 and includes the contiguous residues A, K, G, and E as in peptide 219 of the reference sequence peptide 1.

The peptides may include one or more amino acid deletions, substitutions, and/or additions with respect to the reference amino acid sequence. Preferably, the substitutions may be conservative amino acid substitutions, or the substitutions may be non-conservative amino acid substitutions. In some embodiments, the peptides, including the peptides with amino acid sequences that are substantially identical to or variants of the reference amino acid sequence, will not have deletions or additions as compared to the corresponding contiguous amino acids of the reference amino acid sequence, but may have conservative or non-conservative substitutions. Amino acid substitutions that may be made to the reference amino acid sequence in the peptides of the invention include, but are not limited to, the following: alanine (A) may be substituted with lysine (K), valine (V), leucine (L), or isoleucine (I); glutamic acid (E) may be substituted with aspartic acid (D); glycine (G) may be substituted with proline (P); lysine (K) may be substituted with arginine (R), glutamine (Q), or asparagine (N); phenylalanine (F) may be substituted with leucine (L), valine (V), isoleucine (I), or alanine (A); proline (P) may be substituted with glycine (G); glutamine (Q) may be substituted with glutamic acid (E) or asparagine (N); arginine (R) may be substituted with lysine (K), glutamine (Q), or asparagine (N); serine (S) may be substituted with threonine; threonine (T) may be substituted with serine (S); and valine (V) may be substituted with leucine (L), isoleucine (I), methionine (M), phenylalanine (F), alanine (A), or norleucine (Nle). For example, substitutions that could be made to the reference amino acid sequence in the peptides of the invention include substituting alanine (A) for phenylalanine (F) (e.g., at amino acid position 4 of the reference amino acid sequence), glutamic acid (E) for glutamine (Q) (e.g., at amino acid position 3 of the reference amino acid sequence), lysine (K) for alanine (A) (e.g., at amino acid positions 2 and/or 8 of the reference amino acid sequence), and/or serine (S) for threonine (T) (e.g., at amino acid position 7 of the reference amino acid sequence).

When substitutions are included in the amino acid sequences of the peptides of the invention (which peptides comprise unmodified as well as peptides which are chemically modified for example by N-terminal and/or C-terminal modification such as by amide formation) with respect to the reference amino acid sequence, there is preferably at least 80% sequence identity between the amino acid sequence of the peptide and the reference amino acid sequence. Peptides having 5 to 23 amino acids and including one amino acid substitution with respect to the reference amino acid sequence will have between about 80% to about 96% (i.e., ~95.7%) sequence identity to the reference amino acid sequence. Peptides having 10 to 23 amino acids and including one amino acid substitution with respect to the reference amino acid sequence will have between about 90% to about 96% (i.e., ~95.7%) sequence identity to the reference amino acid sequence. Peptides having 20 to 23 amino acids and including one amino acid substitution with respect to the reference amino acid sequence will have between about 95% to about 96% (i.e., ~95.7%) sequence identity to the reference amino acid sequence. Peptides having 10 to 23 amino acids and including two amino acid substitutions with respect to the reference amino acid sequence will have between about 80% to about 92% (i.e., ~91.3%) sequence identity to the reference amino acid sequence. Peptides having 16 to 23 amino acids and including two amino acid substitutions with respect to the reference amino acid sequence will have between about 87.5% to about 92% (i.e., ~91.3%) sequence identity to the reference amino acid sequence. Peptides having 20 to 23 amino acids and including two amino acid substitutions with respect to the reference amino acid sequence will have between about 90% to about 92% (i.e., ~91.3%) sequence identity to the reference amino acid sequence. Peptides having 15 to 23 amino acids and including three amino acid substitutions with respect to the reference amino acid sequence will have between about 80% to about 87% sequence identity to the reference amino acid sequence. Peptides having 20 to 23 amino acids and including three amino acid substitutions with respect to the reference amino acid sequence will have between about 85% to about 87% sequence identity to the reference amino acid sequence. Peptides having 20 to 23 amino acids and including four amino acid substitutions with respect to the reference amino acid sequence will have between about 80% to about 83% (i.e., ~82.6%) sequence identity to the reference amino acid sequence.

In peptides of the current invention, with respect to the contiguous amino acid sequence of the reference peptide (which is a 24-mer) substitution of one amino acid in a contiguous 23 amino acid sequence (a 23-mer) selected from the reference 24 amino acid sequence provides a peptide with an amino acid sequence which has a 95.65% (or ~96%) sequence identity to the amino acid segment in the reference peptide with which the 23-mer has identity. Analogously, substitution of two, three, four, and five amino acids in said 23-mer provides a peptide with an amino acid sequence which has a 91.30% (or ~91%), 86.96% (or ~87%), 82.61% (or ~83%), and 78.27% (or ~78%) sequence identity, respectively, to the reference peptide amino acid sequence. Analogously, substitution of one, two, three, four, and five amino acids in a 22-mer provides a peptide with an amino acid sequence which has a 95.45% (or ~95%), 90.91% (or ~91%), 86.36% (or ~86%), 81.82% (or ~82%), and 77.27% (or ~77%) sequence identity, respectively, to the reference peptide amino acid sequence. Analogously, substitution of one, two, three, four, and five amino acids in a 21-mer provides a peptide with an amino acid sequence which has a 95.24% (~95%), 90.48 (~91%), 85.71% (~86%), 80.95 (~81%), and 76.19% (~76%) sequence identity, respectively, to the reference peptide amino acid sequence. Analogously, substitution of one, two, three, four, and five amino acids in a 20-mer provides a peptide with an amino acid sequence which has a 95.00% (95%), 90.00% (90%), 85.00% (85%), 80.00% (80%), and 75.00% (75%) sequence identity, respectively, to the reference peptide amino acid sequence. Analogously, substitution of one, two, three, and four amino acids in a 19-mer provides a peptide with an amino acid sequence which has a 94.74% (~95%), 89.47% (~89%), 84.21% (~84%), and 78.95% (~79%) sequence identity, respectively, to the reference peptide amino acid sequence. Analogously, substitution of one, two, three, and four amino acids in an 18-mer provides a peptide with an amino acid sequence which has a 94.44% (~94%), 88.89% (~89%), 83.33% (~83%), and 77.78% (~78%) sequence identity, respectively, to the reference peptide amino acid sequence. Analogously, substitution of one, two, three, and four amino acids in an 17-mer provides a peptide with an amino acid sequence which has a 94.12% (~94%), 88.23% (~88%), 82.35% (~82%), and 76.47% (~76%) sequence identity, respectively, to the reference peptide amino acid sequence. Analogously, substitution of one, two, three, and four amino acids in a 16-mer provides a peptide with an amino acid sequence which has a 93.75% (~94%), 87.50% (~88%), 81.25% (~81%), and 75.00% (75%) sequence identity, respectively, to the reference peptide amino acid sequence. Analogously, substitution of one, two, and three amino acids in a 15-mer provides a peptide with an amino acid sequence which has a 93.33% (~93%), 86.67% (~87%), and 80.00% (80%) sequence identity, respectively, to the reference peptide amino acid sequence. Analogously, substitution of one, two, and three amino acids in a 14-mer provides a peptide with an amino acid sequence which has a 92.86% (~93%), 85.71% (~86%), and 78.57% (79%) sequence identity, respectively, to the reference peptide amino acid sequence. Analogously, substitution of one, two, and three amino acids in a 13-mer provides a peptide with an amino acid sequence which has a 92.31% (~92%), 84.62% (~85%), and 76.92% (~77%) sequence identity, respectively, to the reference peptide amino acid sequence. Analogously, substitution of one, two, and three amino acids in a 12-mer provides a peptide with an amino acid sequence which has a 91.67% (~92%), 83.33% (~83%), and 75.00% (75%) sequence identity, respectively, to the reference peptide amino acid sequence. Analogously, substitution of one and two amino acids in an 11-mer provides a peptide with an amino acid sequence which has a 90.91% (~91%) and 81.82% (~82%) sequence identity, respectively, to the reference peptide amino acid sequence. Analogously, substitution of one and two amino acids in a 10-mer provides a peptide with an amino acid sequence which has a 90.00% (90%) and 80.00% (80%) sequence identity, respectively, to the reference peptide amino acid sequence. Analogously, substitution of one and two amino acids in a 9-mer provides a peptide with an amino acid sequence which has a 88.89% (~89%) and 77.78% (~78%) sequence identity, respectively, to the reference peptide amino acid sequence. Analogously, substitution of one and two amino acids in an 8-mer provides a peptide with an amino acid sequence which has a 87.50% (~88%) and 75.00% (75%) sequence identity, respectively, to the reference peptide amino acid sequence. Analogously, substitution of one amino acid in a 7-mer, 6-mer, 5-mer, and 4-mer provides a peptide with an amino acid sequence which has a 85.71% (~86%), 83.33% (~83.3%), 80.00% (80%), and 75.00% (75%) sequence identity, respectively, to the reference peptide. Preferred amino acid sequences of this invention have greater than 80% sequence identity to the amino acid sequence in the reference sequence, more preferably between 81% and 96% sequence identity to the amino acid sequence in the reference sequence, and more preferably between 80% and 96% sequence identity to the amino acid sequence in the reference sequence. The preferred amino acid sequences can be optionally N-terminally chemically bonded at the terminal peptide amino group to a C2 to C22 linear aliphatic carboxylic acid moiety, more preferably to a C2 to C16 linear aliphatic carboxylic acid moiety, most preferably to a C2 or C16 linear aliphatic carboxylic acid moiety, by an amide bond, and optionally C-terminally chemically bonded at the terminal peptide carboxylic group to an amine such as ammonia or a primary or secondary amine such as a C1 to C16 linear aliphatic primary amine, by an amide bond.

Examples of substitution variants of peptide 79, a 12-mer, include, for example, peptide 238, where Q at position 3 in peptide 79 has been substituted by E in sequence 238; peptide 233, where A at position 2 in peptide 79 has been substituted by K in peptide 233; peptide 234, where A at position 8 in peptide 79 has been substituted by K in peptide 234; peptide 235, where A at positions 2 and 8 in peptide 79 have been substituted by K in peptide 235; peptide 237, where F at position 4 in peptide 79 has been substituted by A in peptide 237; peptide 239, where K at position 10 in peptide 79 has been substituted by A in peptide 239; peptide 240, where G at position 11 in peptide 79 has been substituted by A in peptide 240; and peptide 241, where E at position 12 in peptide 79 has been substituted by A in peptide 241.

Examples of substitution variants of peptide 106, a 10-mer, include, for example, peptide 236, where F at position 4 in peptide 106 has been substituted by A in peptide 236; peptide 242, where G at position 1 in peptide 106 has been substituted by A in peptide 242; peptide 243, where Q at position 3 in peptide 106 has been substituted by A in peptide 243; peptide 244, where S at position 5 in peptide 106 has been substituted by A in peptide 244; peptide 245, where K at position 6 in peptide 106 has been substituted by A in peptide 245; peptide 247, where T at position 7 in peptide 106 has been substituted by A in peptide 247; peptide 248, where K at position 10 in peptide 106 has been substituted by A in peptide 248; peptide 249, where K at positions 6 and 10 in peptide 106 have both been substituted, each by A, in peptide 249.

Examples of a substitution variant of peptide 137, an 8-mer, include for example, peptide 250, where F at position 4 in peptide 137 has been substituted by A in peptide 250.

Examples of a substitution variant of peptide 219, a 4-mer, include for example, peptide 251, where K at position 2 in peptide 219 has been substituted by A in peptide 251.

A substitution variant peptide such as described herein can be in the form of an isolated peptide or in the form of a chemically modified peptide such as, for example, an N-terminal amide such as a myristoyl amide, an acetyl amide, and the like as described herein, and such as, for example, a C-terminal amide such as an amide formed with ammonia, and such as both an N-terminal amide and a C-terminal amide.

When deletions are included in the amino acid sequences of the peptides of the invention with respect to the reference amino acid sequence, there is preferably at least 80% sequence identity between the amino acid sequence of the peptide to the reference amino acid sequence. Peptides having 5 to 23 amino acids and including one amino acid deletion with respect to the reference peptide will have between 80% to about 96% (i.e., ~95.7%) sequence identity to the reference amino acid sequence. Peptides having 10 to 23 amino acids and including one amino acid deletion with respect to the reference peptide will have between about 90% to about 96% (i.e., ~95.7%) sequence identity to the reference amino acid sequence. Peptides having 20 to 23 amino acids and including one amino acid deletion with respect to the reference peptide will have between 95% to about 96% (i.e., ~95.7%) sequence identity to the reference amino acid sequence. Peptides having 10 to 23 amino acids and including two amino acid deletions with respect to the reference peptide will have between about 80% to about 92% (i.e., ~91.3%) sequence identity to the reference amino acid sequence. Peptides having 16 to 23 amino acids and including two amino acid deletions with respect to the reference peptide will have between about 87.5% to about 92% (i.e., ~91.3%) sequence identity to the reference amino acid sequence. Peptides having 20 to 23 amino acids and including two amino acid deletions with respect to the reference peptide will have between about 90% to about 92% (i.e., ~91.3%) sequence identity to the reference amino acid sequence. Peptides having 15 to 23 amino acids and including three amino acid deletions with respect to the reference peptide will have between about 80% to about 87% sequence identity to the reference amino acid sequence. Peptides having 20 to 23 amino acids and including three amino acid deletions with respect to the reference peptide will have between about 85% to about 87% sequence identity to the reference amino acid sequence. Peptides having 20 to 23 amino and including four amino acid deletions with respect to the reference peptide will have between about 80% to about 83% (i.e., 82.6%) sequence identity to the reference amino acid sequence.

As stated above, one or more of the amino acids of the peptides may also be chemically modified. Any amino acid modifications known in the art may be made to the amino acids of the peptides using any method known in the art.

In some embodiments, the N-terminal and/or C-terminal amino acid may be modified. For example, the alpha-N-terminal amino acid of the peptides may be alkylated, amidated, or acylated at the alpha-N-terminal (N-terminal) amino (alpha-H2N—) group, and, for example, the C-terminal amino acid of the peptides may be amidated or esterified at the C-terminal carboxyl (—COOH) group. For example, the N-terminal amino group may be modified by acylation to include any acyl or fatty acyl group to form an amide, including an acetyl group (i.e., CH3-C(=O)— or a myristoyl group, both of which are currently preferred groups). In some embodiments, the N-terminal amino group may be modified to include an acyl group having formula —C(O)R, wherein R is a linear or branched alkyl group having from 1 to 15 carbon atoms, or may be modified to include an acyl group having formula —C(O)R1, wherein R1 is a linear alkyl group having from 1 to 15 carbon atoms. The N-amide can also be a formamide (R=H). The C-terminal amino acid of the peptides may also be chemically modified. For example, the C-terminal carboxyl group of the C-terminal amino acid may be chemically modified by conversion to a carboxamide group in place of the carboxyl group. (i.e., amidated). In some embodiments, the N-terminal and/or C-terminal amino acids are not chemically modified. In some embodiments, the N-terminal group is modified and the C-terminal group is not modified. In some embodiments, both the N-terminal and the C-terminal groups are modified.

The peptide may be acylated at the amino group of the N-terminal amino acid to form an N-terminal amide with an acid selected from the group consisting of:

(i-a) a C2 (acetyl) to C13 aliphatic (saturated or optionally unsaturated) carboxylic acid (for example, an N-terminal amide with acetic acid (which is a preferred group), with propanoic acid, with butanoic acid, with hexanoic acid, with octanoic acid, with decanoic acid, with dodecanoic acid) which may be linear, branched (greater than C3), or comprise a ring (greater than C3);

(i-b) a saturated C14 aliphatic carboxylic acid, which may be linear, branched or comprise a ring;

(i-c) an unsaturated C14 aliphatic carboxylic acid, which may be linear, branched or comprise a ring;

(i-d) C15 to C24 aliphatic (saturated or optionally unsaturated) carboxylic acid, which may be linear, branched or comprise a ring (for example, with tetradecanoic acid (myristic acid which is a preferred group), with hexadecanoic acid, with 9-hexadecenoic acid, with octadecanoic acid, with 9-octadecenoic acid, with 11-octadecenoic acid, with 9,12-octadecadienoic acid, with 9,12,15-octadecatrienoic acid, with 6,9,12-octadecatrienoic acid, with eicosanoic acid, with 9-eicosenoic acid, with 5,8,11,14-eicosatetraenoic acid, with 5,8,11,14,17-eicosapentaenoic acid, with docosanoic acid, with 13-docosenoic acid, with 4,7,10,13,16,19-docosahexaenoic acid, with tetracosanoic acid, and the like);

(ii) trifluoroacetic acid;

(iii) benzoic acid; and (iv-a) a C1 to C12 aliphatic alkyl sulfonic acid which forms an aliphatic alkyl sulfonamide, wherein the C1 to C12 aliphatic alkyl carbon chain structure of the sulfonic acid is analogous to that of the aliphatic alkyl carboxylic acid chains in the aliphatic alkyl carboxylic acids described above. For example, a peptide may be acylated using a carboxylic acid group represented as (C1-C11)-alkyl-C(O)OH through dehydrative coupling by way of activation of the carboxylic acid group to form an amide represented as (C1-C11-alkyl-C(O)—NH-peptide. Analogously, a sulfonamide may be formed by reacting a sulfonic acid species (represented as (C1-C12)-alkyl-S(O2)-X, e.g., where X is halogen or OCH3 or other compatible leaving group) with an N-terminal amino group to form a sulfonamide represented as (C1-C12)-alkyl-S(O2)-NH-peptide.

(iv-b) a C14 to C24 aliphatic alkyl sulfonic acid which forms an aliphatic alkyl sulfonamide, wherein the C14 to C24 aliphatic alkyl carbon chain structure of the sulfonic acid is analogous to that of the aliphatic alkyl carboxylic acid chains in the aliphatic alkyl carboxylic acids described above . . . . For example, a peptide may be acylated using a carboxylic acid group represented as (C13-C23)-alkyl-C(O)OH through dehydrative coupling by way of activation of the carboxylic acid group to form an amide represented as (C13-C23)-alkyl-C(O)—NH-peptide. Analogously, a sulfonamide may be formed by reacting a sulfonic acid species (represented as (C14-C24)-alkyl-S(O2)-X, e.g., where X is halogen or OCH3 or other compatible leaving group) with an N-terminal amino group to form a sulfonamide represented as (C14-C24)-alkyl-S(O2)-NH-peptide.

As another example, the N-terminal amino group of the N-terminal amino acid may be alkylated with a C1 to C12 aliphatic alkyl group, the structure of which aliphatic alkyl group is as described above. Alkylation may be effected, for example, using an aliphatic alkyl halide or an aliphatic alkyl sulfonic acid ester (mesylate, tosylate, etc.), preferably using a primary alkyl halide or a primary alkyl sulfonic acid ester. The N-terminal amino acid may be also modified at the terminal amino to include any acyl or aliphatic acyl fatty acyl group as an amide, including an acetyl group (i.e., —C(O)CH3, which is a preferred group), a myristoyl group (which is a preferred group), a butanoyl group, a hexanoyl group, a octanoyl group, a decanoyl group, a dodecanoyl group, a tetradecanoyl group, a hexadecanoyl group, a 9-hexadecenoyl group, a octadecanoyl group, a 9-octadecenoyl group, a 11-octadecenoyl group, a 9,12-octadecadienoyl group, a 9,12,15-octadecatrienoyl group, a 6,9,12-octadecatrienoyl group, a eicosanoyl group, a 9-eicosenoyl group, a 5,8,11,14-eicosatetraenoyl group, a 5,8,11,14,17-eicosapentaenoyl group, a docosanoyl group, a 13-docosenoyl group, a 4,7,10,13,16,19-docosahexaenoyl group, a tetracosanyl group, which groups are covalently attached to the terminal amino group of the peptide by an amide bond.

The C-terminal carboxylic acid group of the C-terminal amino acid of the peptides of the invention may also be chemically modified. For example, the C-terminal amino acid may be chemically modified by reaction of the C-terminal carboxylic acid group of the peptide with an amine to form an amide group such as an amide of ammonia which is a preferred group; an amide of a C1 to C12 aliphatic alkyl amine, preferably a linear aliphatic alkyl amine; an amide of a hydroxyl-substituted C2 to C12 aliphatic alkyl amine; an amide of a linear 2-(C1 to C12 aliphatic alkyl)oxyethylamine group; and an amide of an omega-methoxy-poly(ethyleneoxy)n-ethylamine group (also referred to as an omega-methoxy-PEG-alpha-amine group or an omega-methoxy-(polyethylene glycol)amine group), where n is from 0 to 10. The C-terminal carboxylic acid group of the C-terminal amino acid of the peptide may also be in the form of an ester selected from the group consisting of an ester of a C1 to C12 aliphatic alkyl alcohol and an ester of a 2-(omega-methoxy-poly(ethyleneoxy)n)-ethanol (MPEG) group, where n is from 0 to 10. In one aspect, a polyethylene glycol component such as in a PEG ester, an MPEG ester, a PEG amide, an MPEG amide and the like preferably has a molecular weight of from about 500 to 40,000 Daltons, more preferably from 1000 to 25,000 Daltons, and most preferably from about 1000 to about 10,000 Daltons.

The C-terminal carboxylic acid group on the peptide, which may be represented by the formula peptide-C(O)OH, may also be amidated by conversion to an activated form such as a carboxylic acid halide, carboxylic acid anhydride, N-hydroxysuccinimide ester, pentafluorophenyl (OPfp) ester, 3-hydroxy-2,3-dihydro-4-oxo-benzo-triazone (ODhbt) ester, and the like to facilitate reaction with ammonia or a primary or secondary amine, preferably ammonia or a primary amine, and preferably while any other reactive groups in the peptide are protected by synthetic chemically compatible protecting groups well known in the art of peptide synthesis, especially of peptide solid phase synthesis, such as a benzyl ester, a t-butyl ester, a phenyl ester, etc. A resulting peptide amide could be represented by the formula peptide-C(O)—NR3R4 (the amide being at the C-terminal end of the peptide) wherein R3 and R4 are independently selected from the group consisting of hydrogen; C1 to C12 alkyl such as methyl, ethyl, butyl, isobutyl, cyclopropylmethyl, hexyl, dodecyl, and optionally higher e.g., from C14 to C24 such as tetradecyl, and the like as described above.

The C-terminal carboxylic acid of the C-terminal amino acid may also be converted to an amide of a hydroxyl-substituted C2 to C12 aliphatic alkyl amine (the hydroxyl group being attached to a carbon atom rather than a nitrogen atom of the amine) such as 2-hydroxyethylamine, 4-hydroxybutylamine, and 12-hydroxydodecylamine, and the like.

The C-terminal carboxylic acid may also be converted to an amide of a hydroxyl-substituted C2 to C12 aliphatic alkyl amine, wherein the hydroxyl group can be acylated to form an ester with a C2 to C12 aliphatic carboxylic acid as described above. Preferably, in the peptide amide at the C-terminal end of the peptide represented by the formula peptide-C(O)

NR5R6, R5 is hydrogen and R6 is selected from the group consisting of hydrogen, C1 to C12 alkyl, and hydroxyl-substituted C2 to C12 alkyl.

The C-terminal carboxylic acid of the C-terminal amino acid may be converted to an amide of a linear 2-(C1 to C12 aliphatic alkyl)oxyethylamine. Such an amide may be prepared, for example, by reaction of a linear C1 to C12 aliphatic alcohol with potassium hydride in diglyme with 2-chloroethanol to provide a linear C1 to C12 aliphatic alkyl ethanol, which can be converted to an amine by oxidation to an aldehyde, followed by reductive amination to an amine (for example using ammonia), or by conversion to an alkyl halide (e.g. using thionyl chloride) followed by treatment with an amine such as ammonia.

The C-terminal carboxylic acid of the C-terminal amino acid may be converted to an amide of a linear PEG-amine (e.g., omega-hydroxy-PEG-alpha-amine; omega-(C1-to-C12)-PEG-alpha-amine such as omega-methoxy-PEG-alpha-amine, i.e., MPEG-amine). In one aspect, the polyethylene glycol or PEG component preferably has a molecular weight of from about 500 to 40,000 Daltons, more preferably from 1000 to 25,000 Daltons, and most preferably from about 1000 to about 10,000 Daltons.

The C-terminal carboxylic acid of the C-terminal amino acid may also be converted to an amide of an omega-methoxy-poly(ethyleneoxy)n-ethylamine, where n is from 0 to 10, which can be prepared from the corresponding omega-methoxy-poly(ethyleneoxy)n-ethanol, for example, by conversion of the alcohol to an amine as described above.

In another embodiment, the C-terminal carboxyl may be converted to an amide represented by the formula peptide-C(O)—NR7R8, wherein R7 is hydrogen and R8 is a linear 2-(C1 to C12 aliphatic alkyl)oxyethyl group wherein the C1 to C12 aliphatic alkyl portion is as described above and includes groups such as methoxyethyl (i.e., CH3O—CH2CH2-), 2-dodecyloxyethyl, and the like; or R7 is hydrogen and R8 is an omega-methoxy-poly(ethyleneoxy)n-ethyl group where the n of the poly(ethyleneoxy) portion is from 0 to 10, such as 2-methoxyethyl (i.e., CH3O—CH2CH2-), omega-methoxyethoxyethyl (i.e., CH3O—CH2CH$_2$O—CH2CH2-) up to CH3O—(CH2CH2O)10-CH2CH2-.

The C-terminal carboxylic acid group of the C-terminal amino acid of the peptide may also be in the form of an ester of a C1 to C12 aliphatic alkyl alcohol, the aliphatic alkyl portion of the alcohol as described above. The C-terminal carboxylic acid group of the C-terminal amino acid of the peptide may also be in the form of an ester of a 2-(omega-methoxy-poly(ethyleneoxy)n)-ethanol group where n is from 0 to 10, which can be prepared from reaction of 2-methoxyethanol as a sodium 2-methoxyethanolate with stoichiometric amounts of ethylene oxide, the stoichiometric amount dependent on the size of n.

A side chain in an amino acid of the peptides may also be chemically modified. For example, a phenyl group in phenylalanine or tyrosine may be substituted with a substituent selected from the group consisting of:

a C1 to C24 aliphatic alkyl group (i.e., linear or branched, and/or saturated or unsaturated, and/or containing a cyclic group) such as methyl (preferred), ethyl, propyl, isopropyl, butyl, isobutyl, cyclopropyl, 2-methylcyclopropyl, cyclohexyl, octyl, decyl, dodecyl, hexadecyl, octadecyl, eicosanyl, docosanyl, tetracosanyl, 9-hexadecenyl, 9-octadecenyl, 11-octadecenyl, 9,12-octadecadienyl, 9,12,15-octadecatrienyl, 6,9,12-octadecatrienyl, 9-eicosenyl, 5,8,11,14-eicosatetraenyl, 5,8,11,14,17-eicosapentaenyl, 13-docosenoyl, and 4,7,10,13,16,19-docosahexaenyl;

a C1 to C12 aliphatic alkyl group substituted with a hydroxyl group at least one carbon atom away from a site of unsaturation, examples of which hydroxyalkyl group include hydroxymethyl, hydroxyethyl, hydroxydodecyl, and the like;

a C1 to C12 alkyl group substituted with a hydroxyl group that is esterified with a C2 to C25 aliphatic carboxyl group of an acid such as acetic acid, butanoic acid, hexanoic acid, octanoic acid, decanoic acid, dodecanoic acid, tetradecanoic acid, hexadecanoic acid, 9-hexadecenoic acid, octadecanoic acid, 9-octadecenoic acid, 11-octadecenoic acid, 9,12-octadecadienoic acid, 9,12,15-octadecatrienoic acid, 6,9,12-octadecatrienoic acid, eicosanoic acid, 9-eicosenoic acid, 5,8,11,14-eicosatetraenoic acid, 5,8,11,14,17-eicosapentaenoic acid, docosanoic acid, 13-docosenoic acid, 4,7,10,13,16,19-docosahexaenoic acid, tetracosanoic acid, and the like, a dicarboxylic acid such as succinic acid, or a hydroxyacid such as lactic acid, wherein the total number of carbon atoms of the ester substituent is between 3 and 25;

halogen such as fluoro-, chloro-, bromo-, and iodo-; nitro-; amino—such as NH2, methyl amino, dimethylamino; trifluoromethyl-;

carboxyl (—COOH);

a C1 to C24 alkoxy (such as can be formed by alkylation of tyrosine) such as methoxy, ethoxy, propyloxy, isopropyloxy, butyloxy, isobutyloxy, cyclopropyloxy, 2-methoxycyclopropyloxy, cyclohexyloxy, octyloxy, decyloxy, dodecyloxy, hexadecyloxy, octadecyloxy, eicosanyloxy, docosanyloxy, tetracosanyloxy, 9-hexadecenyloxy, 9-octadecenyloxy, 1'-octadecenyloxy, 9,12-octadecadienyloxy, 9,12,15-octadecatrienyloxy, 6,9,12-octadecatrienyloxy, 9-eicosenyloxy, 5,8,11,14-eicosatetraenyloxy, 5,8,11,14,17-eicosapentaenyloxy, 13-docosenyloxy, and 4,7,10,13,16,19-docosahexaenyloxy; and a C2 to C12 hydroxyalkyloxy such as 2-hydroxyethyloxy and esters thereof with carboxylic acids as described above or with trifluoroacetic acid.

A serine hydroxyl group may be esterified with a substituent selected from the group consisting of:

a C2 to C12 aliphatic carboxylic acid group such as described above;

a trifluoroacetic acid group; and a benzoic acid group.

The epsilon amino group in lysine may be chemically modified, for example, by amide formation with: a C2 to C12 aliphatic carboxylic acid group (for example, by reaction of the amine with a chemically activated form of a carboxylic acid such as an acid chloride, an anhydride, an N-hydroxysuccinimide ester, a pentafluorophenyl (OPfp) ester, a 3-hydroxy-2,3-dihydro-4-oxo-benzo-triazone (ODhbt) ester, and the like) such as described above, or a benzoic acid group, or an amino acid group. Additionally, the epsilon amino group in lysine may be chemically modified by alkylation with one or two C1 to C4 aliphatic alkyl groups.

The carboxylic acid group in glutamic acid may be modified by formation of an amide with an amine such as: ammonia; a C1 to C12 primary aliphatic alkyl amine (the alkyl portion of which is as described above) including with methylamine; or an amino group of an amino acid.

The carboxylic acid group in glutamic acid may be modified by formation of an ester with a C1 to C12 aliphatic hydroxyalkyl group as described above, preferably an ester with a primary alcohol of a C1 to C12 aliphatic alkyl such as methanol, ethanol, propan-1-ol, n-dodecanol, and the like as described above.

In a preferred embodiment, the present invention comprises a method of inhibiting the release of at least one inflammatory mediator from a granule in at least one inflammatory cell in a tissue and/or fluid of a subject comprising administration to said tissue and/or fluid a therapeutically effective amount of a pharmaceutical composition comprising at least one peptide having an amino acid sequence selected from the group consisting of:

(a) an amino acid sequence having from 4 to 23 contiguous amino acids of a reference sequence, GAQFSKTAAKGEAAAERPGEAAVA (SEQ ID NO. 1);

(b) an amino acid sequence having the sequence, GAQFSKTAAKGEAAAERPGEAAVA (SEQ ID NO. 1); and (c) an amino acid sequence substantially identical to the sequence defined in (a), wherein the C-terminal amino acid of the peptide is optionally independently chemically modified, and the N-terminal amino acid of the peptide is independently chemically modified by acylation with a carboxylic acid selected from the group consisting of a C2 to C13 saturated or unsaturated aliphatic carboxylic acid, a C14 saturated (myristic acid) or unsaturated aliphatic carboxylic acid, a C15 to C24 saturated or unsaturated aliphatic carboxylic acid, and trifluoroacetic acid, or is not chemically modified, with the proviso that said peptide can be modified by acylation when its amino acid sequence begins with the sequence GAQF of the reference sequence by acylation only with a carboxylic acid selected from the group consisting of a C2 to C13 saturated or unsaturated aliphatic carboxylic acid, a C14 unsaturated aliphatic carboxylic acid, a C15 to C24 saturated or unsaturated aliphatic carboxylic acid, and trifluoroacetic acid, or is not chemically modified, wherein said peptide, optionally combined with a pharmaceutically acceptable carrier, and in a therapeutically effective inflammatory mediator release-reducing amount to reduce the release of said inflammatory mediator from at least one inflammatory cell as compared to release of said inflammatory mediator from at least one of the same type of inflammatory cell that would occur in the absence of said at least one peptide.

The method preferably employs a peptide that can be acetylated at the alpha N-terminal amino acid. This peptide can consist of at least ten contiguous amino acid residues and is preferably embodied by acetyl-peptide 106 (SEQ ID NO: 106).

The method also employs a peptide consisting of at least four contiguous amino acid residues and more preferably at least six contiguous amino acid residues. Further, the peptide can be myristoylated at the alpha N-terminal amino acid when the peptide. The method also can utilized peptide that can be amidated with ammonia at the alpha C-terminal amino acid.

The method in a further embodiment utilizes a peptide comprises an amino acid sequence of (a) an amino acid sequence having from 4 to 23 contiguous amino acids of a reference sequence, GAQFSKTAAKGEAAAERPGEAAVA (SEQ ID NO. 1), wherein the N-terminal amino acid of the amino acid sequence of (a) is selected from amino acid position 2 to 21 of the reference sequence, GAQFSKTAAKGEAAAERPGEAAVA (SEQ ID NO. 1). Further, these peptides can be myristoylated at the alpha N-terminal amino acid and also can be amidated with ammonia at the alpha C-terminal amino acid.

The method of administration according to the present invention defines the reduction of the release of an inflammatory mediator as blocking or inhibiting the mechanism that releases an inflammatory mediator from the inflammatory cell in said subject.

The method of administration includes incorporating or mixing the disclosed peptides with a pharmaceutically acceptable carrier to form a pharmaceutical composition.

The method of administration of the present invention release of at least one inflammatory mediator release-reducing amount to reduce the release of said inflammatory mediator from at least one inflammatory cell as compared to release of said inflammatory mediator from at least one of the same type of inflammatory cell that would occur in the absence of said at least one peptide. The inflammatory cell in said subject can be a leukocyte, a granulocyte, a basophil, an eosinophil, monocyte, macrophage or a combination thereof.

The inflammatory mediator released from at least one granule of at least one inflammatory cell is selected from the group consisting of myeloperoxidase (MPO), eosinophil peroxidase (EPO), major basic protein [MBP], lysozyme, granzyme, histamine, proteoglycan, protease, a chemotactic factor, cytokine, a metabolite of arachidonic acid, defensin, bactericidal permeability-increasing protein (BPI), elastase, cathepsin G, cathepsin B, cathepsin D, beta-D-glucuronidase, alpha-mannosidase, phospholipase $A_2$, chondroitin-4-sulphate, proteinase 3, lactoferrin, collagenase, complement activator, complement receptor, N-formylmethionyl-leucylphenylalanine (FMLP) receptor, laminin receptor, cytochrome $b_{558}$, monocyte-chemotactic factor, histaminase, vitamin B12 binding protein, gelatinase, plasminogen activator, beta-D-glucuronidase, and a combination thereof. Preferably the inflammatory mediator is selected from the group consisting of myeloperoxidase (MPO), eosinophil peroxidase (EPO), major basic protein (MBP), lysozyme, granzyme and a combination thereof.

The method according to claim 13, wherein said effective inflammatory mediator release-reducing amount of said peptide comprises a degranulation-inhibiting amount of peptide that reduces the amount of an inflammatory mediator released from at least one inflammatory cell from about 1% to about 99% or preferably about 5-50% to about 99%, as compared to the amount released from at least one inflammatory cell in the absence of the peptide.

The method of the present invention is useful for the treatment of a subject afflicted by or suffering from a respiratory disease. This respiratory disease may be asthma, chronic bronchitis, chronic obstructive pulmonary disease (COPD) and cystic fibrosis. The subjects that can be treated by the present invention are preferably mammals, such as humans, canines, equines and felines.

The method of administration of the peptides of the present invention are by topical administration, parenteral administration, rectal administration, pulmonary administration, nasal administration, and oral administration. More preferably, the pulmonary administration comprises an aerosol, which can be generated from a dry powder inhaler, a metered dose inhaler or nebulizer. Additionally, the administration to the subject can further include the administration of a second molecule selected from the group consisting of an antibiotic, an antiviral compound, an antiparasitic compound, an anti-inflammatory compound, and an immunomodulator.

The method is also useful for the treatment of a subject who is afflicted by or suffering from a disease selected from the group consisting of a bowel disease, a skin disease, an autoimmune disease, a pain syndrome, and combinations thereof. More specifically, the bowel disease is selected from the group consisting of ulcerative colitis, Crohn's disease and irritable bowel syndrome. Skin diseases also treatable by the present method includes rosacea, eczema, psoriasis and severe acne. Additionally a subject suffering from arthritis may also be treated by the present invention.

The present invention in one embodiment encompasses the administration of peptides comprising an amino acid sequence substantially identical to the amino acid sequence of (a) having from 4 to 23 contiguous amino acids of a reference sequence, GAQFSKTAAKGEAAAERPGEAAVA (SEQ ID NO. 1). These peptides preferably are selected from the group consisting of SEQ ID NOS: 233, 234, 235, 236, 237, 238, 239, 240, 241, 242, 243, 244, 245, 247, 248, 249, 250, 251 and 252. These peptides can be further acetylated at the alpha N-terminal amino acid or myristoylated at the alpha N-terminal amino acid and optionally amidated with ammonia at the alpha C-terminal amino acid.

The method of the present invention also is useful for reducing mucus hypersecretion in a subject by the administration of the peptides of the present invention as described herein for also reducing MARCKS-related mucus hypersecretion from at least one mucus secreting cell or tissue in the subject, whereby mucus hypersecretion in the subject is reduced compared to that which would occur in the absence of said administration of said peptide.

The present invention is directed to an isolated peptide having an amino acid sequence selected from the group consisting of:

(a) an amino acid sequence having from 4 to 23 contiguous amino acids of a reference sequence, GAQFSKTAAKGEAAAERPGEAAVA (SEQ ID NO. 1);

(b) an amino acid sequence having the sequence, GAQFSKTAAKGEAAAERPGEAAVA (SEQ ID NO. 1); and (c) an amino acid sequence substantially identical to the sequence defined in (a), wherein the C-terminal amino acid of the peptide is optionally independently chemically modified, and the N-terminal amino acid of the peptide is independently chemically modified by acylation with a carboxylic acid selected from the group consisting of a C2 to C13 saturated or unsaturated aliphatic carboxylic acid, a C14 saturated or unsaturated aliphatic carboxylic acid, a C15 to C24 saturated or unsaturated aliphatic carboxylic acid, and trifluoroacetic acid, or is not chemically modified, with the proviso that said peptide is modified by acylation when its amino acid sequence begins with the sequence GAQF of the reference sequence by acylation only with a carboxylic acid selected from the group consisting of a C2 to C13 saturated or unsaturated aliphatic carboxylic acid, a C14 unsaturated aliphatic carboxylic acid, a C15 to C24 saturated or unsaturated aliphatic carboxylic acid, and trifluoroacetic acid, or is not chemically modified, wherein said peptide, optionally combined with a pharmaceutically acceptable carrier, and in a therapeutically effective inflammatory mediator release-reducing amount to reduce the release of said inflammatory mediator from at least one inflammatory cell as compared to release of said inflammatory mediator from at least one of the same type of inflammatory cell that would occur in the absence of said at least one peptide.

The isolated peptide can be acetylated at the alpha N-terminal amino acid. The isolated peptide consists of at least ten contiguous amino acid residues and preferably is an isolated peptide consists of acetyl-peptide 106 (SEQ ID NO: 106).

In a further embodiment, the peptide consists of at least four contiguous amino acid residues or peptide consists of at least six contiguous amino acid residues.

The peptide can also be myristoylated at the alpha N-terminal amino acid and/or peptide can be amidated with ammonia at the alpha C-terminal amino acid.

The isolated peptide can further comprise an amino acid sequence of (a) described above, (a) an amino acid sequence having from 4 to 23 contiguous amino acids of a reference sequence, GAQFSKTAAKGEAAAERPGEAAVA (SEQ ID NO. 1); wherein the N-terminal amino acid of the amino acid sequence of (a) is selected from amino acid position 2 to 21 of the reference sequence, GAQFSKTAAKGEAAAERPGEAAVA (SEQ ID NO. 1). This peptide can be further myristoylated or acetylated at the alpha N-terminal amino acid or optionally amidated with ammonia at the alpha C-terminal amino acid.

The isolated peptide in a further embodiment, wherein the amino acid sequence is substantially identical to the amino acid sequence of (a) having from 4 to 23 contiguous amino acids of a reference sequence, GAQFSKTAAKGEAAAERPGEAAVA (SEQ ID NO. 1). These peptides preferably are selected from the group consisting of SEQ ID NOS: 233, 234, 235, 236, 237, 238, 239, 240, 241, 242, 243, 244, 245, 247, 248, 249, 250, 251 and 252. These peptides can be further acetylated at the alpha N-terminal amino acid or myristoylated at the alpha N-terminal amino acid and optionally amidated with ammonia at the alpha C-terminal amino acid. amino acid sequence of (c) substantially identical to the amino acid sequence of (a) is selected from the group consisting of SEQ ID NOS: 233, 234, 235, 236, 237, 238, 239, 240, 241, 242, 243, 244, 245, 247, 248, 249, 250, 251 and 252.

The invention also encompasses a composition comprising an isolated peptide as described in the paragraphs above and described herein and an excipient. The invention also encompasses a pharmaceutical composition comprising an isolated peptide an isolated peptide as described in the paragraphs above and described herein and a pharmaceutically acceptable carrier. The pharmaceutical composition can further preferably be sterile, sterilizable or sterilized. These peptides can be contained in a kit with reagents useful for administration.

DETAILED DESCRIPTION OF THE INVENTION

Figure 1A:
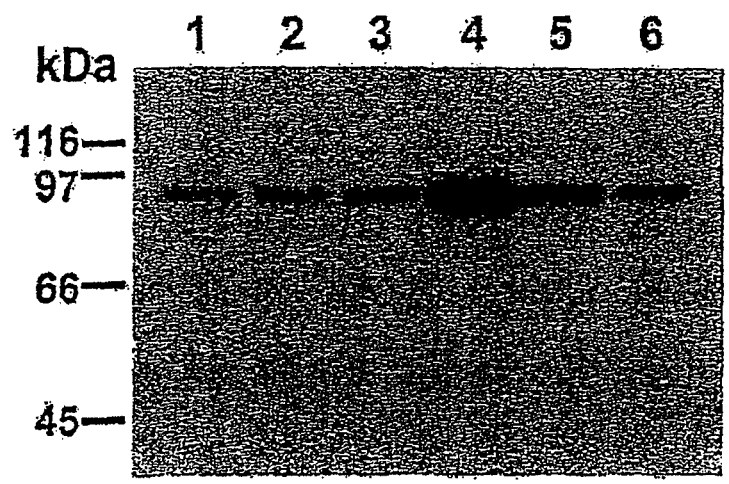
FIGS. 1A-1B illustrate that PKC-dependent phosphorylation releases MARCKS from the plasma membrane to the cytoplasm.

The present invention will now be described more fully hereinafter with reference to the accompanying figures, in which preferred embodiments of the invention are illustrated. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. The use of the words "a" or "an" herein to describe any aspect of the present invention is to be interpreted as indicating one or more.

The present invention is directed to a method of inhibiting the exocytotic release of at least one inflammatory mediator from at least one inflammatory cell comprising contacting the at least one inflammatory cell, which cell comprises at least one inflammatory mediator contained within a vesicle inside the cell, with at least one peptide selected from the group consisting of a MANS peptide and an active fragment thereof in an effective amount to reduce the release of the inflammatory mediator from the inflammatory cell as compared to the release of the inflammatory mediator from the same type of inflammatory cell that would occur in the absence of the at least one peptide.

The present invention is further directed to a method of inhibiting the release of at least one inflammatory mediator from at least one inflammatory cell in a tissue or fluid of a subject comprising the administration to the subject's tissue and/or fluid, which comprises at least one inflammatory cell comprising at least one inflammatory mediator contained within a vesicle inside the cell, a therapeutically effective amount of a pharmaceutical composition comprising at least one peptide selected from the group consisting of a MANS peptide and an active fragment thereof in a therapeutically effective amount to reduce the release of the inflammatory mediator from at least one inflammatory cell as compared to release of the inflammatory mediator from at least one of the same type of inflammatory cell that would occur in the absence of the at least one peptide. More specifically, reducing the release of an inflammatory mediator comprises blocking or inhibiting the mechanism that releases an inflammatory mediator from the inflammatory cell.

The present invention is directed to the contact and/or administration of the peptide described above and throughout the specification with any known inflammatory cell that may be contained in the tissue or fluid of a subject which contains at least one inflammatory mediator contained within a vesicle inside the cell. The inflammatory cell is preferably a leukocyte, more preferably a granulocyte, which can be further classified as a neutrophil, a basophil, an eosinophil or a combination thereof. The inflammatory cells contacted in the present method may also be a monocyte/macrophage.

The present invention is directed to reducing the release of inflammatory mediators contained within the vesicles of inflammatory cells and these inflammatory mediators are selected from the group consisting of myeloperoxidase (MPO), eosinophil peroxidase (EPO), major basic protein (MBP), lysozyme, granzyme, histamine, proteoglycan, protease, a chemotactic factor, cytokine, a metabolite of arachidonic acid, defensin, bactericidal permeability-increasing protein (BPI), elastase, cathepsin G, cathepsin B, cathepsin D, beta-D-glucuronidase, alpha-mannosidase, phospholipase $A_2$, chondroitin-4-sulphate, proteinase 3, lactoferrin, collagenase, complement activator, complement receptor, N-formylmethionyl-leucyl-phenylalanine (FMLP) receptor, laminin receptor, cytochrome $b_{558}$, monocyte-chemotactic factor, histaminase, vitamin B12 binding protein, gelatinase, plasminogen activator, beta-D-glucuronidase, and a combination thereof. Preferably, these inflammatory mediators are selected from the group consisting of myeloperoxidase (MPO), eosinophil peroxidase (EPO), major basic protein (MBP), lysozyme, granzyme and a combination thereof.

The present invention contacts an effective amount of the peptide with an inflammatory cell, wherein the effective amount is defined as a degranulation-inhibiting amount of MANS peptide or an active fragment thereof that reduces the amount of an inflammatory mediator released from at least one inflammatory cell from about 1% to about 99% as compared to the amount released from at least one inflammatory cell in the absence of MANS peptide or an active fragment thereof. This amount is also known as an effective inflammatory mediator release-reducing amount. More preferably, this effective amount of the contacted peptide comprises a degranulation-inhibiting amount of MANS peptide or an active fragment thereof that reduces the amount of an inflammatory mediator released from at least one inflammatory cell from between about 5-50% to about 99% as compared to the amount released from at least one inflammatory cell in the absence of MANS peptide or an active fragment thereof.

The present invention in one embodiment is directed to the administration of at least one peptide comprising a MANS peptide and an active fragment thereof in a therapeutically effective amount into tissue or fluid of a subject where the subject is afflicted by a respiratory disease, which is preferably asthma, chronic bronchitis or COPD. In a further embodiment, the subject may be afflicted by a bowel disease, a skin disease, an autoimmune disease, a pain syndrome, and combinations thereof. The bowel disease may be ulcerative colitis, Crohn's disease or irritable bowel syndrome. The subject may be afflicted with a skin disease, such as rosacea, eczema, psoriasis or severe acne. The subject may also be afflicted with arthritis, such as rheumatoid arthritis, psoriatic arthritis, systemic lupus erythematosus. Subjects afflicted by cystic fibrosis may also be treated by the present method and peptides. The present method is preferably useful for the treatment of subjects, such as mammals, and preferably humans, canines, equines and felines.

The present method of treatment of subjects is by the administration of one or more peptides including the MANS peptide or an active fragment described herein to include topical administration, parenteral administration, rectal administration, pulmonary administration, nasal administration, or oral administration. More specifically, pulmonary administration is selected from the group of aerosol, dry powder inhaler, metered dose inhaler, and nebulizer. Additionally, the disclosed method may further comprise the administration to the subject of a second molecule selected from the group consisting of an antibiotic, an antiviral compound, an antiparasitic compound, an anti-inflammatory compound, and an immunomodulator.

In one aspect, the invention relates to a method of administering a pharmaceutical composition. The pharmaceutical composition comprises a therapeutically effective amount of a known compound and a pharmaceutically acceptable carrier. A "therapeutically effective" amount as used herein is an amount of a compound that is sufficient to ameliorate symptoms exhibited by a subject. The therapeutically effective amount will vary with the age and physical condition of the patient, the severity of the condition of the patient being treated, the duration of the treatment, the nature of any concurrent treatment, the pharmaceutically acceptable carrier used and like factors within the knowledge and expertise of those skilled in the art. Pharmaceutically acceptable carriers are preferably solid dosage forms such as tablets or capsules. Liquid preparations for oral administration also may be used and may be prepared in the form of syrups or suspensions, e.g., solutions containing an active ingredient, sugar, and a mixture of ethanol, water, glycerol, and propylene glycol. If desired, such liquid preparations may include one or more of following: coloring agents, flavoring agents, and saccharin. Additionally, thickening agents such as carboxymethylcellulose also may be used as well as other acceptable carriers, the selection of which are known in the art.

As stated above, the present invention relates to methods for regulating cellular secretory processes, especially those releasing inflammatory mediators from inflammatory cells. As used herein, the term "regulating" means blocking, inhibiting, decreasing, reducing, increasing, enhancing or stimulating. A number of cellular secretory processes involve the release of contents from membrane-bound vesicles or granules within cells A membrane-bound vesicle or granule is defined as an intracellular particle, which is primarily vesicular (or a vesicle inside a cell) and which contains stored material that can be secreted. Some of the contents of these vesicles, such as those contained in inflammatory cells, have been found to be responsible for a variety of pathologies in numerous mammalian tissues. Some of the effects of these secretions appear to include damage of previously healthy tissue during inflammation. This invention provides a means of blocking secretion from any membrane-bound vesicle, including those found in inflammatory cells, by targeting a specific molecule important in the intracellular secretory pathway with a synthetic peptide. This approach may be of therapeutic importance for the treatment of a wide variety of hypersecretory and inflammatory conditions in humans and animals.

More specifically, the present invention targets inflammatory cells that contain the inflammatory mediators in one or more granules or vesicles within the cells' cytoplasm. The cells are contacted with one or more peptides that are selected from the MANS peptide or an active fragment thereof, all of which are described in detail herein. Preferably the contact of the peptide with the inflammatory cell is via administration to a subject afflicted by or suffering from a disease in which these inflammatory cells are present in specific tissue or fluid within the tissue. Upon administration or contact of the peptide with the cell, the peptide competitively competes for and competitively inhibits the binding of the native MARCKS protein to the membrane of the intracellular granules or vesicles which contain the inflammatory mediators. As a result of blocking the binding of the MARCKS protein to the vesicles in the inflammatory cells, these vesicles in these cells do not move to the plasma membrane of the cells as they would normally do when stimulated to exocytotically release their contents of inflammatory mediators out of the cells. Thus, the method of the present invention inhibits the movement of the vesicles to the cells' plasma membrane, which in turn, reduces the release of the inflammatory mediators from the inflammatory cells. The amount of inflammatory mediators released from the cells over time is reduced because both the rate of release and the amount of release of the mediators from the inflammatory cells is dependent upon the concentration of the peptide administered and contacted with the inflammatory cells.

One benefit of the present invention is that it may combine a therapy that includes the direct blocking of mucus secretion with a unique anti-inflammatory therapy. A benefit of the present invention over current anti-inflammation therapies that affect a general suppression of the immune system is that the peptide is thought to block secretion of only intracellular components secreted from inflammatory cells. Thus, many aspects of the immune system should still function even with the inhibition of the inflammatory mediators.

The compounds of the invention may regulate, i.e. block, inflammatory mediator release from cells. This inhibition of release of inflammatory mediators is an attractive means for preventing and treating a variety of disorders, e.g., diseases and pathological conditions involving inflammation. Thus, the compounds of the invention may be useful for the treatment of such conditions. These encompass airway diseases and chronic inflammatory diseases including, but not limited to, osteoarthritis, multiple sclerosis, Guillain-Barre syndrome, Crohn's disease, ulcerative colitis, psoriasis, graft versus host disease and systemic lupus erythematosus. The compounds of the invention can also be used to treat other disorders associated with the activity of elevated levels of proinflammatory mediators and enzymes such as responses to various infectious agents and a number of diseases of autoimmunity such as rheumatoid arthritis, toxic shock syndrome, diabetes and inflammatory bowel diseases.

Uses of the peptide and methods of the invention include therapies to combat inflammation along with therapies that will combine the anti-inflammatory activity of the peptide with its ability to block mucus secretion. Diseases that may be treated by the peptide's ability to block both inflammation and mucus secretion include but are not limited to inflammatory bowel diseases, digestive disorders (i.e., inflamed gall bladder, Menetier's disease) and inflammatory airway diseases.

Other proinflammatory mediators have been correlated with a variety of disease states that correlate with influx of neutrophils into sites of inflammation or injury. Blocking antibodies have been demonstrated as useful therapies against the neutrophil-associated tissue injury in acute inflammation (Harada et al., 1996, Molecular Medicine Today 2, 482). Cells other than neutrophils that may release inflammatory mediators include other leukocytes, such as basophils, eosinophils, monocytes and lymphocytes, and therapies may be directed against secretion from these cells. Neutrophils, eosinophils, and basophils are each a type of granulocyte, i.e., a leukocyte that has granules in its cytoplasm. Leukocytes synthesize a number of inflammatory mediators that are packaged and stored in cytoplasmic granules. Among these mediators are, for example, myeloperoxidase [MPO] in neutrophils (Borregaard N, Cowland J B. Granules of the human neutrophilic polymorphonuclear leukocyte. Blood 1997; 89:3503-3521), eosinophil peroxidase [EPO] and major basic protein [MBP] in eosinophils (Gleich G J. Mechanisms of eosinophil-associated inflammation. J Allergy Clin Immunol 2000; 105:651-663), lysozyme in monocytes/macrophages (Hoff T, Spencker T, Emmendoerffer A., Goppelt-Struebe M. Effects of glucocorticoids on the TPA-induced monocytic differentiation. J Leukoc Biol 1992; 52:173-182; Balboa M A, Saez Y, Balsinde J. Calcium-independent phospholipase A2 is required for lysozyme secretion in U937 promonocytes. J Immunol 2003; 170:5276-5280), and granzyme in natural killer (NK) cells and cytotoxic lymphocytes (Bochan M R, Goebel W S, Brahmi Z. Stably transfected antisense granzyme B and perforin constructs inhibit human granule-mediated lytic ability. Cell Immunol 1995; 164:234-239; Gong J H., Maki G, Klingemann H G. Characterization of a human cell line (NK-92) with phenotypical and functional characteristics of activated natural killer cells. Leukemia 1994; 8:652-658; Maki G, Klingemann H G, Martinson J A, Tam Y K. Factors regulating the cytotoxic activity of the human natural killer cell line, NK-92. J Hematother Stem Cell Res 2001; 10:369-383; and Takayama H, Trenn G, Sitkovsky M V. A novel cytotoxic T lymphocyte activation assay. J Immunol Methods 1987; 104:183-1907-10). These mediators can be released at sites of injury and can contribute to inflammation and repair, such as in the lung and elsewhere, as a result of the infiltration of these cells to the tissue site of injury or disease. Leukocytes release these granules via an exocytotic mechanism (Burgoyne R D, Morgan A. Secretory granule exocytosis. Physiol Rev 2003; 83:581-632; Logan M R, Odemuyiwa S O, Moqbel R. Understanding exocytosis in immune and inflammatory cells: the molecular basis of mediator secretion. J Allergy Clin Immunol 2003; 111: 923-932), Mast cells, which usually do not circulate in the blood stream, and basophils contain secretory cytoplasmic granules which store and can release, upon cell activation, preformed inflammatory (anaphylactic) mediators, such as histamine; proteoglycans, such as heparin and chondroitin sulphate; proteases such as tryptase, chymase, carboxypeptidase, and cathepsin G-like protease; chemotactic factors, cytokines and metabolites of arachidonic acid that act on the vasculature, smooth muscle, connective tissue, mucous glands and inflammatory cells.

Neutrophils, also known as polymorphonuclear leukocytes (PMN), comprise 50 to 60% of the total circulating leukocytes. Neutrophils act against infectious agents, such as bacteria, fungi, protozoa, viruses, virally infected cells, as well as tumor cells, that penetrate the body's physical barriers at sites of infection or injury. Neutrophils mature through six morphological stages: myeloblast, promyeloblast, myelocyte, metamyelocyte, non-segmented (band) neutrophil, and segmented (functionally active) neutrophil.

In neutrophils, inflammatory mediators are stored in primary (azurophil), secondary (specific), and tertiary (gelatinase) granules, as well as in secretory vesicles. Among numerous mediators of inflammation, primary (azurophil) granules contain myeloperoxidase (MPO), lysozyme, defensins, bactericidal permeability-increasing protein (BPI), elastase, cathepsin G, cathepsin B, cathepsin D, beta-D-glucuronidase, alpha-mannosidase, phospholipase $A_2$, chondroitin-4-sulphate, and proteinase 3 (see, for example, Hartwig J H, Thelen M, Rosen A, Janmey P A, Nairn A C, Aderem A. MARCKS is an actin filament crosslinking protein regulated by protein kinase C and calcium-calmodulin. Nature 1992; 356:618-622); secondary (specific) granules contain lysozyme, lactoferrin, collagenase, complement activator, phospholipase $A_2$, complement receptors, e.g., CR3, CR4, N-formylmethionyl-leucyl-phenylalanine (FMLP) receptors, laminin receptors, cytochrome $b_{558}$, monocyte-chemotactic factor, histaminase, and vitamin B12 binding protein; and small storage granules contain gelatinase, plasminogen activator, cathepsin B, cathepsin D, beta-D-glucuronidase, alpha-mannosidase, and cytochrome $b_{558}$.

Neutrophil granules contain antimicrobial or cytotoxic substances, neutral proteinases, acid hydrolases and a pool of cytoplasmic membrane receptors. Among azurophil granule constituents myeloperoxidase (MPO) is a critical enzyme in the conversion of hydrogen peroxide to hypochlorous acid. Together with hydrogen peroxide and a halide cofactor it forms an effective microbicidal and cytotoxic mechanism of leukocytes—the myeloperoxidase system.

Defensins, which constitute 30 to 50% of azurophilic granule protein, are small (molecule weight <4000) potent antimicrobial peptides that are cytotoxic to a broad range of bacteria, fungi and some viruses. Their toxicity may be due to membrane permeabilization of the target cell which is similar to other channel-forming proteins (performs).

Bacterial permeability-increasing (BPI) protein is a member of performs. It is highly toxic to gram-negative bacteria but not to gram-positive bacteria or fungi and can also neutralize endotoxin, the toxic lipopolysaccharide component of gram-negative bacterial cell envelope.

Lactoferrin sequesters free iron, thereby preventing the growth of ingested microorganisms that survive the killing process and increases bacterial permeability to lysozyme.

Serine proteases such as elastase and cathepsin G hydrolyze proteins in bacterial cell envelopes. Substrates of granulocyte elastase include collagen cross-linkages and proteoglycans, as well as elastin components of blood vessels, ligaments, and cartilage. Cathepsin D cleaves cartilage proteoglycans, whereas granulocyte collagenases are active in cleaving type I and, to a lesser degree, type III collagen from bone, cartilage, and tendon. Collagen breakdown products have chemotactic activity for neutrophils, monocytes, and fibroblasts.

Regulation of tissue destructive potential of lysosomal proteases is mediated by protease inhibitors such as alpha2-macroglobulin and alpha1-antiprotease. These antiproteases are present in serum and synovial fluids. They may function by binding to and covering the active sites of proteases. Protease-antiprotease imbalance can be important in the pathogenesis of emphysema.

Azurophil granules function predominantly in the intracellular milieu (in the phagolysosomal vacuole), where they are involved in the killing and degradation of microorganisms. Neutrophil specific granules are susceptible to release their contents extracellularly and have an important role in initiating inflammation. Specific granules represent an intracellular reservoir of various plasma membrane components including cytochrome b (component of NADPH oxidase, an enzyme responsible for the production of superoxide), receptors for complement fragment iC3b (CR3, CR4), for laminin, and formylmethionyl-peptide chemoattractants. In addition to others, there is histaminase which is relevant for the degradation of histamine, vitamin binding protein, and plasminogen activator which is responsible for plasmin formation and cleavage of C5a from C5.

The importance of neutrophil granules in inflammation is apparent from studies of several patients with congenital abnormalities of the granules. Patients with Chédiak-Higashi syndrome have a profound abnormality in the rate of establishment of an inflammatory response and have abnormally large lysosomal granules. The congenital syndrome of specific granule deficiency is an exceedingly rare disorder characterized by diminished inflammatory responses and severe bacterial infections of skin and deep tissues.

Although mechanisms regulating exocytotic secretion of these granules are only partially understood, several key molecules in the process have been identified, including intracellular Ca2+ transients (Richter et al. Proc Natl Acad Sci USA 1990; 87:9472-9476; Blackwood et al., Biochem J 1990; 266:195-200), G proteins, tyrosine and protein kinases (PK, especially PKC) (Smolen et al., Biochim Biophys Acta 1990; 1052:133-142; Niessen et al., Biochim. Biophys. Acta 1994; 1223:267-273; Naucler et al., Pettersen et al., Chest 2002; 121; 142-150), Rac2 (Abdel-Latif et al., Blood 2004; 104:

832-839; Lacy et al., J Immunol 2003; 170:2670-2679) and various SNARE's, SNAP's and VAMP's (Sollner et al., Nature 1993; 362: 318-324; Lacy, Pharmacol Ther 2005; 107:358-376).

SNARE (Soluble N-ethylmaleimide attachment protein receptor) proteins are a family of membrane-associated proteins characterized by an alpha-helical coiled-coil domain called the SNARE motif (Li et al., Cell. Mol. Life. Sci. 60: 942-960 (2003)). These proteins are classified as v-SNAREs and t-SNAREs based on their localization on vesicle or target membrane; another classification scheme defines R-SNAREs and Q-SNAREs, as based on the conserved arginine or glutamine residue in the centre of the SNARE motif. SNAREs are localized to distinct membrane compartments of the secretory and endocytic trafficking pathways, and contribute to the specificity of intracellular membrane fusion processes. The t-SNARE domain consists of a 4-helical bundle with a coiled-coil twist. The SNARE motif contributes to the fusion of two membranes. SNARE motifs fall into four classes: homologues of syntaxin 1a (t-SNARE), VAMP-2 (v-SNARE), and the N- and C-terminal SNARE motifs of SNAP-25. One member from each class may interact to form a SNARE complex. The SNARE motif is found in the N-terminal domains of certain syntaxin family members such as syntaxin 1a, which is required for neurotransmitter release (Lerman et al., Biochemistry 39: 8470-8479 (2000)), and syntaxin 6, which is found in endosomal transport vesicles (Misura et al., Proc. Natl. Acad. Sci. U.S.A. 99: 9184-9189 (2002)).

SNAP-25 (synaptosome-associated protein 25 kDa) proteins are components of SNARE complexes, which may account for the specificity of membrane fusion and to directly execute fusion by forming a tight complex (the SNARE or core complex) that brings the synaptic vesicle and plasma membranes together. The SNAREs constitute a large family of proteins that are characterized by 60-residue sequences known as SNARE motifs, which have a high propensity to form coiled coils and often precede carboxy-terminal transmembrane regions. The synaptic core complex is formed by four SNARE motifs (two from SNAP-25 and one each from synaptobrevin and syntaxin 1) that are unstructured in isolation but form a parallel four-helix bundle on assembly. The crystal structure of the core complex has revealed that the helix bundle is highly twisted and contains several salt bridges on the surface, as well as layers of interior hydrophobic residues. A polar layer in the centre of the complex is formed by three glutamines (two from SNAP-25 and one from syntaxin 1) and one arginine (from synaptobrevin) (Rizo et al., Nat Rev Neurosci 3: 641-653 (2002)). Members of the SNAP-25 family contain a cluster of cysteine residues that can be palmitoylated for membrane attachment (Risinger et al., J. Biol. Chem. 268: 24408-24414 (1993)).

The major role of neutrophils is to phagocytose and destroy infectious agents. They also limit the growth of some microbes, prior to onset of adaptive (specific) immunological responses. Although neutrophils are essential to host defense, they have also been implicated in the pathology of many chronic inflammatory conditions and in ischemia-reperfusion injury. Hydrolytic enzymes of neutrophil origin and oxidatively inactivated protease inhibitors can be detected in fluid isolated from inflammatory sites. Under normal conditions, neutrophils can migrate to sites of infection without damage to host tissues. However, undesirable damage to a host tissue can sometimes occur. This damage may occur through several independent mechanisms. These include premature activation during migration, extracellular release of toxic products during the killing of some microbes, removal of infected or damage host cells and debris as a first step in tissue remodeling, or failure to terminate acute inflammatory responses. Ischemia-reperfusion injury is associated with an influx of neutrophils into the affected tissue and subsequent activation. This may be triggered by substances released from damaged host cells or as a consequence of superoxide generation through xantine oxidase.

Under normal conditions, blood may contain a mixture of normal, primed, activated and spent neutrophils. In an inflammatory site, mainly activated and spent neutrophils are present. Activated neutrophils have enhanced production of reactive oxygen intermediates (ROI). A subpopulation of neutrophils with the enhanced respiratory burst has been detected in the blood of people with an acute bacterial infection and patients with the adult respiratory distress syndrome (ARDS). This is an example of a neutrophil paradox. Neutrophils have been implicated in the pathology of this condition because of the large influx of these cells into the lung and the associated tissue damage caused by oxidants and hydrolytic enzymes released from activated neutrophils. The impairment of neutrophil microbicidal activity that occurs as the ARDS worsens may be a protective response on the part of the host, which is induced locally by inflammatory products.

The acute phase of thermal injury is also associated with neutrophil activation, and this is followed by a general impairment in various neutrophil functions. Activation of neutrophils by immune complexes in synovial fluid contributes to the pathology of rheumatoid arthritis. Chronic activation of neutrophils may also initiate tumor development because some ROI generated by neutrophils damage DNA and proteases promote tumor cell migration. In patients suffering from severe burns, a correlation has been established between the onset of bacterial infection and reduction in the proportion and absolute numbers of neutrophils positive for antibody and complement receptors. Oxidants of neutrophil origin have also been shown to oxidize low-density lipoproteins (LDL), which are then more effectively bound to the plasma membrane of macrophages through specific scavenger receptors. Uptake of these oxidized LDL by macrophages may initiate atherosclerosis. In addition, primed neutrophils have been found in people with essential hypertension, Hodgkin's disease, inflammatory bowel disease, psoriasis, sarcoidosis, and septicemia, where priming correlates with high concentrations of circulating TNF-alpha (cachectin).

Hydrolytic damage to host tissue and therefore chronic inflammatory conditions may occur when antioxidant and antiprotease screens are overwhelmed. Antiprotease deficiency is thought to be responsible for the pathology of emphysema. Many antiproteases are members of the serine protease inhibitor (SERPIN) family. Although the circulation is rich in antiproteases, these large proteins may be selectively excluded at sites of inflammation because neutrophils adhere to their targets. Oxidative stress may initiate tissue damage by reducing the concentration of extracellular antiproteases to below the level required to inhibit released proteases. Chlorinated oxidants and hydrogen peroxide can inactivate antiproteases such as alpha1-protease inhibitor and alpha2-macroglobulin, which are endogenous inhibitors of elastase, but simultaneously activate latent metalloproteases such as collagenases and gelatinase, which contribute to the further inactivation of antiproteases.

Cytoplasmic constituents of neutrophils may also be a cause of formation of specific anti-neutrophil cytoplasmic antibodies (ANCA), which are closely related to the development of systemic vasculitis and glomerulonephritis. ANCA are antibodies directed against enzymes that are found mainly within the azurophil or primary granules of neutrophils. There are three types of ANCA that can be distinguished by the patterns they produce by indirect immunofluorescence on normal ethanol-fixed neutrophils. Diffuse fine granular cytoplasmic fluorescence (cANCA) is typically found in Wegener's granulomatosis, in some cases of microscopic polyarteritis and Churg Strauss syndrome, and in some cases of crescentic and segmental necrotizing glomerulonephritis. The target antigen is usually proteinase 3. Perinuclear fluorescence (pANCA) is found in many cases of microscopic polyarteritis and glomerulonephritis. These antibodies are often directed against myeloperoxidase but other targets include elastase, cathepsin G, lactoferrin, lysozyme and beta-D-glucuronidase. The third group designated "atypical" ANCA includes neutrophil nuclear fluorescence and some unusual cytoplasmic patterns and while a few of the target antigens are shared with pANCA, the others have not been identified yet. pANCA are also found in a third of patients with Crohn's disease. The reported incidence of ANCA in rheumatoid arthritis and SLE varies considerably but the patterns are predominantly pANCA and atypical ANCA.

The eosinophil is a terminally differentiated, end-stage leukocyte that resides predominantly in submucosal tissue and is recruited to sites of specific immune reactions, including allergic diseases. The eosinophil cytoplasm contains large ellipsoid granules with an electron-dense crystalline nucleus and partially permeable matrix. In addition to these large primary crystalloid granules, there is another granule type that is smaller (small granule) and lacks the crystalline nucleus. The large specific granules of eosinophils contain at least four distinct cationic proteins, which exert a range of biological effects on host cells and microbial targets: major basic protein (MBP), eosinophil cationic protein (ECP), eosinophil derived neurotoxin (EDN), and eosinophil peroxidase (EPO). Basophils contain about one fourth as much major basic protein as eosinophils together with detectable amounts of EDN, ECP and EPO. Small amounts of EDN and ECP are also found in neutrophils (Gleich G J. Mechanisms of eosinophil-associated inflammation. J Allergy Clin Immunol 2000; 105:651-663). MBP appears to lack enzymatic activity but is a highly cationic polypeptide which may exert its toxic activities by interactions with lipid membranes leading to their derangement. Both MBP and EPO can act as selective allosteric inhibitors of agonist binding to M2 muscarinic receptors. These proteins may contribute to M2 receptor dysfunction and enhance vagally mediated bronchoconstriction in asthma. EDN can specifically damage the myelin coat of neurons. Histaminase and a variety of hydrolytic lysosomal enzymes are also present in the large specific granules of eosinophils. Among the enzymes in small granules of eosinophils are aryl sulphatase, acid phosphatase, and a 92 kDa metalloproteinase, a gelatinase. Eosinophils can elaborate cytokines which include those with potential autocrine growth-factor activities for eosinophils and those with potential roles in acute and chronic inflammatory responses. Three cytokines have growth-factor activities for eosinophils: granulocyte-macrophage colony-stimulating factor (GM-CSF), IL-3 and IL-5. Other cytokines produced by human eosinophils that may have activities in acute and chronic inflammatory responses include IL-1-alpha, IL-6, IL-8, TNF-alpha and both transforming growth factors, TGF-alpha and TGF-beta.

Eosinophils contain crystalloid granules that contain MBP, eosinophil cationic protein, EPO, and eosinophil-derived neurotoxin (Gleich, J Allergy Clin Immunol 2000; 105:651-663). The human promyelocytic cell line HL-60 clone 15 can be used to examine secretion of EPO. This cell line was established from a clone of HL-60 that had been grown at an elevated pH for two months (Fischkoff, Leuk Res 1988; 12:679-686) and then treated with butyric acid to allow the cells to differentiate so as to exhibit many of the characteristics of peripheral blood eosinophils, including expression of eosinophil-specific granule proteins (Rosenberg et al., J Exp Med 1989; 170:163-176; Tiffany et al., J Leukoc Biol 1995; 58:49-54; Badewa et al., Exp Biol Med 2002; 227:645-651).

Eosinophils can participate in hypersensitivity reactions, especially through two lipid inflammatory mediators, leukotriene $C^4$ ($LTC^4$) and platelet activating factor (PAF). Both mediators contract airway smooth muscle, promote the secretion of mucus, alter vascular permeability and elicit eosinophil and neutrophil infiltration. In addition to the direct activities of these eosinophil-derived mediators, MBP can stimulate the release of histamine from basophils and mast cells, and MBP can stimulate the release of EPO from mast cells. Eosinophils can serve as a local source of specific lipid mediators as well as induce the release of mediators from mast cells and basophils. Eosinophil granule content is released following similar stimuli to neutrophil granules, e.g. during phagocytosis of opsonized particles and by chemotactic factors. Neutrophil lysosomal enzymes act primarily on material engulfed in phagolysosomes, while the eosinophil granule contents act mainly on extracellular target structure such as parasites and inflammatory mediators.

Monocyte and macrophage development takes place in the bone marrow and passes through the following steps: stem cell; committed stem cell; monoblast; promonocyte; monocyte in bone marrow; monocyte in peripheral blood; and macrophage in tissues. Monocyte differentiation in the bone marrow proceeds rapidly (1.5 to 3 days). During differentiation, granules are formed in monocyte cytoplasm and these can be divided as in neutrophils into at least two types. However, they are fewer and smaller than their neutrophil counterparts (azurophil and specific granules). Their enzyme content is similar.

Granule-bound enzymes of monocytes/macrophages include lysozyme, acid phosphatase, and beta-glucuronidase. As a model for in vivo studies, lysozyme secretion from U937 cells was used. This cell line is derived from a human histiocytic lymphoma and has been used as a monocytic cell line that can be activated by a variety of agonists, such as PMA (Hoff et al., J Leukoc Biol 1992; 52:173-182; Balboa et al., J Immunol 2003; 170:5276-5280; Sundstrom et al., Int J Cancer 1976; 17:565-577).

Natural killer (NK) cells and cytotoxic lymphocytes contain potent cytotoxic granules including perform, a pore-forming protein, and granzymes, lymphocyte-specific serine proteases. For example, the NK-92 cell line is an IL-2-dependent human line established from a patient with rapidly progressive non-Hodgkin's lymphoma (Gong J H., Maki G, Klingemann H G. Characterization of a human cell line (NK-92) with phenotypical and functional characteristics of activated natural killer cells. Leukemia 1994; 8:652-658). NK-92 cells express high levels of molecules involved in the perforin-granzyme cytolytic pathway that targets a wide range of malignant cells (Gong et al, vide infra, and Maki G, Klingemann H G, Martinson J A, Tam Y K. Factors regulating the cytotoxic activity of the human natural killer cell line, NK-92. J Hematother Stem Cell Res 2001; 10:369-383).

Granzymes are exogenous serine proteases that are released by cytoplasmic granules within cytotoxic T cells and natural killer cells. Granzymes can induce apoptosis within virus-infected cells, thus destroying them.

Extracellular release of a mediator of inflammation (inflammatory mediator) from a granulocyte (or leukocyte), and extracellular release of more than one mediator of inflammation (inflammatory mediator) from a granulocyte (or leukocyte) is sometimes referred to herein as degranulation. In a preferred embodiment, the release of a mediator of inflammation comprises release of said mediator from a granule located in the interior of a granulocyte or leukocyte. The release of inflammatory mediator is preferably the release of an inflammatory mediator from these granules.

Neutrophils and macrophages, upon priming by pro-inflammatory agents (inflammatory stimulants) such as TNFα, dramatically increase their synthesis of MARCKS protein: as much as 90% of the new protein formed by neutrophils in response to either TNFα or lipopolysaccharide (LPS) is MARCKS (Thelen M, Rosen A, Nairn A C, Aderem A. Tumor necrosis factor alpha modifies agonist-dependent responses in human neutrophils by inducing the synthesis and myristoylation of a specific protein kinase C substrate. Proc Natl Acad Sci USA 1990; 87:5603-5607). MARCKS can thus have an important role in subsequent release of inflammatory mediators when granule-containing cells, such as neutrophils and macrophages, are stimulated by agonists, especially those that work by activating PKC (Burgoyne et al., Physiol Rev 2003; 83:581-632; Logan et al. J Allergy Clin Immunol 2003; 111: 923-932; Smolen et al., Biochim Biophys Acta 1990; 1052:133-142; Niessen et al., Biochim. Biophys. Acta 1994; 1223:267-273; Naucler et al., J Leukoc Biol 2002; 71:701-710).

In one aspect of this invention, administration of a degranulation-inhibiting amount of MANS peptide or an active fragment thereof as described herein to a site of inflammation in a subject, which site of inflammation has resulted from the onset of entry of a disease, a condition, a trauma, a foreign body, or a combination thereof at the site of inflammation in the subject, can reduce the amount of a mediator of inflammation released from infiltrating leukocytes at the site of inflammation, where the leukocytes are preferably granulocytes. The administration of the MANS peptide and/or at least one active fragment thereof can reduce the amount of a mediator of inflammation released from leukocytes such as granulocytes infiltrating into the site of inflammation. The degranulation-inhibiting amount of MANS peptide, or the degranulation-inhibiting amount of an active fragment thereof, is sufficient to reduce or inhibit the exocytotic release of inflammatory mediators from granules contained within the inflammatory cells infiltrating into the site. Degranulation-inhibiting efficacy is measured at a time after administration of the MANS peptide or the active fragment thereof by comparison of the percent of inhibition (i.e., percent of reduction) of the release of mediators of inflammation from said cells (leukocytes or granulocytes or other inflammatory cells) relative to the level or amount or concentration of said mediators of inflammation released or produced at approximately the same time in the absence of MANS peptide and/or in the absence of the active fragment thereof. Additionally, a skilled clinician can determine whether inflammation at the tissue site has been reduced by measuring symptoms and parameters of inflammation known as indicators of the disease to determine whether a sufficient or therapeutically effective amount MANS peptide and/or an active fragment thereof has been administered. A sufficient degranulation-inhibiting amount is the amount which produces a percentage of reduction of a mediator of inflammation released from a granulocyte, at the site of inflammation, which percentage is from about 1% to about 99%, preferably from 5% to about 99%, more preferably from about 10% to about 99%, even more preferably from about 25% to 99%, and even more preferably from about 50% to about 99% of the amount of said mediator of inflammation released from said granulocyte in the absence of MANS peptide or an active fragment thereof tested under the same conditions.

In one aspect of this invention, administration of a degranulation-inhibiting amount of MANS peptide to a site of inflammatory stimulation in an animal, which site of inflammatory stimulation has been created by administration of an inflammation-stimulating amount of an inflammatory stimulant to said site, can reduce the amount of a mediator of inflammation released from a granulocyte, which granulocyte is stimulated by said inflammatory stimulant at said site of inflammatory stimulation, from about 1% to about 99%, preferably from 5% to about 99%, more preferably from about 10% to about 99%, even more preferably from about 25% to 99%, and even more preferably from about 50% to about 99% of the amount of said mediator of inflammation released from said granulocyte in the absence of MANS peptide in the presence of the identical inflammation-stimulating amount of said inflammatory stimulant.

In another aspect of this invention, administration of a degranulation-inhibiting amount of MANS peptide to a site of inflammatory stimulation in an animal, which site of inflammatory stimulation has been created by administration of an inflammation-stimulating amount of an inflammatory stimulant to said site, can reduce the amount of a mediator of inflammation released from a granulocyte, which granulocyte is stimulated by said inflammatory stimulant at said site of inflammatory stimulation, by 100% of the amount of said mediator of inflammation released from said granulocyte in the absence of MANS peptide in the presence of the identical inflammation-stimulating amount of said inflammatory stimulant.

An example of an inflammatory stimulant used in in vitro examples herein is phorbol 12-myristate 13-acetate (PMA). Monocyte chemoattractant protein (MCP-1) is nearly as effective as C5a, and much more potent than IL-8, in the degranulation of basophils, resulting in histamine release. Histamine release can occur after stimulation with chemokines (i.e., chemoattractant cytokines), RANTES and MIP-1.

In a preferred embodiment, relative to the basal concentration of MARCKS peptide present at the site of inflammatory stimulation, the degranulation-inhibiting amount of MANS peptide administered to a site of inflammatory stimulation in an animal comprises from about 1 time to about 1,000,000 times the concentration of the MARCKS peptide at said site of inflammatory stimulation, preferably from about 1 time to about 100,000 times the concentration of the MARCKS peptide at said site of inflammatory stimulation, more preferably from about 1 time to about 10,000 times the concentration of the MARCKS peptide at said site of inflammatory stimulation, even more preferably from about 1 time to about 1,000 times the concentration of the MARCKS peptide at said site of inflammatory stimulation, even more preferably from about 1 time to about 100 times the concentration of the MARCKS peptide at said site of inflammatory stimulation, and even more preferably from about 1 time to about 10 times the concentration of the MARCKS peptide at said site of inflammatory stimulation.

In a preferred embodiment, the granulocyte resides on or in the airway of an animal, preferably a human, and the MANS peptide is administered by inhalation, such as by inhalation of a pharmaceutical composition comprising the MANS peptide, for example a pharmaceutical composition comprising the MANS peptide and an aqueous solution, which composition is administered in the form of an aerosol, or a pharmaceutical composition comprising the MANS peptide in the form of a dry powder, which composition is administered using a dry powder inhaler. Other methods and devices known in the art for administration of a solution or powder by inhalation such as, for example, droplets, sprays, and nebulizers, can be useful.

In some embodiments, it is possible that the peptide of the present invention may block secretory processes that are physiologically important, including basal secretory functions. Although inventors do not wish to be bound to any particular theory of the invention, it is thought that the mechanisms regulating such basal secretion are different than those regulating stimulated secretion. Alternatively, basal secretory mechanisms may require less MARCKS protein than stimulated secretion. Basal secretion may be preserved since all therapies to block MARCKS-mediated secretion may not eliminate all MARCKS function.

As used herein, the term "MARCKS nucleotide sequence" refers to any nucleotide sequence derived from a gene encoding a MARCKS protein, including, for example, DNA or RNA sequence, DNA sequence of the gene, any transcribed RNA sequence, RNA sequence of the pre-mRNA or mRNA transcript, and DNA or RNA bound to protein.

Precise delivery of the MARCKS-blocking peptide may also overcome any potential limitations of blocking important secretory processes. Delivering such agents to the respiratory tract should be readily accomplished with inhaled formulations. Since these agents may be useful in treating inflammatory bowel disease, one can envision delivery of the blocking agents into the rectum/colon/intestinal tract via enema or suppositories. Intraarticular injections or transdermal delivery into inflamed joints may yield relief to patients with arthritic or autoimmune diseases by limiting the secretion from localized inflammatory cells. Injection into areas surrounding nerve endings may inhibit secretion of some types of neurotransmitters, blocking transmission of severe pain or uncontrolled muscle spasms. Delivery of the peptide for the treatment of inflammatory skin diseases should be readily accomplished using various topical formulations known in the art.

It is believed that MARCKS interacts with actin and myosin in the cytoplasm and thus may be able to tether the granules to the cellular contractile apparatus, thus, mediating subsequent granule movement and exocytosis. Secretion of the inflammatory mediatory MPO from neutrophils may also be maximized by activation of both PKC and PKG. It is possible that MARCKS serves as the point of convergence for coordinating actions of these two protein kinases that control secretion from membrane-bound compartments in inflammatory cells (i.e. secretion of MPO from neutrophils).

The present invention demonstrates secretion of the inflammatory mediator MPO from canine or human neutrophils was enhanced by concurrent activation of both PKC and PKG, while activation of either kinase alone was insufficient to induce a maximal secretory response. An enhanced secretory response to PMA alone has been documented in NHBE cells and in neutrophils as demonstrated herein, although the magnitude of the response was much less than that observed by others in a rat goblet-like cell line. See, Abdullah et al, supra. In addition, although it was reported previously that a cGMP analogue could induce significant mucin secretion from cultured guinea pig tracheal epithelial cells (Fischer et al., supra), it should be noted that this response did not reach significant levels until 8 h of exposure. A secretory response with such a long lag period is unlikely to be a direct effect and probably involves de novo protein synthesis as opposed to release of preformed and stored cytoplasmic granules.

As stated above, the present invention may be used in a pharmaceutical formulation. In certain embodiments, the drug product is present in a solid pharmaceutical composition that may be suitable for oral administration. A solid composition of matter according to the present invention may be formed and may be mixed with and/or diluted by an excipient. The solid composition of matter also may be enclosed within a carrier, which may be, for example, in the form of a capsule, sachet, tablet, paper, or other container. When the excipient serves as a diluent, it may be a solid, semi-solid, or liquid material that acts as a vehicle, carrier, or medium for the composition of matter.

Various suitable excipients will be understood by those skilled in the art and may be found in the National Formulary, 19: 2404-2406 (2000), the disclosure of pages 2404 to 2406 being incorporated herein in their entirety. Examples of suitable excipients include, but are not limited to, starches, gum arabic, calcium silicate, microcrystalline cellulose, methacrylates, shellac, polyvinylpyrolidone, cellulose, water, syrup, and methylcellulose. The drug product formulations additionally can include lubricating agents such as, for example, talc, magnesium stearate and mineral oil; wetting agents; emulsifying and suspending agents; preserving agents such as methyl- and propyl hydroxybenzoates; sweetening agents; or flavoring agents. Polyols, buffers, and inert fillers also may be used. Examples of polyols include, but are not limited to, mannitol, sorbitol, xylitol, sucrose, maltose, glucose, lactose, dextrose, and the like. Suitable buffers include, but are not limited to, phosphate, citrate, tartrate, succinate, and the like. Other inert fillers that may be used include those that are known in the art and are useful in the manufacture of various dosage forms. If desired, the solid formulations may include other components such as bulking agents and/or granulating agents, and the like. The drug products of the invention may be formulated so as to provide quick, sustained, or delayed release of the active ingredient after administration to the patient by employing procedures well known in the alt.

To form tablets for oral administration, the composition of matter of the present invention may be made by a direct compression process. In this process, the active drug ingredients may be mixed with a solid, pulverant carrier such as, for example, lactose, saccharose, sorbitol, mannitol, starch, amylopectin, cellulose derivatives or gelatin, and mixtures thereof, as well as with an antifriction agent such as, for example, magnesium stearate, calcium stearate, and polyethylene glycol waxes. The mixture may then be pressed into tablets using a machine with the appropriate punches and dies to obtain the desired tablet size. The operating parameters of the machine may be selected by the skilled artisan. Alternatively, tablets for oral administration may be formed by a wet granulation process. Active drug ingredients may be mixed with excipients and/or diluents. The solid substances may be ground or sieved to a desired particle size. A binding agent may be added to the drug. The binding agent may be suspended and homogenized in a suitable solvent. The active ingredient and auxiliary agents also may be mixed with the binding agent solution. The resulting dry mixture is moistened with the solution uniformly. The moistening typically causes the particles to aggregate slightly, and the resulting mass is pressed through a stainless steel sieve having a desired size. The mixture is then dried in controlled drying units for the determined length of time necessary to achieve a desired particle size and consistency. The granules of the dried mixture are sieved to remove any powder. To this mixture, disintegrating, antifriction, and/or anti-adhesive agents may be added. Finally, the mixture is pressed into tablets using a machine with the appropriate punches and dies to obtain the desired tablet size. The operating parameters of the machine may be selected by the skilled artisan.

If coated tablets are desired, the above prepared core may be coated with a concentrated solution of sugar or cellulosic polymers, which may contain gum arabic, gelatin, talc, titanium dioxide, or with a lacquer dissolved in a volatile organic solvent or a mixture of solvents. To this coating various dyes may be added in order to distinguish among tablets with different active compounds or with different amounts of the active compound present. In a particular embodiment, the active ingredient may be present in a core surrounded by one or more layers including enteric coating layers.

Soft gelatin capsules may be prepared in which capsules contain a mixture of the active ingredient and vegetable oil. Hard gelatin capsules may contain granules of the active ingredient in combination with a solid, pulverulent carrier, such as, for example, lactose, saccharose, sorbitol, mannitol, potato starch, corn starch, amylopectin, cellulose derivatives, and/or gelatin.

Liquid preparations for oral administration may be prepared in the form of syrups or suspensions, e.g., solutions containing an active ingredient, sugar, and a mixture of ethanol, water, glycerol, and propylene glycol. If desired, such liquid preparations may comprise one or more of following: coloring agents, flavoring agents, and saccharin. Thickening agents such as carboxymethylcellulose also may be used.

In the event that the above pharmaceuticals are to be used for parenteral administration, such a formulation may comprise sterile aqueous injection solutions, non-aqueous injection solutions, or both, comprising the composition of matter of the present invention. When aqueous injection solutions are prepared, the composition of matter may be present as a water soluble pharmaceutically acceptable salt. Parenteral preparations may contain anti-oxidants, buffers, bacteriostats, and solutes which render the formulation isotonic with the blood of the intended recipient. Aqueous and non-aqueous sterile suspensions may comprise suspending agents and thickening agents. The formulations may be presented in unit-dose or multi-dose containers, for example sealed ampules and vials. Extemporaneous injection solutions and suspensions may be prepared from sterile powders, granules and tablets of the kind previously described.

The composition of matter also may be formulated such that it may be suitable for topical administration (e.g., skin cream). These formulations may contain various excipients known to those skilled in the art. Suitable excipients may include, but are not limited to, cetyl esters wax, cetyl alcohol, white wax, glyceryl monostearate, propylene glycol, monostearate, methyl stearate, benzyl alcohol, sodium lauryl sulfate, glycerin, mineral oil, water, carbomer, ethyl alcohol, acrylate adhesives, polyisobutylene adhesives, and silicone adhesives.

In a preferred embodiment, peptide fragments are disclosed in Table 2 and are of a length of at least 4 to 23 amino acid residues in length and having amino acid sequences identical to an amino acid sequence of the MANS peptide, wherein the N-terminal amino acid of the peptides are selected from position 2 to 21 of the MANS peptide sequence (SEQ ID NO: 1). The more preferred peptide fragment length is from at least 6 amino acids to 23 amino acids. Preferably these peptides are acylated at the alpha N-terminal amino acid, and more preferably these peptides are myristoylated at the alpha-N-terminal amino acid position.

TABLE 2

| Peptide No. | Sequence | Sequence ID No. |
|---|---|---|
| peptide 3 | AQFSKTAAKGEAAAERPGEAAVA | SEQ ID NO. 3 |
| peptide 5 | AQFSKTAAKGEAAAERPGEAAV | SEQ ID NO. 5 |
| peptide 8 | AQFSKTAAKGEAAAERPGEAA | SEQ ID NO. 8 |
| peptide 12 | AQFSKTAAKGEAAAERPGEA | SEQ ID NO. 12 |
| peptide 17 | AQFSKTAAKGEAAAERPGE | SEQ ID NO. 17 |
| peptide 23 | AQFSKTAAKGEAAAERPG | SEQ ID NO. 23 |
| peptide 30 | AQFSKTAAKGEAAAERP | SEQ ID NO. 30 |
| peptide 38 | AQFSKTAAKGEAAAER | SEQ ID NO. 38 |
| peptide 47 | AQFSKTAAKGEAAAE | SEQ ID NO. 47 |
| peptide 57 | AQFSKTAAKGEAAA | SEQ ID NO. 57 |
| peptide 68 | AQFSKTAAKGEAA | SEQ ID NO. 68 |
| peptide 80 | AQFSKTAAKGEA | SEQ ID NO. 80 |
| peptide 93 | AQFSKTAAKGE | SEQ ID NO. 93 |
| peptide 107 | AQFSKTAAKG | SEQ ID NO. 107 |
| peptide 122 | AQFSKTAAK | SEQ ID NO. 122 |
| peptide 138 | AQFSKTAA | SEQ ID NO. 138 |
| peptide 155 | AQFSKTA | SEQ ID NO. 155 |
| peptide 173 | AQFSKT | SEQ ID NO. 173 |
| peptide 192 | AQFSK | SEQ ID NO. 192 |
| peptide 212 | AQFS | SEQ ID NO. 212 |
| peptide 6 | QFSKTAAKGEAAAERPGEAAVA | SEQ ID NO. 6 |
| peptide 9 | QFSKTAAKGEAAAERPGEAAV | SEQ ID NO. 9 |
| peptide 13 | QFSKTAAKGEAAAERPGEAA | SEQ ID NO. 13 |
| peptide 18 | QFSKTAAKGEAAAERPGEA | SEQ ID NO. 18 |
| peptide 24 | QFSKTAAKGEAAAERPGE | SEQ ID NO. 24 |
| peptide 31 | QFSKTAAKGEAAAERPG | SEQ ID NO. 31 |
| peptide 39 | QFSKTAAKGEAAAERP | SEQ ID NO. 39 |
| peptide 48 | QFSKTAAKGEAAAER | SEQ ID NO. 48 |
| peptide 58 | QFSKTAAKGEAAAE | SEQ ID NO. 58 |
| peptide 69 | QFSKTAAKGEAAA | SEQ ID NO. 69 |
| peptide 81 | QFSKTAAKGEAA | SEQ ID NO. 81 |
| peptide 94 | QFSKTAAKGEA | SEQ ID NO. 94 |
| peptide 108 | QFSKTAAKGE | SEQ ID NO. 108 |
| peptide 123 | QFSKTAAKG | SEQ ID NO. 123 |
| peptide 139 | QFSKTAAK | SEQ ID NO. 139 |
| peptide 156 | QFSKTAA | SEQ ID NO. 156 |
| peptide 174 | QFSKTA | SEQ ID NO. 174 |
| peptide 193 | QFSKT | SEQ ID NO. 193 |
| peptide 213 | QFSK | SEQ ID NO. 213 |

TABLE 2-continued

| Peptide No. | Sequence | Sequence ID No. |
|---|---|---|
| peptide 10 | FSKTAAKGEAAAERPGEAAVA | SEQ ID NO. 10 |
| peptide 14 | FSKTAAKGEAAAERPGEAAV | SEQ ID NO. 14 |
| peptide 19 | FSKTAAKGEAAAERPGEAA | SEQ ID NO. 19 |
| peptide 25 | FSKTAAKGEAAAERPGEA | SEQ ID NO. 25 |
| peptide 32 | FSKTAAKGEAAAERPGE | SEQ ID NO. 32 |
| peptide 40 | FSKTAAKGEAAAERPG | SEQ ID NO. 40 |
| peptide 49 | FSKTAAKGEAAAERP | SEQ ID NO. 49 |
| peptide 59 | FSKTAAKGEAAAER | SEQ ID NO. 59 |
| peptide 70 | FSKTAAKGEAAAE | SEQ ID NO. 70 |
| peptide 82 | FSKTAAKGEAAA | SEQ ID NO. 82 |
| peptide 95 | FSKTAAKGEAA | SEQ ID NO. 95 |
| peptide 109 | FSKTAAKGEA | SEQ ID NO. 109 |
| peptide 124 | FSKTAAKGE | SEQ ID NO. 124 |
| peptide 140 | FSKTAAKG | SEQ ID NO. 140 |
| peptide 157 | FSKTAAK | SEQ ID NO. 157 |
| peptide 175 | FSKTAA | SEQ ID NO. 175 |
| peptide 194 | FSKTA | SEQ ID NO. 194 |
| peptide 214 | FSKT | SEQ ID NO. 214 |
| peptide 15 | SKTAAKGEAAAERPGEAAVA | SEQ ID NO. 15 |
| peptide 20 | SKTAAKGEAAAERPGEAAV | SEQ ID NO. 20 |
| peptide 26 | SKTAAKGEAAAERPGEAA | SEQ ID NO. 26 |
| peptide 33 | SKTAAKGEAAAERPGEA | SEQ ID NO. 33 |
| peptide 41 | SKTAAKGEAAAERPGE | SEQ ID NO. 41 |
| peptide 50 | SKTAAKGEAAAERPG | SEQ ID NO. 50 |
| peptide 60 | SKTAAKGEAAAERP | SEQ ID NO. 60 |
| peptide 71 | SKTAAKGEAAAER | SEQ ID NO. 71 |
| peptide 83 | SKTAAKGEAAAE | SEQ ID NO. 83 |
| peptide 96 | SKTAAKGEAAA | SEQ ID NO. 96 |
| peptide 110 | SKTAAKGEAA | SEQ ID NO. 110 |
| peptide 125 | SKTAAKGEA | SEQ ID NO. 125 |
| peptide 141 | SKTAAKGE | SEQ ID NO. 141 |
| peptide 158 | SKTAAKG | SEQ ID NO. 158 |
| peptide 176 | SKTAAK | SEQ ID NO. 176 |
| peptide 195 | SKTAA | SEQ ID NO. 195 |
| peptide 215 | SKTA | SEQ ID NO. 215 |
| peptide 21 | KTAAKGEAAAERPGEAAVA | SEQ ID NO. 21 |
| peptide 27 | KTAAKGEAAAERPGEAAV | SEQ ID NO. 27 |
| peptide 34 | KTAAKGEAAAERPGEAA | SEQ ID NO. 34 |
| peptide 42 | KTAAKGEAAAERPGEA | SEQ ID NO. 42 |
| peptide 51 | KTAAKGEAAAERPGE | SEQ ID NO. 51 |
| peptide 61 | KTAAKGEAAAERPG | SEQ ID NO. 61 |
| peptide 72 | KTAAKGEAAAERP | SEQ ID NO. 72 |
| peptide 84 | KTAAKGEAAAER | SEQ ID NO. 84 |
| peptide 97 | KTAAKGEAAAE | SEQ ID NO. 97 |
| peptide 111 | KTAAKGEAAA | SEQ ID NO. 111 |
| peptide 126 | KTAAKGEAA | SEQ ID NO. 126 |
| peptide 142 | KTAAKGEA | SEQ ID NO. 142 |
| peptide 159 | KTAAKGE | SEQ ID NO. 159 |
| peptide 177 | KTAAKG | SEQ ID NO. 177 |
| peptide 196 | KTAAK | SEQ ID NO. 196 |
| peptide 216 | KTAA | SEQ ID NO. 216 |
| peptide 28 | TAAKGEAAAERPGEAAVA | SEQ ID NO. 28 |
| peptide 35 | TAAKGEAAAERPGEAAV | SEQ ID NO. 35 |
| peptide 43 | TAAKGEAAAERPGEAA | SEQ ID NO. 43 |
| peptide 52 | TAAKGEAAAERPGEA | SEQ ID NO. 52 |
| peptide 62 | TAAKGEAAAERPGE | SEQ ID NO. 62 |
| peptide 73 | TAAKGEAAAERPG | SEQ ID NO. 73 |
| peptide 85 | TAAKGEAAAERP | SEQ ID NO. 85 |
| peptide 98 | TAAKGEAAAER | SEQ ID NO. 98 |
| peptide 112 | TAAKGEAAAE | SEQ ID NO. 112 |
| peptide 127 | TAAKGEAAA | SEQ ID NO. 127 |
| peptide 143 | TAAKGEAA | SEQ ID NO. 143 |
| peptide 160 | TAAKGEA | SEQ ID NO. 160 |
| peptide 178 | TAAKGE | SEQ ID NO. 178 |
| peptide 197 | TAAKG | SEQ ID NO. 197 |
| peptide 217 | TAAK | SEQ ID NO. 217 |
| peptide 36 | AAKGEAAAERPGEAAVA | SEQ ID NO. 36 |
| peptide 44 | AAKGEAAAERPGEAAV | SEQ ID NO. 44 |
| peptide 53 | AAKGEAAAERPGEAA | SEQ ID NO. 53 |
| peptide 63 | AAKGEAAAERPGEA | SEQ ID NO. 63 |
| peptide 74 | AAKGEAAAERPGE | SEQ ID NO. 74 |
| peptide 86 | AAKGEAAAERPG | SEQ ID NO. 86 |
| peptide 99 | AAKGEAAAERP | SEQ ID NO. 99 |
| peptide 113 | AAKGEAAAER | SEQ ID NO. 113 |
| peptide 128 | AAKGEAAAE | SEQ ID NO. 128 |
| peptide 144 | AAKGEAAA | SEQ ID NO. 144 |
| peptide 161 | AAKGEAA | SEQ ID NO. 161 |

TABLE 2-continued

| Peptide No. | Sequence | Sequence ID No. |
|---|---|---|
| peptide 179 | AAKGEA | SEQ ID NO. 179 |
| peptide 198 | AAKGE | SEQ ID NO. 198 |
| peptide 218 | AAKG | SEQ ID NO. 218 |
| peptide 45 | AKGEAAAERPGEAAVA | SEQ ID NO. 45 |
| peptide 54 | AKGEAAAERPGEAAV | SEQ ID NO. 54 |
| peptide 64 | AKGEAAAERPGEAA | SEQ ID NO. 64 |
| peptide 75 | AKGEAAAERPGEA | SEQ ID NO. 75 |
| peptide 87 | AKGEAAAERPGE | SEQ ID NO. 87 |
| peptide 100 | AKGEAAAERPG | SEQ ID NO. 100 |
| peptide 114 | AKGEAAAERP | SEQ TD NO. 114 |
| peptide 129 | AKGEAAAER | SEQ ID NO. 129 |
| peptide 145 | AKGEAAAE | SEQ ID NO. 145 |
| peptide 162 | AKGEAAA | SEQ ID NO. 162 |
| peptide 180 | AKGEAA | SEQ ID NO. 180 |
| peptide 199 | AKGEA | SEQ ID NO. 199 |
| peptide 219 | AKGE | SEQ ID NO. 219 |
| peptide 55 | KGEAAAERPGEAAVA | SEQ ID NO. 55 |
| peptide 65 | KGEAAAERPGEAAV | SEQ ID NO. 65 |
| peptide 76 | KGEAAAERPGEAA | SEQ ID NO. 76 |
| peptide 88 | KGEAAAERPGEA | SEQ ID NO. 88 |
| peptide 101 | KGEAAAERPGE | SEQ ID NO. 101 |
| peptide 115 | KGEAAAERPG | SEQ ID NO. 115 |
| peptide 130 | KGEAAAERP | SEQ ID NO. 130 |
| peptide 146 | KGEAAAER | SEQ ID NO. 146 |
| peptide 163 | KGEAAAE | SEQ ID NO. 163 |
| peptide 181 | KGEAAA | SEQ ID NO. 181 |
| peptide 200 | KGEAA | SEQ ID NO. 200 |
| peptide 220 | KGEA | SEQ ID NO. 220 |
| peptide 66 | GEAAAERPGEAAVA | SEQ ID NO. 66 |
| peptide 77 | GEAAAERPGEAAV | SEQ ID NO. 77 |
| peptide 89 | GEAAAERPGEAA | SEQ ID NO. 89 |
| peptide 102 | GEAAAERPGEA | SEQ ID NO. 102 |
| peptide 116 | GEAAAERPGE | SEQ ID NO. 116 |
| peptide 131 | GEAAAERPG | SEQ ID NO. 131 |
| peptide 147 | GEAAAERP | SEQ ID NO. 147 |
| peptide 164 | GEAAAER | SEQ ID NO. 164 |
| peptide 182 | GEAAAE | SEQ ID NO. 182 |
| peptide 201 | GEAAA | SEQ ID NO. 201 |
| peptide 221 | GEAA | SEQ ID NO. 221 |
| peptide 78 | EAAAERPGEAAVA | SEQ ID NO. 78 |
| peptide 90 | EAAAERPGEAAV | SEQ ID NO. 90 |
| peptide 103 | EAAAERPGEAA | SEQ ID NO. 103 |
| peptide 117 | EAAAERPGEA | SEQ ID NO. 117 |
| peptide 132 | EAAAERPGE | SEQ ID NO. 132 |
| peptide 148 | EAAAERPG | SEQ ID NO. 148 |
| peptide 165 | EAAAERP | SEQ ID NO. 165 |
| peptide 183 | EAAAER | SEQ ID NO. 183 |
| peptide 202 | EAAAE | SEQ ID NO. 202 |
| peptide 222 | EAAA | SEQ ID NO. 222 |
| peptide 91 | AAAERPGEAAVA | SEQ ID NO. 91 |
| peptide 104 | AAAERPGEAAV | SEQ ID NO. 104 |
| peptide 118 | AAAERPGEAA | SEQ ID NO. 118 |
| peptide 133 | AAAERPGEA | SEQ ID NO. 133 |
| peptide 149 | AAAERPGE | SEQ ID NO. 149 |
| peptide 166 | AAAERPG | SEQ ID NO. 166 |
| peptide 184 | AAAERP | SEQ ID NO. 184 |
| peptide 203 | AAAER | SEQ ID NO. 203 |
| peptide 223 | AAAE | SEQ ID NO. 223 |
| peptide 105 | AARPGEAAVA | SEQ ID NO. 105 |
| peptide 119 | AAERPGEAV | SEQ ID NO. 119 |
| peptide 134 | AAERPGEAA | SEQ ID NO. 134 |
| peptide 150 | AAERPGEA | SEQ ID NO. 150 |
| peptide 167 | AAERPGE | SEQ ID NO. 167 |
| peptide 185 | AAERPG | SEQ ID NO. 185 |
| peptide 204 | AAERP | SEQ ID NO. 204 |
| peptide 224 | AAER | SEQ ID NO. 224 |
| peptide 120 | AERPGEAAVA | SEQ ID NO. 120 |
| peptide 135 | AERPGEAAV | SEQ ID NO. 135 |
| peptide 151 | AERPGEAA | SEQ ID NO. 151 |
| peptide 168 | AERPGEA | SEQ ID NO. 168 |
| peptide 186 | AERPGE | SEQ ID NO. 186 |
| peptide 205 | AERPG | SEQ ID NO. 205 |
| peptide 225 | AERP | SEQ ID NO. 225 |
| peptide 136 | ERPGEAAVA | SEQ ID NO. 136 |
| peptide 152 | ERPGEAAV | SEQ ID NO. 152 |
| peptide 169 | ERPGEAA | SEQ ID NO. 169 |
| peptide 187 | ERPGEA | SEQ ID NO. 187 |

TABLE 2-continued

| Peptide No. | Sequence | Sequence ID No. |
|---|---|---|
| peptide 206 | ERPGE | SEQ ID NO. 206 |
| peptide 226 | ERPG | SEQ ID NO. 226 |
| peptide 153 | RPGEAAVA | SEQ ID NO. 153 |
| peptide 170 | RPGEAAV | SEQ ID NO. 170 |
| peptide 188 | RPGEAA | SEQ ID NO. 188 |
| peptide 207 | RPGEA | SEQ ID NO. 207 |
| peptide 227 | RPGE | SEQ ID NO. 227 |
| peptide 171 | PGEAAVA | SEQ ID NO. 171 |
| peptide 189 | PGEAAV | SEQ ID NO. 189 |
| peptide 208 | PGEAA | SEQ ID NO. 208 |
| peptide 228 | PGEA | SEQ ID NO. 228 |
| peptide 190 | GEAAVA | SEQ ID NO. 190 |
| peptide 209 | GEAAV | SEQ ID NO. 209 |
| peptide 229 | GEAA | SEQ ID NO. 229 |
| peptide 210 | EAAVA | SEQ ID NO. 210 |
| peptide 230 | EAAV | SEQ ID NO. 230 |
| peptide 231 | AAVA | SEQ ID NO. 231 |

Figure 2A:
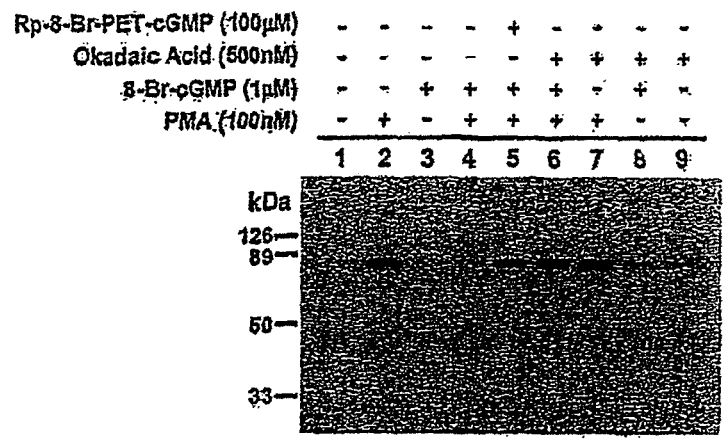
FIGS. 2A-2C show that PKG induces dephosphorylation of MARCKS by activating PP2A.
Figure 2B:
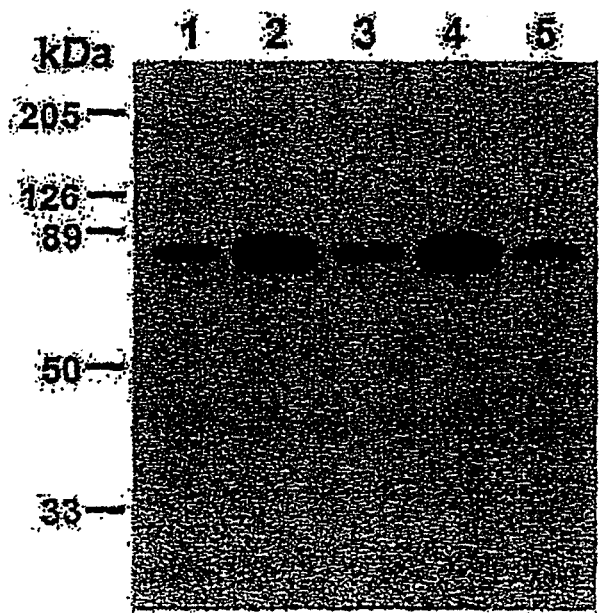
Figure 2C:
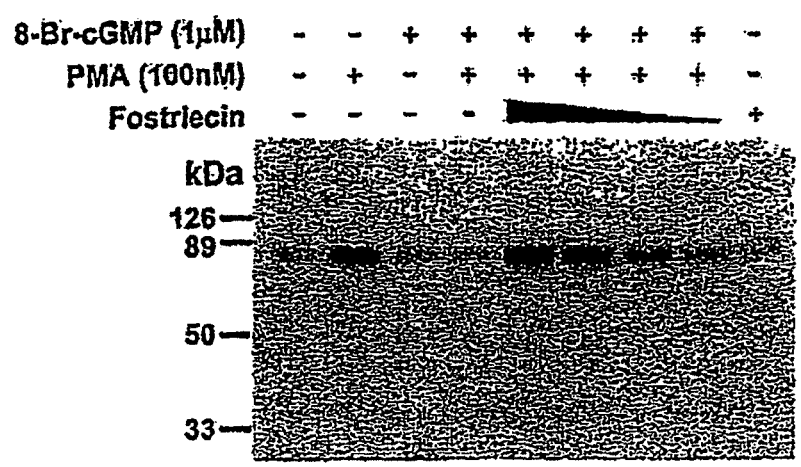
Figure 5:
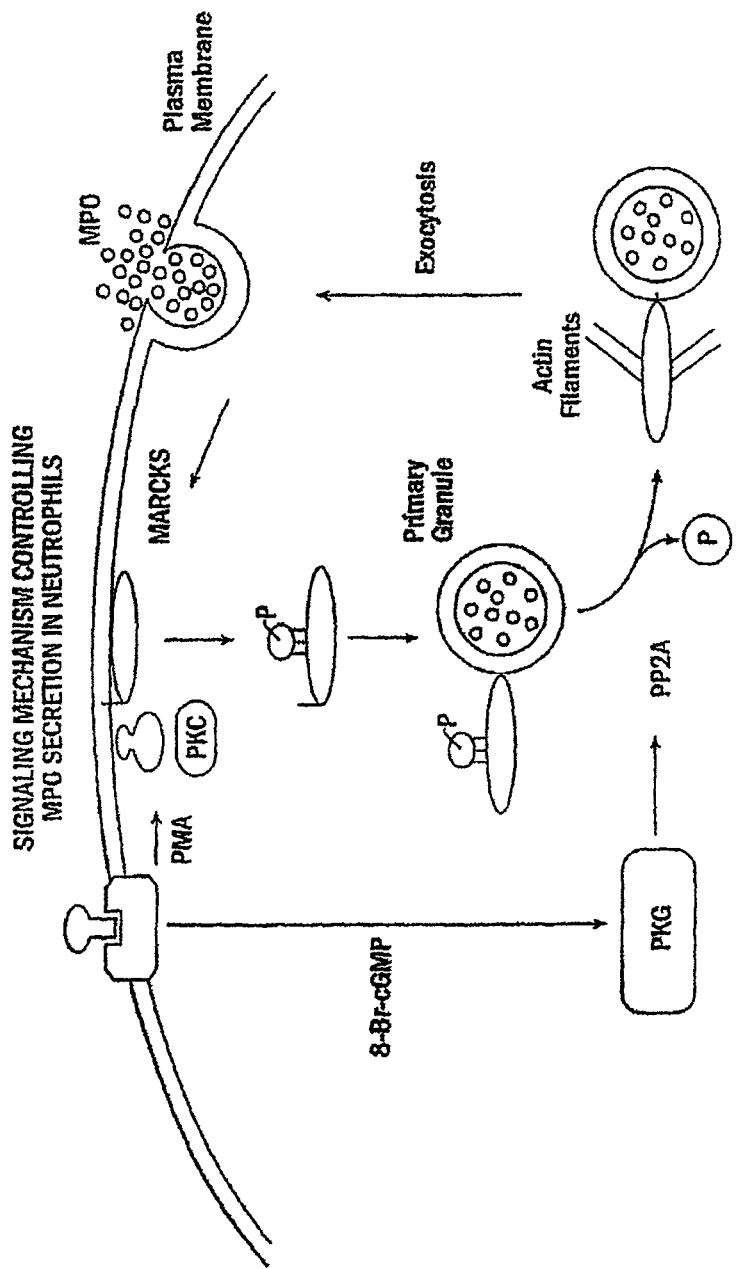
FIG. 5 depicts a signaling mechanism controlling MPO secretion in neutrophils.
Figure 8:
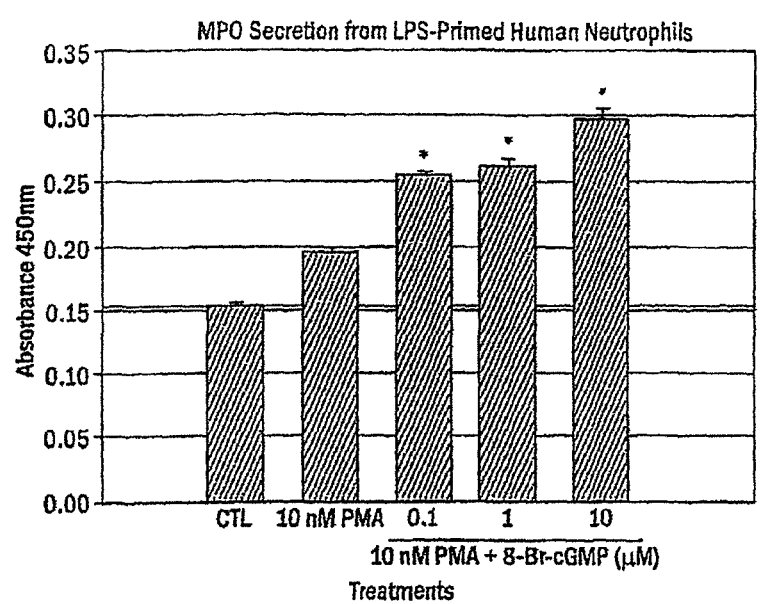
FIG. 8 is a bar graph showing that PMA stimulates a small increase in MPO secretion from LPS-stimulated human neutrophils which is enhanced in a concentration-dependent manner by co-stimulation with 8-Br-cGMP.
Figure 9:
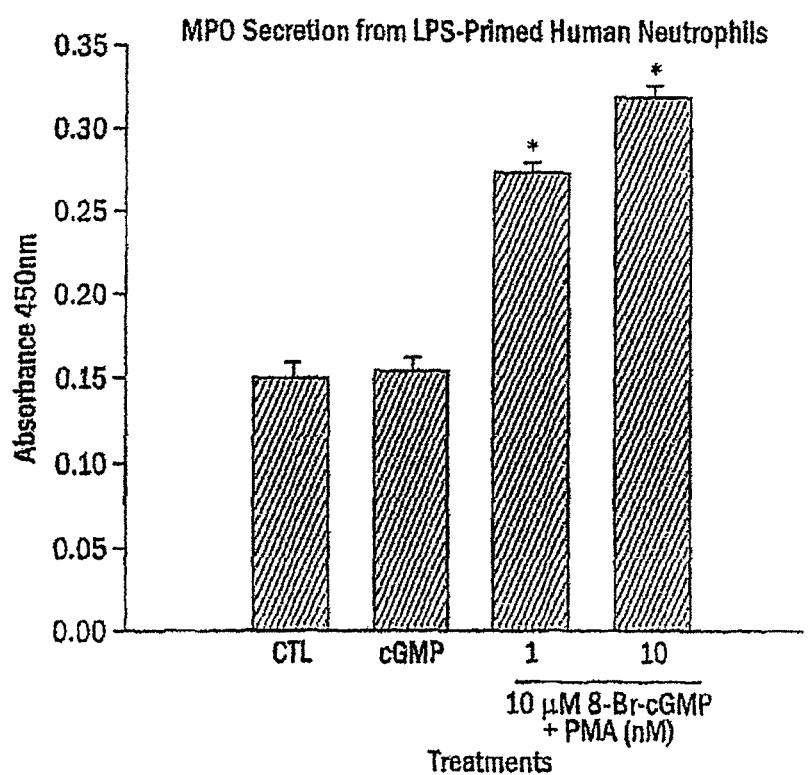
FIG. 9 is a bar graph showing that 8-Br-cGMP simulation has little effect on MPO secretion from LPS-stimulated human neutrophils until a co-stimulation with PMA occurs in a concentration-dependent manner.
Figure 10:
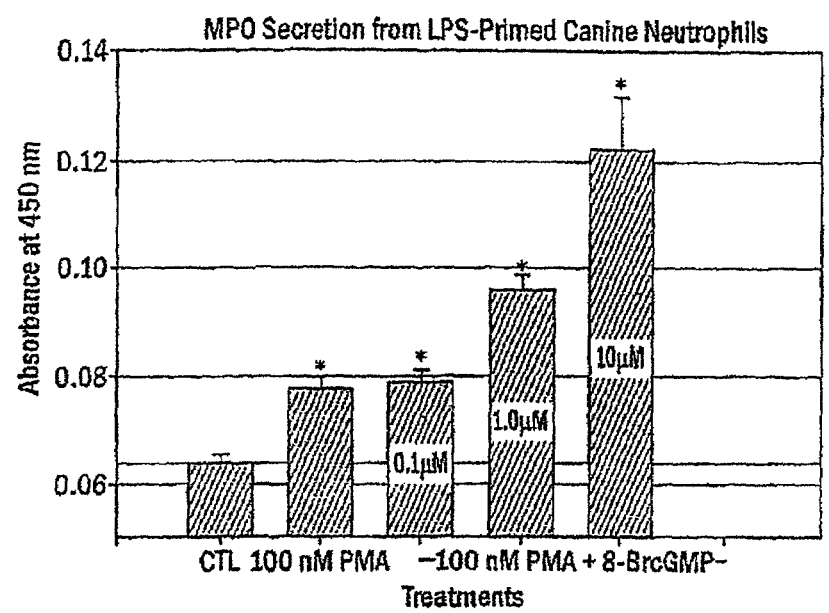
FIG. 10 is a bar graph showing that PMA stimulates a small increase in MPO secretion from LPS-stimulated canine neutrophils which is enhanced in a concentration-dependent manner by co-stimulation with 8-Br-cGMP.
Figure 11:
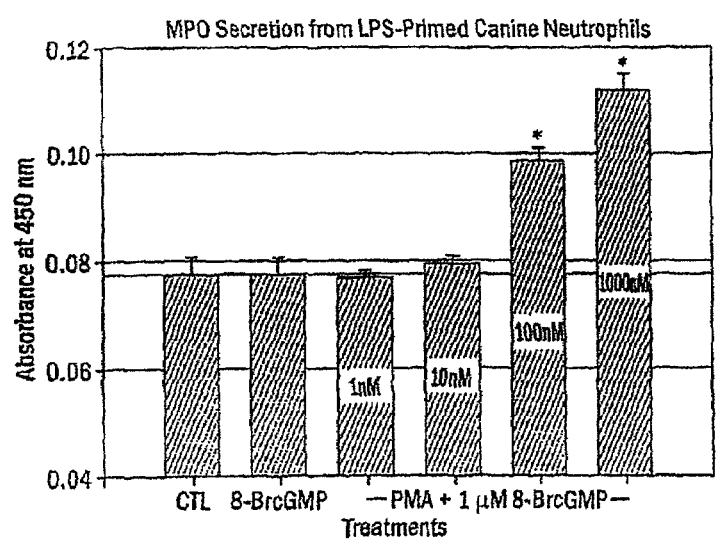
FIG. 11 is a bar graph showing that 8-Br-cGMP simulation has little effect on MPO secretion from LPS-stimulated canine neutrophils until a co-stimulation with PMA occurs in a concentration-dependent manner.
Figure 12:
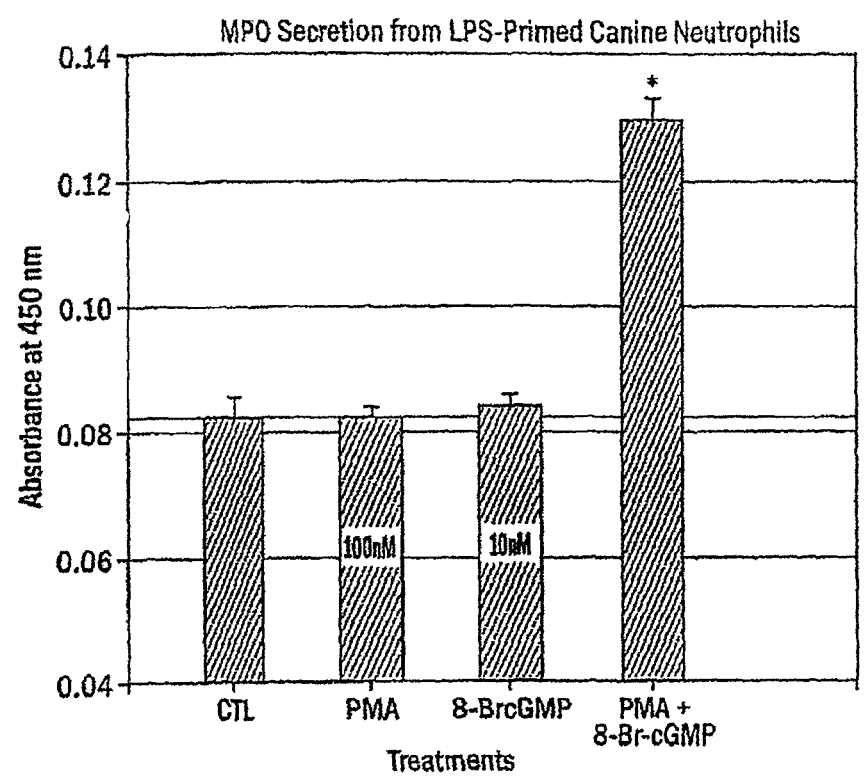
FIG. 12 is a bar graph showing that co-stimulation with PMA+8-Br-cGMP is required for maximal MPO secretion from LPS-stimulated canine neutrophils.

As illustrated in FIG. 5, MARCKS was phosphorylated by PKC and consequently translocated from the membrane to the cytoplasm. Here, PKG appeared to induce dephosphorylation of MARCKS (FIG. 2A, lane 4, and FIG. 2B). This dephosphorylation was reversed by the PKG inhibitor $R_p$-8-Br-PET-cGMP (FIG. 2A, lane 5), indicating the dephosphorylation was specifically PKG-dependent. In FIG. 2, the NHBE cells were labeled with [$^{32}$P]orthophosphate and then exposed to the indicated reagents. MARCKS phosphorylation in response to the treatments was evaluated by immunoprecipitation assay. In FIG. 2A, 8-Br-cGMP reversed MARCKS phosphorylation induced by PMA, and this effect of 8-Br-cGMP could be blocked by $R_p$-8-Br-PET-cGMP (PKG inhibitor) or okadaic acid (PP1/2A inhibitor). For FIG. 2B, PMA-induced phosphorylation of MARCKS was reversed by subsequent exposure of cells to 8-Br-cGMP. Lane 1, medium alone for 8 min; lane 2, 100 nM PMA for 3 min; lane 3, 100 nM PMA for 3 min and then with 1 μM 8-Br-cGMP for 5 min; lane 4, 100 nM PMA for 8 min; lane 5, medium alone for 3 min and then 100 nM PMA+1 μM 8-Br-cGMP for 5 min. In FIG. 2C, 8-Br-cGMP-induced MARCKS dephosphorylation was attenuated by fostriecin in a concentration-dependent manner.

Figure 3:
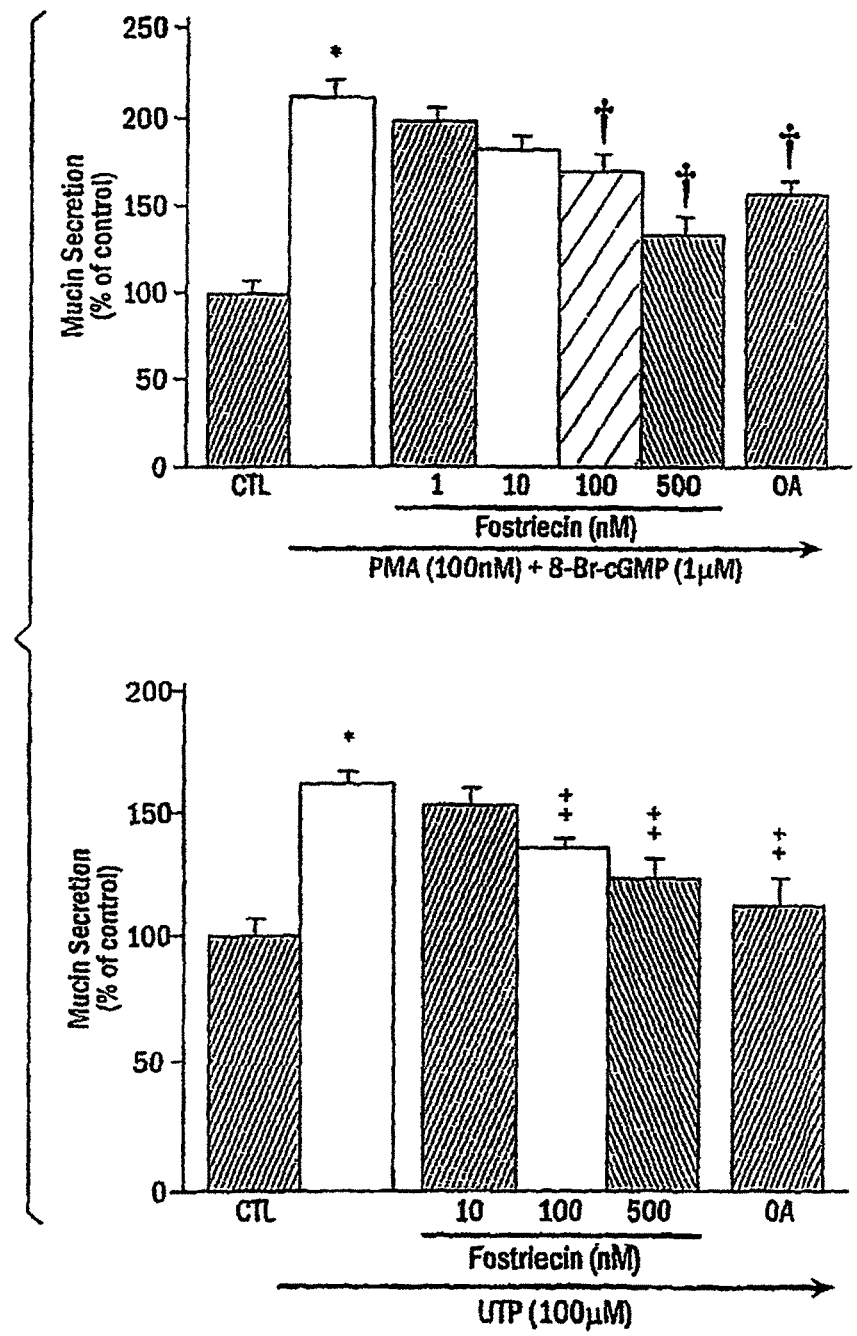
FIG. 3 depicts bar graphs that demonstrate that PP2A is an essential component of the mucin secretory pathway.

It is believed that PKG acts to dephosphorylate MARCKS via activation of a protein phosphatase. As illustrated in FIG. 2A (lane 6), okadaic acid at 500 nM, a concentration that could inhibit both PP1 and PP2A, blocked PKG-induced dephosphorylation of MARCKS, suggesting that PKG caused dephosphorylation by activating PP1 and/or PP2A. Further studies with fostriecin and direct assay of phosphatase activities indicated that only PP2A was activated by PKG and was responsible for removal of the phosphate groups from MARCKS (FIG. 2C). It is likely that either okadaic acid or fostriecin, at concentrations that inhibited PKG-induced dephosphorylation of MARCKS, attenuated mucin secretion induced by PMA+8-Br-cGMP or UTP as exhibited in FIG. 3. FIG. 3 helps to demonstrate that PP2A is an essential component of the mucin secretory pathway. NHBE cells were preincubated with the indicated concentration of fostriecin, okadaic acid (500 nM), or medium alone for 15 min and then stimulated with PMA (100 nM)+8-Br-cGMP (1 μM) for 15 min or with UTP (100 μM) for 2 h. Secreted mucin was measured by ELISA. Data are presented as mean.+−.S.E. (n=6 at each point) wherein * stands for significantly different from medium control (p<0.05); † stands for significantly different from PMA+8-Br-cGMP stimulation (p<0.05); and ‡ stands for significantly different from UTP stimulation p<0.05). Thus, dephosphorylation of MARCKS by a PKG-activated PP2A appears to be an essential component of the signaling pathway leading to mucin granule exocytosis.

Figure 1B:
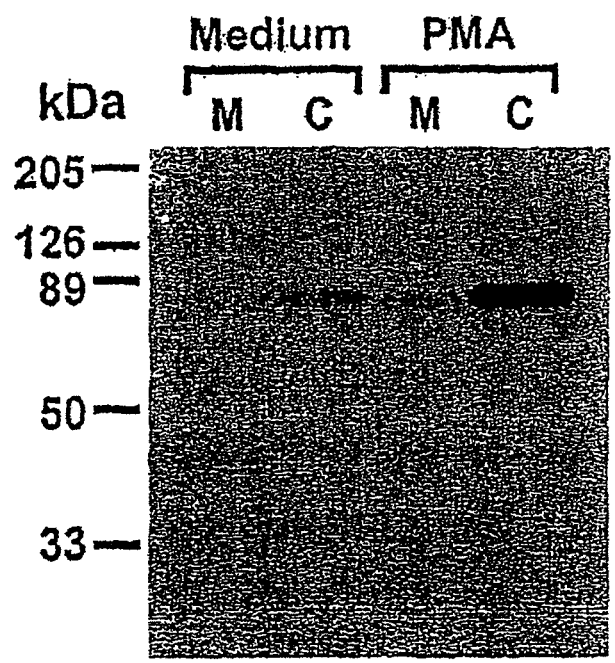

To reveal molecular events by which MARCKS links kinase activation to mucin secretion, phosphorylation of MARCKS in response to PKC/PKG activation was investigated in depth. As illustrated in FIG. 1A, PMA (100 nM) likely induced a significant increase (3-4-fold) in MARCKS phosphorylation in NHBE cells, and this phosphorylation was attenuated by the PKC inhibitor calphostin C (500 nM). Once phosphorylated, MARCKS was translocated from the plasma membrane to the cytoplasm (FIG. 1B). More specifically, FIG. 1A shows the activation of PKC results in MARCKS phosphorylation in NHBE cells. Cells were labeled with [$^{32}$P]orthophosphate for 2 h and then exposed to the stimulatory and/or inhibitory reagents. MARCKS phosphorylation in response to the treatments was evaluated by immunoprecipitation as described. Lane 1, medium control; lane 2 the vehicle, 0.1% Me.sub.2SO; lane 3, 100 nM 4α-PMA; lane 4, 100 nM PMA; lane 5, 100 nM PMA+500 nM calphostin C; lane 6, 500 nM calphostin C. FIG. 1B demonstrates phosphorylated MARCKS is translocated from the plasma membrane to the cytoplasm. $^{32}$P-Labeled cells were exposed to PMA (100 nM) or medium alone for 5 min. and then the membrane and the cytosol fractions were isolated. Activation of PKG by 8-Br-cGMP (1 μM, another kinase activation event necessary for provoking mucin secretion, did not lead to MARCKS phosphorylation, but, in fact, the opposite effect was observed: MARCKS phosphorylation induced by PMA was reversed by 8-Br-cGMP (FIG. 2A). This effect of 8-Br-cGMP was not due to suppression of PKC activity, as the PMA-induced phosphorylation could be reversed by subsequent addition of 8-Br-cGMP to the cells (FIG. 2B). Therefore, PKG activation likely results in dephosphorylation of MARCKS.

Further investigation demonstrated that PKG-induced MARCKS dephosphorylation was blocked by 500 nM okadaic acid, a protein phosphatase (type 1 and/or 2A (PP1/2A)) inhibitor (FIG. 2A, lane 6). Thus, it appeared that the dephosphorylation was mediated by PP1 and/or PP2A. To define the subtype of protein phosphatase involved, a novel and more specific inhibitor of PP2A, fostriecin (IC$_{50}$=3.2 nM), was utilized in additional phosphorylation studies. As illustrated in FIG. 2C, fostriecin inhibited PKG-induced MARCKS dephosphorylation in a concentration-dependent manner (1-500 nM), suggesting that PKG induced the dephosphorylation via activation of PP2A. To confirm further activation of PP2A by PKG in NHBE cells, cytosolic PP1 and PP2A activities were determined after exposure of the cells to 8-Br-cGMP. PP2A activity was increased approximately 3-fold (from 0.1 to 0.3 nmol/min/mg proteins, p<0.01) at concentrations of 8-Br-cGMP as low as 0.1 .mu·M, whereas PP1 activity remained unchanged. This data indicates that PP2A may be activated by PKG and is responsible for the dephosphorylation of MARCKS. Accordingly, this PP2A activity appeared critical for mucin secretion to occur; when PKG-induced MARCKS dephosphorylation was blocked by okadaic acid or fostriecin, the secretory response to PKC/PKG activation or UTP stimulation was ameliorated (FIG. 3).

MARCKS Associates with Actin and Myosin in the Cytoplasm

Figure 4:
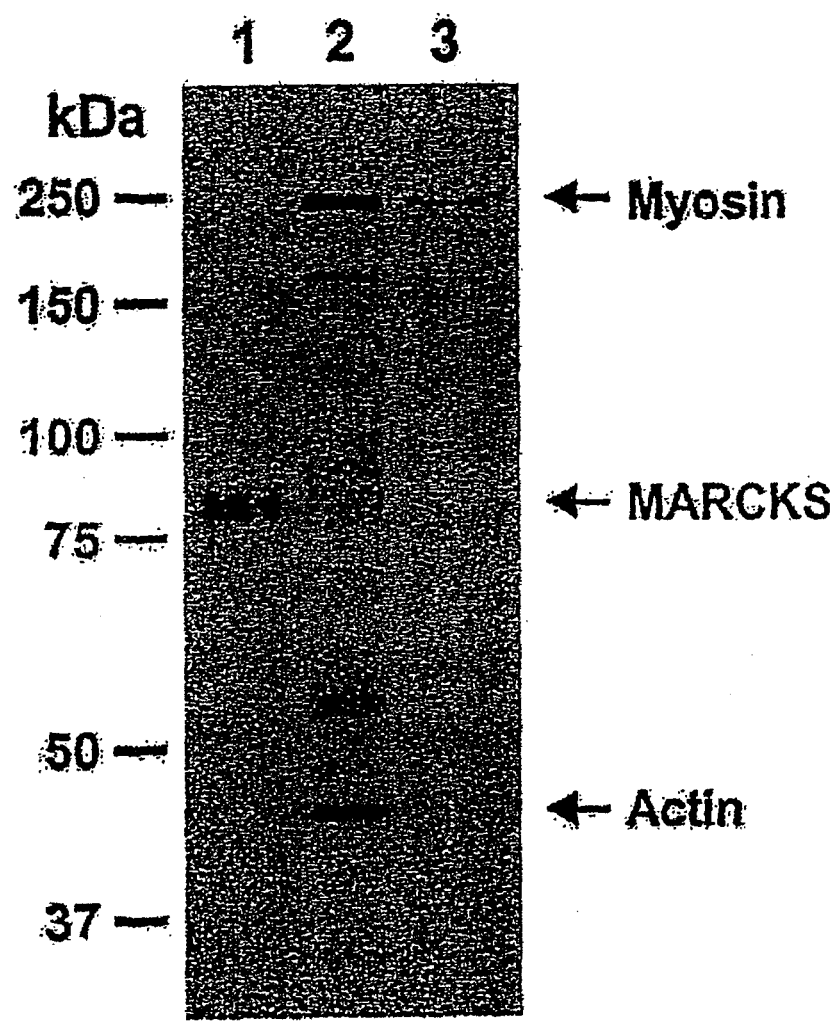
FIG. 4 is a gel that illustrates that MARCKS associates with actin and myosin in the cytoplasm.

FIG. 4 depicts a radiolabeled immunoprecipitation assay which reveals that MARCKS may associate with two other proteins (about 200 and about 40 kDa) in the cytoplasm. In FIG. 4 NHBE cells were labeled with [$^3$H]leucine and [$^3$H] proline overnight, and the membrane and the cytosol fractions were prepared as described under "Experimental Procedures." Isolated fractions were precleared with the nonimmune control antibody (6F6). The cytosol was then divided equally into two fractions and used for immunoprecipitation carried out in the presence of 10 µM cytochalasin D (Biomol, Plymouth Meeting, Pa.) with the anti-MARCKS antibody 2F12 (lane 2) and the nonimmune control antibody 6F6 (lane 3), respectively. MARCKS protein in the membrane fraction was also assessed by immunoprecipitation using the antibody 2F12 (lane 1). The precipitated protein complex was resolved by 8% SDS-polyacrylamide gel electrophoresis and visualized by enhanced autoradiography. MARCKS appeared to associate with two cytoplasmic proteins with molecular masses of about 200 and about 40 kDa, respectively. These two MARCKS-associated proteins were excised from the gel and analyzed by matrix-assisted laser desorption ionization/time of flight mass spectrometry/internal sequencing (the Protein/DNA Technology Center of Rockefeller University, N.Y.). The obtained peptide mass and sequence data were used to search protein databases via Internet programs ProFound and MS-Fit. Results indicate that they are myosin (heavy chain, non-muscle type A) and actin, respectively. Matrix-assisted laser desorption ionization/time of flight mass spectrometry/internal sequence analysis indicates that these two MARCKS-associated proteins were myosin (heavy chain, non-muscle type A) and actin, respectively.

These studies suggest a new paradigm for the signaling mechanism controlling exocytotic secretion of airway mucin granules as well as providing what is believed to be the first direct evidence demonstrating a specific biological function of MARCKS in a physiological process. MARCKS serves as a key mediator molecule regulating mucin granule release in human airway epithelial cells. It is believed that elicitation of airway mucin secretion requires dual activation and synergistic actions of PKC and PKG. Activated PKC phosphorylates MARCKS, resulting in translocation of MARCKS from the inner face of the plasma membrane into the cytoplasm. Activation of PKG in turn activates PP2A, which dephosphorylates MARCKS in the cytoplasm. Because the membrane association ability of MARCKS is dependent on its phosphorylation state this dephosphorylation may allow MARCKS to regain its membrane-binding capability and may enable MARCKS to attach to membranes of cytoplasmic mucin granules. By also interacting with actin and myosin in the cytoplasm (FIG. 4), MARCKS may then be able to tether granules to the cellular contractile apparatus, mediating granule movement to the cell periphery and subsequent exocytotic release. The wide distribution of MARCKS suggests the possibility that this or a similar mechanism may regulate secretion of membrane-bound granules in various cell types under normal or pathological conditions.

As indicated in FIG. 5, MARCKS may function as a molecular linker by interacting with granule membranes at its N-terminal domain and binding to actin filaments at its PSD site, thereby tethering granules to the contractile cytoskeleton for movement and exocytosis. FIG. 5 shows a possible mechanism depicting that mucin secretagogue interacts with airway epithelial (goblet) cells and activates two separate protein kinases, PKC and PKG. Activated PKC phosphorylates MARCKS, causing MARCKS translocation from the plasma membrane to the cytoplasm, whereas PKG, activated via the nitric oxide (NO)→GC-S→cGMP→PKG pathway, in turn activates a cytoplasmic PP2A, which dephosphorylates MARCKS. This dephosphorylation stabilizes MARCKS attachment to the granule membranes. In addition, MARCKS also interacts with actin and myosin, thereby linking granules to the cellular contractile machinery for subsequent movement and exocytotic release of inflammatory mediators, such as MPO. The attachment of MARCKS to the granules after it is released into the cytoplasm may also be guided by specific targeting proteins or some other forms of protein-protein interactions in which the N-terminal domain of MARCKS is involved. In either case, the MANS peptide, or an active fragment thereof, comprising at least 4 amino acids, would act to inhibit competitively targeting of MARCKS to the membranes of mucin granules, thereby blocking secretion.

Figure 6:
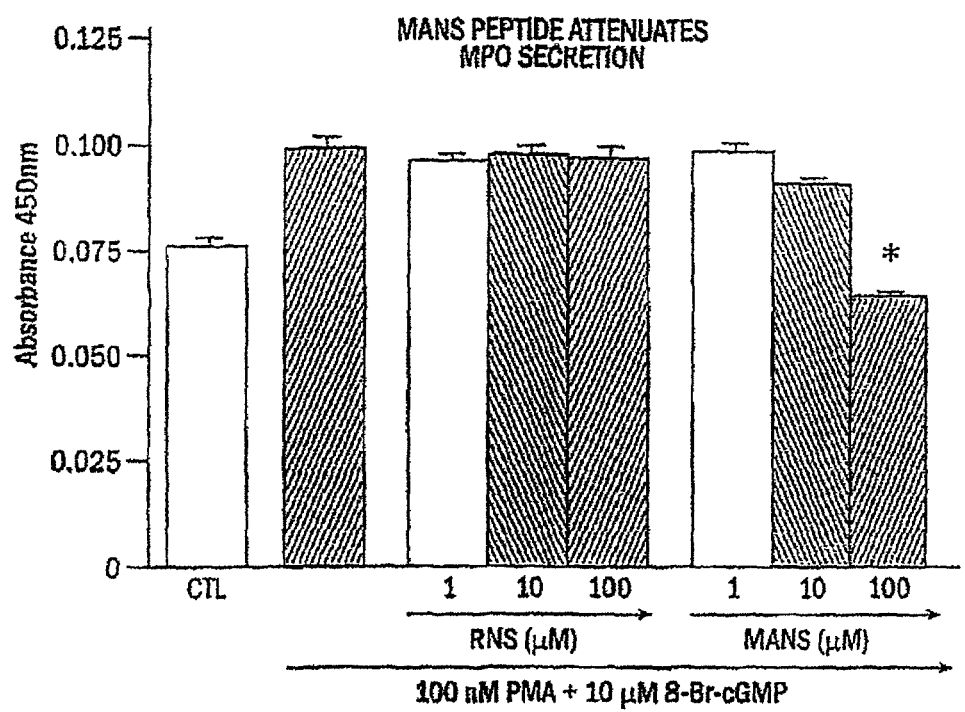
FIG. 6 is a bar graph depicting the ability of MANS peptide to block secretion of myloperoxidase from isolated canine neutrophils.
Figure 7:
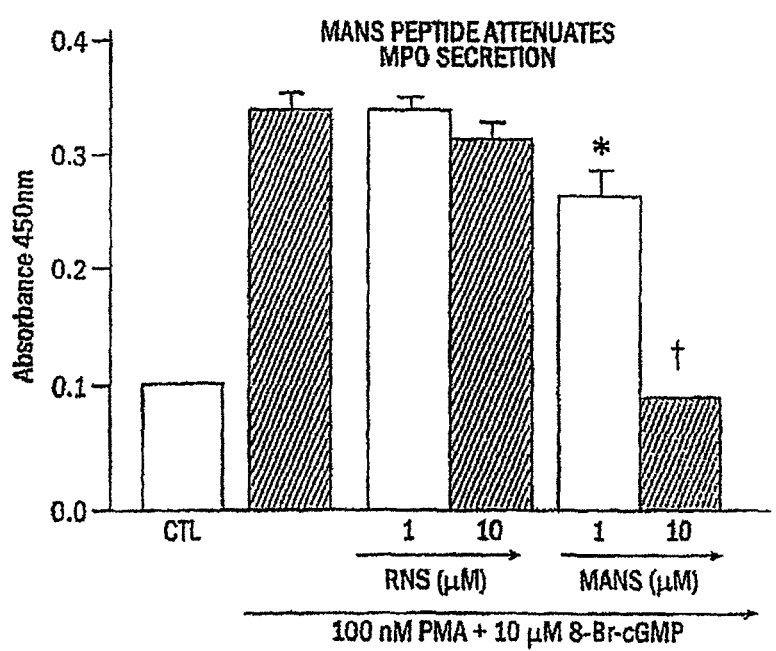
FIG. 7 is a bar graph depicting the ability of MANS peptide to block secretion of myloperoxidase from isolated human neutrophils.

The invention also relates to a new method for blocking any cellular exocytotic secretory process, especially those releasing inflammatory mediators from granules contained within inflammatory cells, whose stimulatory pathways involve the protein kinase C (PKC) substrate MARCKS protein and release of contents from membrane-bound vesicles. Specifically, the inventors have shown that stimulated release of the inflammatory mediator myloperoxidase from human (FIG. 6) or canine (FIG. 7) neutrophils can be blocked in a concentration-dependent manner by the MANS peptide. Specifically, FIG. 6 shows isolated neutrophils that were stimulated to secrete myloperoxidase (MPO) with 100 nM PMA and 10 .mu·M 8-Br-cGMP. 100 µM MANS peptide decreased secretion of MPO to control levels (*=p<0.05). 10 µM MANS causes a slight decrease in MPO secretion. 10 or 100 µM of a control peptide (RNS) has no effect on MPO secretion. In FIG. 7, isolated neutrophils were stimulated to secrete myloperoxidase (MPO) with 100 nM PMA and 10 µM 8-Br-cGMP. 100 µM MANS peptide decreased secretion of MPO to control levels (*=p<0.05). 10 µM MANS causes a slight decrease in MPO secretion. 10 or 100 µM of a control peptide (RNS) has no effect on MPO secretion. Thus, the peptide may be used therapeutically to block the release of mediators of inflammation secreted from infiltrating inflammatory cells in any tissues. Many of these released mediators are responsible for the extensive tissue damage observed in a variety of chronic inflammatory diseases (i.e., respiratory diseases such as asthma, chronic bronchitis and COPD, inflammatory bowel diseases including ulcerative colitis and Crohn's disease, autoimmune diseases, skin diseases such as rosacea, eczema; and severe acne, arthritic and pain syndromes such as rheumatoid arthritis and fibromyalgia). This invention may be useful for treating diseases such as arthritis, chronic bronchitis, COPD and cystic fibrosis. This invention is accordingly useful for the treatment in both human and animal diseases, especially those affecting equines, canines, felines, and other household pets.

FIGS. 8-12 show MPO secretion for both humans and canines. In all of these experiments, isolated neutrophils were stimulated with LPS at a concentration of $1\times10^{-6}$ M for 10 minutes at 37° C. prior to adding the stimuli as indicated in the figures. The LPS primes the cells so they can respond to a secretagogue.

In one embodiment, this invention discloses a method of regulating an inflammation in a subject comprising administering a therapeutically effective amount of a pharmaceutical composition comprising a MANS peptide or an active fragment thereof. In one aspect of this embodiment, said active fragment of the MANS protein comprises at least four and preferably six amino acids. In another aspect, said inflammation is caused by respiratory diseases, bowel diseases, skin diseases, autoimmune diseases and pain syndromes. In another aspect, said respiratory diseases are selected from the group consisting of asthma, chronic bronchitis, and COPD. In another aspect, said bowel diseases are selected from the group consisting of ulcerative colitis, Crohn's disease and irritable bowel syndrome. In another aspect, said skin diseases are selected from the group consisting of rosacea, eczema, psoriasis and severe acne. In another aspect, said inflammation is caused by arthritis or cystic fibrosis. In another aspect, said subject is a mammal. Additionally, in another aspect, said mammal is selected from the group consisting of humans, canines, equines and felines. In another aspect, said administering step is selected from the group consisting of topical administration, parenteral administration, rectal administration, pulmonary administration, nasal administration, inhalation and oral administration. In another aspect, said pulmonary administration is selected from the group of aerosol, dry powder inhaler, metered dose inhaler, and nebulizer.

In another embodiment, this invention discloses a method for regulating a cellular secretory process in a subject comprising administering a therapeutically effective amount of a pharmaceutical composition comprising at least one compound comprising a MANS peptide or an active fragment thereof, that regulates an inflammatory mediator in a subject. In one aspect of this embodiment, said active fragment of the MANS protein comprises at least four, and preferably six amino acids. In another aspect, said regulating a cellular secretory process is blocking or reducing a cellular secretory process. In another aspect, said inflammatory mediator is caused by respiratory diseases, bowel diseases, skin diseases, autoimmune diseases and pain syndromes. In another aspect, said respiratory diseases are selected from the group consisting of asthma, chronic bronchitis, and COPD. In another aspect, said bowel diseases are selected from the group consisting of ulcerative colitis, Crohn's disease and irritable bowel syndrome. In another aspect, said skin diseases are selected from the group consisting of rosacea, eczema, psoriasis and severe acne. In another aspect, said inflammatory mediator is caused by arthritis or cystic fibrosis. In another aspect, said subject is a mammal. In another aspect, said mammal is selected from the group consisting of humans, canines, equines and felines. In another aspect, said administering step is selected from the group consisting of topical administration, parenteral administration, rectal administration, pulmonary administration, nasal administration, inhalation and oral administration. In another aspect, said pulmonary administration is selected from the group of aerosol, dry powder inhaler, metered dose inhaler, and nebulizer.

In another embodiment, this invention discloses a method of reducing inflammation in a subject comprising administering a therapeutically effective amount of a compound that inhibits the MARCKS-related release of inflammatory mediators, whereby the release of inflammatory mediators in the subject is reduced compared to that which would occur in the absence of said treatment. In one aspect of this embodiment, said compound is at least one active fragment of a MARCKS protein. In another aspect, said active fragment is at least four and preferably six amino acids in length. In another aspect, said compound is a MANS peptide or an active fragment thereof. In another aspect, said compound is an antisense oligonucleotide directed against the coding sequence of a MARCKS protein or an active fragment thereof. In another aspect, said active fragment is at least four and preferably six amino acids in length.

In another embodiment, this invention discloses a method of reducing inflammation in a subject comprising administering a therapeutically effective amount of a pharmaceutically active composition comprising a compound that inhibits the MARCKS-related release of inflammatory mediators, whereby the inflammation in the subject is reduced compared to that which would occur in the absence of said treatment. In one aspect of this embodiment, said compound is an active fragment of a MARCKS protein. In another aspect, said active fragment is at least four and preferably six amino acids in length. In another aspect, said compound is a MANS peptide or an active fragment thereof. In another aspect, said compound is an antisense oligonucleotide directed against the coding sequence of a MARCKS protein or an active fragment thereof. In another aspect, said active fragment is at least four and preferably six amino acids in length. The present invention is intended to encompass a composition that contains one or more of the MANS peptide or its active fragments and use thereof in the treatment of inhibiting the release of inflammatory mediators from granules or vesicles of inflammatory cells.

In another embodiment, this invention discloses a method of reducing or inhibiting inflammation in a subject comprising administering a therapeutically effective amount of at least one peptide comprising MANS peptide or an active fragment thereof effective to inhibit or suppress release of an inflammatory mediator at the inflammation site. In one aspect of this embodiment, said active fragment is at least four and preferably at least six amino acids in length. In another aspect, said inflammatory mediators are produced by cells selected from the group consisting of neutrophils, basophils, eosinophils, monocytes and leukocytes. Preferably the cells are leukocytes, more preferably granulocytes, and even more preferably neutrophils, basophils, eosinophils or a combination thereof. In another aspect, the agent is administered orally, parenterally, cavitarily, rectally or through an air passage. In another aspect, said composition further comprises a second molecule selected from the group consisting of an antibiotic, an antiviral compound, an antiparasitic compound, an anti-inflammatory compound, and an immunosuppressant.

An active fragment of a MANS peptide can be selected from the group consisting of the peptides of disclosed in Table 1. As disclosed herein, these peptides may be contain optional chemical moieties at the N-terminal and/or C-terminal amino acid.

In another aspect of this invention, the methods disclosed in this invention can be accomplished by use of or administering of combinations of the peptides disclosed in the invention in Table 1, i.e., by use of or administering of one or more of these peptides. Preferably a single peptide is used or administered in the methods disclosed herein.

In response to protein kinase C (PKC) activation by an inflammatory stimulant, degranulation in a cell selected from the group consisting of neutrophils, eosinophils, monocytes/macrophages and lymphocytes can be attenuated by pre-incubation and by co-incubation with a peptide identical to the N-terminal region of MARCKS protein, wherein the peptide is selected from the group of MANS peptide fragments as disclosed in Table 1. Although time courses and concentrations can vary among cell types, in all cases the MANS peptide attenuates PKC-induced degranulation.

Having now described the invention, the same will be illustrated with reference to certain examples, which are included herein for illustration purposes only, and which are not intended to be limiting of the invention.

EXAMPLES

Methods and Materials

Radiolabeled Immunoprecipitation Assay—When labeling with [$^{32}$P]phosphate, cells were preincubated for 2 h in phosphate-free Dulbecco's modified Eagle's medium containing 0.2% bovine serum albumin and then labeled with 0.1 mCi/ml [$^{32}$P]orthophosphate (9000 Ci/mmol, PerkinElmer Life Sciences) for 2 h. For labeling with [$^3$H]myristic acid or $^3$H-amino acids, cells were incubated overnight in medium containing 50 μCi/ml [$^3$H]myristic acid (49 Ci/mmol, PerkinElmer Life Sciences) or 0.2 mCi/ml [$^3$H]leucine (159 Ci/mmol, PerkinElmer Life Sciences) plus 0.4 mCi/ml [$^3$H] proline (100 Ci/mmol, PerkinElmer Life Sciences). Following labeling, cells were exposed to stimulatory reagents for 5 min. When an inhibitor was used, cells were preincubated with the inhibitor for 15 min prior to stimulation. At the end of the treatments, cells were lysed in a buffer containing 50 mM Tris-HCl (pH 7.5), 150 mM NaCl, 1 mM EDTA, 10% glycerol, 1% Nonidet P-40, 1 mM phenylmethylsulfonyl fluoride, 1 mM benzamidine, 10 μg/ml pepstatin A, and 10 μg/ml leupeptin. Trichloroacetic acid precipitation and scintillation counting may determine the radiolabeling efficiency in each culture. Immunoprecipitation of MARCKS protein was carried out according to the method of Spizz and Blackshear using cell lysates containing equal counts/min. Spizz et al., *J. Biol. Chem.* 271, 553-562 (1996). Precipitated proteins were resolved by 8% SDS-polyacrylamide gel electrophoresis and visualized by autoradiography. Anti-human MARCKS antibody (2F12) and nonimmune control antibody (6F6) were used in this assay.

To assess MARCKS or MARCKS-associated protein complexes in different subcellular fractions, radiolabeled and treated cells were scraped into a homogenization buffer (50 mM Tris-HCl (pH 7.5), 10 mM NaCl, 1 mM EDTA, 1 mM phenylmethylsulfonyl fluoride, 1 mM benzamidine, 10 μg/ml pepstatin A, 10 μg/ml leupeptin) and then disrupted by nitrogen cavitation (800 pounds/square inch for 20 min at 4° C.). Cell lysates were centrifuged at 600×g for 10 min at 4° C. to remove nuclei and unbroken cells. Post-nuclear supernatants were separated into membrane and cytosol fractions by ultracentrifugation at 400,000×g for 30 min at 4° C. The membrane pellet was solubilized in the lysis buffer by sonication. Immunoprecipitation was then carried out as described above.

MARCKS-related Peptides—Both the myristoylated N-terminal sequence (MANS) and the random N-terminal sequence (RNS) peptides were synthesized at Genemed Synthesis, Inc. (San Francisco, Calif.), then purified by high pressure liquid chromatography (>95% pure), and confirmed by mass spectroscopy with each showing one single peak with an appropriate molecular mass. The MANS peptide consisted of sequence identical to the first 24 amino acids of MARCKS, i.e. the myristoylated N-terminal region that mediates MARCKS insertion into membranes, MA-GAQFSKTAAKGEAAAERPGEAAVA (SEQ ID NO: 1 (where MA is N-terminal myristoyl chain). The corresponding control peptide (RNS) contained the same amino acid composition as the MANS but arranged in random order, MA-GTA-PAAEGAGAEVKRASAEAKQAF (SEQ ID NO: 232). The presence of the hydrophobic myristate moiety in these synthetic peptides enhances their permeability to the plasma membranes, enabling the peptides to be taken up readily by cells. To determine the effects of these peptides on mucin secretion, cells were preincubated with the peptides for 15 min prior to addition of secretagogues, and mucin secretion was then measured by ELISA.

Antisense Oligonucleotides—MARCKS antisense oligonucleotide and its corresponding control oligonucleotide were synthesized at Biognostik GmbH (Gottingen, Germany). NHBE cells were treated with 5 μM antisense or control oligonucleotide apically for 3 days (in the presence of 2 μg/ml lipofectin for the first 24 h). Cells were then incubated with secretagogues, and mucin secretion was measured by ELISA. Total RNA and protein were isolated from treated cells. MARCKS mRNA was assessed by Northern hybridization according to conventional procedures using human MARCKS cDNA as a probe. MARCKS protein level was determined by Western blot using purified anti-MARCKS IgG1 (clone 2F12) as the primary detection antibody.

Transient Transfection—The phosphorylation site domain (PSD) of MARCKS contains the PKC-dependent phosphorylation sites and the actin filament-binding site. To construct a PSD-deleted MARCKS cDNA, two fragments flanking the PSD sequence (coding for 25 amino acids) were generated by polymerase chain reaction and then ligated through the XhoI site that was attached to the 5'-ends of oligonucleotide primers designed for the polymerase chain reaction. The resultant mutant cDNA and the wild-type MARCKS cDNA were each inserted into a mammalian expression vector pcDNA4/TO (Invitrogen, Carlsbad, Calif.). Isolated recombinant constructs were confirmed by restriction digests and DNA sequencing.

HBE1 is a papilloma virus-transformed human bronchial epithelial cell line capable of mucin secretion when cultured in air/liquid interface. Transfection of HBE1 cells was carried out using the Effectene transfection reagent (Qiagen, Valencia, Calif.) according to the manufacturer's instructions. Briefly, differentiated HBE1 cells grown in air/liquid interface were dissociated by trypsin/EDTA and re-seeded in 12-well culture plates at 1×10$^5$ cells/cm$^2$. After overnight incubation, cells were transfected with the wild-type MARCKS cDNA, the PSD-truncated MARCKS cDNA, or vector DNA. Cells were cultured for 48 h to allow gene expression and then exposed to secretagogues and mucin secretion measured by ELISA. All transfections were carried out in the presence of pcDNA4/TO/lacZ plasmid (Invitrogen) (DNA ratio 6:1, total 1 μg DNA, ratio of DNA to Effectene reagent=1:25) to monitor variations in transfection efficiency. Results showed no significant difference in .beta.-galactosidase activities in cell lysates isolated from the transfected cells, indicating similar transfection efficiency among different DNA constructs (data not shown).

Protein Phosphatase Activity Assay—PP1 and PP2A activities were measured using a protein phosphatase assay system (Life Technologies, Inc.) as known in the art with slight modification. Huang et al., Adv. Exp. Med. Biol. 396, 209-215 (1996). Briefly, NHBE cells were treated with 8-Br-cGMP or medium alone for 5 min. Cells were then scraped into a lysis buffer (50 mM Tris-HCl (pH 7.4), 0.1% .beta.-mercaptoethanol, 0.1 mM EDTA, 1 mM benzamidine, 10 μg/ml pepstatin A, 10 μg/ml leupeptin) and disrupted by sonication for 20 s at 4° C. Cell lysates were centrifuged and the supernatants saved for phosphatase activity assay. The assay was performed using $^{32}$P-labeled phosphorylase A as a substrate. Released $^{32}$P$_i$ was counted by scintillation. The protein concentration of each sample was determined by the Bradford assay. PP2A activity was expressed as the sample total phosphatase activity minus the activity remaining in the presence of 1 nM okadaic acid, PP1 activity was expressed as the difference between the activities remaining in the presence of 1 nM and 1 μM okadaic acid, respectively. Protein phosphatase activities were reported as nmol of $P_i$ released per min/mg total protein.

Cytotoxicity Assay—All reagents used in treating NHBE cells were examined for cytotoxicity by measuring the total release of lactate dehydrogenase from the cells. The assay was carried out using the Promega Cytotox 96 Kit according to the manufacturer's instructions. All experiments were performed with reagents at non-cytotoxic concentrations.

Statistical Analysis—Data were analyzed for significance using one-way analysis of variance with Bonferroni post-test corrections. Differences between treatments were considered significant at $p<0.05$.

Isolation of PMNs from canine blood—The steps involved in isolating PMN include collecting 10 ml ACD anticoagulated blood. Then layering 5 ml on 3.5 ml PMN isolation media while ensuring that the PMN isolation media (IM) was at room temperature (R1). Next, the blood was centrifuged at room temperature for 30', 550×g at 1700 RPMs. The low lower white band was transferred into 15 ml conical centrifuge tube (CCFT). Next, 2V HESS with 10% fetal bovine serum (PBS) was added and centrifuged at room temperature for 10', 400×g at 1400 RPMs. The pellet was then resuspended in 5 ml 1-1ESS with PBS. The cell suspension was added to 50 ml CCFT containing 20 ml of ice cold 0.88% $NH_4Cl$ and inverted two to three times. The resulting product was centrifuged for 10', 800×g at 2000 RPMs, then aspirated and resuspended in 5 ml HBSS with FBS. The prep was examined by counting and cytospin and preferably for whole blood, the cell number should be between $10^9$-$10^{11}$ cells and for PMNs, cell number should be between 2-4×$10^7$ cells. See generally, Wang et al., *J. Immunol.*, "Neutrophil-induced changes in the biomechanical properties of endothelial cells: roles of ICAM-1 and reactive oxygen species," 6487-94 (2000).

MPO Colormetric Enzyme Assay—Samples were assayed for MPO activity in 96 well round bottom microtiter plates using a sandwich ELISA kit (R & D Systems, Minneapolis, Minn.). Briefly, 20 microliters of sample is mixed with 180 microliters of substrate mixture containing 33 mM potassium phosphate, pH 6.0, 0.56% Triton X-100, 0.11 mM hydrogen peroxide, and 0.36 mM O-Diannisidine Dihydrochloride in an individual microtiter well. The final concentrations in the assay mixture are: 30 mM potassium phosphate, pH 6.0, 0.05% Triton X-100, 0.1 mM hydrogen peroxide, and 0.32 mM O-Diannisidine Dihydrochloride. After mixing, the assay mixture was incubated at room temperature for 5 minutes, and MPO enzyme activity determined spectrophotometrically at 550 nanometers. Samples were assayed in duplicate.

Example 1

Inflammatory Mediator Secretion Studies

Four different leukocyte types or models that secrete specific granule contents in response to phorbol ester induced activation of PKC were used. Neutrophils were isolated from human blood and in vitro release of MPO by these cells was assessed. Release of membrane-bound inflammatory mediators from commercially-available human leukocyte cell lines was also evaluated. The human promyelocytic cell line HL-60 clone 15 was used to assess secretion of EPO (Fischkoff SA. Graded increase in probability of eosinophilic differentiation of HL-60 promyelocytic leukemia cells induced by culture under alkaline conditions. Leuk Res 1988; 12:679-686; Rosenberg H F, Ackerman S J, Tenen D G. Human eosinophil cationic protein: molecular cloning of a cytotoxin and helminthotoxin with ribonuclease activity. J Exp Med 1989; 170:163-176; Tiffany H L, Li F, Rosenberg H F. Hyperglycosylation of eosinophil ribonucleases in a promyelocytic leukemia cell line and in differentiated peripheral blood progenitor cells. J Leukoc Biol 1995; 58:49-54; Badewa A P, Hudson C E, Heiman A S. Regulatory effects of eotaxin, eotaxin-2, and eotaxin-3 on eosinophil degranulation and superoxide anion generation. Exp Biol Med 2002; 227:645-651). The monocytic leukemia cell line U937 was used to assess secretion of lysozyme (Hoff T, Spencker T, Emmendoerffer A., Goppelt-Struebe M. Effects of glucocorticoids on the TPA-induced monocytic differentiation. J Leukoc Biol 1992; 52:173-182; Balboa M A, Saez Y, Balsinde J. Calcium-independent phospholipase A2 is required for lysozyme secretion in U937 promonocytes. J Immunol 2003; 170: 5276-5280; Sundstrom C, Nilsson K. Establishment and characterization of a human histiocytic lymphoma cell line (U-937). Int J Cancer 1976; 17:565-577). The lymphocyte natural killer cell line NK-92 used to assess release of granzyme (Gong J H., Maki G, Klingemann H G. Characterization of a human cell line (NK-92) with phenotypical and functional characteristics of activated natural killer cells, Leukemia 1994; 8:652-658; Maki G, Klingemann H G, Martinson J A, Tam Y K. Factors regulating the cytotoxic activity of the human natural killer cell line, NK-92. J Hematother Stem Cell Res 2001; 10:369-383; Takayama H, Trenn G, Sitkovsky M V. A novel cytotoxic T lymphocyte activation assay. J Immunol Methods 1987; 104:183-190). In all cases, the cells were preincubated with a range of concentrations of a synthetic peptide identical to the 24 amino acid MARCKS N-terminus (MANS myristoylated N-terminal sequence peptide; MA-GAQFSKTAAKGEAAAERPGEAAVA (SEQ ID NO:1) wherein MA is myristoyl attached to the N-terminal amine of the peptide by an amide bond), or a missense control peptide (RNS: Random N-terminal sequence peptide; MA-GTAPAAEGAGAEVKRASAEAKQAF, SEQ ID NO: 232) which consists of the same 24 amino acids but arranged in random order sequence which possesses less than 13% sequence identity to the MANS peptide sequence. Alternatively, the cells were pretreated with one of the synthetic truncated peptides listed in Table 3 below.

In each of the cell types, MANS, but not RNS, attenuates release of inflammatory mediators in a concentration-dependent manner. A useful time course of observation is 0.5-3.0 hrs. The results are consistent with the N-terminal region of the MARCKS protein being involved in intracellular pathways leading to leukocyte degranulation.

Human neutrophil isolation—These studies were approved by the human studies Institutional Review Board (IRB). Human neutrophils were isolated as previously described (see Takashi S, Okubo Y, Horie S. Contribution of CD54 to human eosinophil and neutrophil superoxide production. J Appl Physiol 2001; 91:613-622) with slight modifications. Briefly, heparinized venous blood was obtained from normal healthy volunteers, diluted with RPMI-1640 (Cellgro; Mediatech, Inc., Herndon, Va.) at a ratio of 1:1, layered onto a Histopaque (density, 1.077 g/ml; Sigma-Aldrich Co., St. Louis, Mo.) and centrifuged at 400 g for 20 min at 4° C. The supernatant and mononuclear cells at the interface were carefully removed, and erythrocytes in the sediment were lysed in chilled distilled water. Isolated granulocytes were washed twice with Hanks' balanced salts solution (HBSS) and resuspended in HBSS on ice. The neutrophils used for the experiments were of >98% purity with <2% contamination by eosinophils, and the viability was >99% as determined by Trypan blue dye exclusion.

Measurement of released neutrophil MPO activity—For measurement of MPO release, purified human neutrophils suspended in HBSS were aliquoted at $4\times10^6$ cells/ml in 15 ml tubes and preincubated with either 50 or 100 µM of MANS, RNS, or one of the peptides of invention for 10 min at 37° C. The cells then were stimulated with 100 nM phorbol 12-myristate 13-acetate (PMA) for up to 3 hrs. A control reference (PMA control reference) was established using purified human neutrophils suspended in HBSS aliquoted at $4\times10^6$ cells/m in 15 mL tubes and stimulated with 100 nM phorbol 12-myristate 13-acetate (PMA) in the absence of a test peptide for the same time periods. The reaction was terminated by placing the tubes on ice and centrifugation at 400 g for 5 min at 4° C.

MPO activity in the cell supernatant was assayed using tetramethylbenzidine (TMB) based on a previously established technique (Abdel-Latif D, Steward M, Macdonald D L, Francis Ga., Dinauer M C, Lacy P. Rac2 is critical for neutrophil primary granule exocytosis. Blood 2004; 104:832-839). Briefly, 100 µL of TMB substrate solution was added to 50 µL of cell supernatants or standard human MPO (EMD Biosciences, Inc., San Diego, Calif.) in a 96-well microplate followed by incubation at room temperature for 15 min. The reaction was terminated by addition of 50 µL of 1M $H_2SO_4$ and absorbance was read at 450 nm in a spectrophotometric microplate reader (VERSA max, Molecular Devices, Sunnyvale, Calif.).

Leukocyte Culture Studies.

Three types of human leukocyte cell lines, specifically the promyelocytic cell line HL-60 clone 15, the monocytic cell line U937, and the lymphocyte natural killer cell line NK-92 were purchased from American Type Culture Collection (ATCC; Rockville, Md.). HL-60 clone 15 cells (ATCC CRL-1964) were maintained in medium consisting of RPMI 1640 with L-glutamine supplemented with 10% heat-inactivated fetal bovine serum (Gibco; Invitrogen Co., Carlsbad, Calif.), 50 IU/ml penicillin, 50 µg/mL streptomycin, and 25 mM HEPES buffer, pH 7.8, at 37° C. in an atmosphere containing 5% CO2. Final differentiation to an eosinophil-like phenotype was initiated by culturing cells at $5\times10^5$ cells/ml in the above medium containing 0.5 mM butylic acid (Sigma-Aldrich Co.) for 5 days as previously described (Tiffany H L, Li F, Rosenberg H F. Hyperglycosylation of eosinophil ribonucleases in a promyelocytic leukemia cell line and in differentiated peripheral blood progenitor cells. J Leukoc Biol 1995; 58:49-54; Tiffany H L, Alkhatib G, Combadiere C, Berger E A, Murphy P M. CC chemokine receptors 1 and 3 are differentially regulated by IL-5 during maturation of eosinophilic HL-60 cells. J Immunol 1998; 160:1385-1392). U937 cells (ATCC CRL-1593.2) were grown at 37° C. in an atmosphere of 5% $CO_2$ in complete medium consisting of RPMI 1640 with L-glutamine supplemented with 10% FBS, 50 IU/ml penicillin, and 50 µg/mL streptomycin. NK-92 cells (ATCC CRL-2407) were maintained in alpha-MEM medium (Sigma-Aldrich Co.) supplemented with 20% FBS, 100 U/ml of interleukin-2 (IL-2) (Chemicon International, Inc., Temecula, Calif.), $5\times10^{-5}$ M of 2-mercaptoethanol, 50 IU/mL penicillin, and 50 µg/ml streptomycin at 37° C. in an atmosphere containing 5% $CO_2$. Cell morphology was judged by assessment of Wright-Giemsa-stained cells. Viability of cells harvested for experiments was assessed by trypan blue exclusion and populations of cells with viability >95% were used.

Incubation of Cells for Degranulation Assays.

HL-60 clone 15, U937, and NK-92 cells were washed and resuspended at $2.5\times10^6$ cells/ml in phenol red-free RPMI-1640 (Cellgro; Mediatech, Inc.) for all degranulation assays. Aliquots of cells in 15 ml tubes were preincubated with indicated concentrations of MANS, RNS, or a test peptide for 10 min at 37° C. The cells then were stimulated with PMA for up to 2 hr. A control reference (PMA control reference) was established for each cell type using HL-60 clone 15, U937, and NK-92 cells, respectively, which were washed and resuspended at $2.5\times10^6$ cells/ml in phenol red-free RPMI-1640 and stimulated with PMA but in the absence of MANS, RNS, or a test peptide for the same time periods. The reaction was terminated by placing tubes on ice and centrifuging cells at 400 g for 5 min at 4° C.

For measurements of released MPO from neutrophils and released lysozyme from U937 cells, we were able to quantify secretion by using as standards human MPO and egg white ovalbumin, respectively. For released EPO from HL-60 clone 15 cells and for released granzyme from NK-92 cells, no standards were available to use for quantification. Hence, both released and intracellular (from lysed cells) levels of EPO and granzyme were measured, and the released EPO and granzyme were expressed as a percentage of total (intracellular and released) for each. To measure intracellular EPO in HL-60 clone 15 cells and intracellular granzyme in NK-92 cells, appropriate aliquots of 0.1% triton X-100-lysed cells were taken for quantification of intracellular granule proteins as described below. All treatments were expressed as percentage of control to minimize variability between cultures.

Measurement of HL-60 EPO Release.

EPO activity released by HL-60 clone 15 cells was assayed using TMB according to a previously established technique (Lacy P, Mahmudi-Azer S, Bablitz B, Hagen S C, Velazquez J R, Man S F, Moqbel R. Rapid mobilization of intracellularly stored RANTES in response to interferon-gamma in human eosinophils. Blood 1999; 94:23-32). Thus, 100 µL of TMB substrate solution was added to 50 µL (µL=microliters) of sample in a 96-well microplate and incubated at room temperature for 15 min (min=minutes). The reaction was terminated by addition of 50 µL of 1.0M $H_2SO_4$ and absorbance was read at 450 nm (nm=nanometers) in a spectrophotometric microplate reader. The amount of secreted EPO was expressed as percentage of total content, using the amount obtained in the same number of triton X-100-lysed cells.

Measurement of Monocyte Lysozyme Secretion.

Lysozyme secreted by U937 cells was measured using a spectrophotometric assay as described previously (Balboa M A, Saez Y, Balsinde J. Calcium-independent phospholipase A2 is required for lysozyme secretion in U937 promonocytes. J Immunol 2003; 170:5276-5280) with slight modification. Thus, 100 µL of sample was mixed with 100 µL of a *Micrococcus lysodeikticus* (Sigma-Aldrich Co.) suspension (0.3 mg/ml in 0.1 M sodium phosphate buffer, pH 7.0) in a 96-well microplate. The decrease in absorbance at 450 nm was measured at room temperature. A calibration curve was constructed using chicken egg white lysozyme (EMD Biosciences, Inc.) as a standard.

Measurement of NK Cell Granzyme Secretion.

Granzyme secreted from NK-92 cells was assayed by measuring hydrolysis of Nα-benzyloxycarbonyl-L-lysine thiobenzyl ester (BLT) essentially as described previously (Takayama H, Trenn G, Sitkovsky M V. A novel cytotoxic T lymphocyte activation assay. J Immunol Methods 1987; 104:

183-190). Briefly, 50 μL of supernatant was transferred to a 96-well plate, and 150 μL of BLT solution (0.2 mM BLT; EMD Biosciences, Inc., and 0.22 mM DTNB; Sigma-Aldrich Co.) (mM=millimolar) in phosphate-buffered saline (PBS, pH, 7.2) was added to the supernatant. Absorbance at 410 nm was read after incubation for 30 min at room temperature. Results were expressed as percentage of total cellular enzyme content, using the amount obtained in the same number of triton X-100-lysed cells.

Statistical Analysis.

Statistical significance of the differences between various treatment groups was assessed with one-way ANOVA. P values of <0.05 were taken as significant.

Inhibition of MPO Release From Human Neutrophils

It was found that 100 nM PMA (as a stimulator of inflammatory mediator release) increased human neutrophil MPO release by approximately threefold versus control level at 30 min in the PMA control reference, the release of MPO increasing to approximately 5-6 fold after 3 hrs. At 30 minutes, relative to the control MPO activity as 100% absent PMA and absent PMA plus MANS, RNS, or test peptide, MPO activity of the PMA control reference was about 275%, PMA plus 50 μM MANS was about 275%, and 100 μM MANS was about 305%. Thus, the MANS peptide had no detected effect at 30 min. However, by 1 hr the higher concentration of MANS (100 μM) had a significant inhibitory effect (measured at about 260% of control) or about 25% reduction in MPO release versus the PMA control reference level (which was measured at about 340% of control). The 50 μM MANS sample measured about 290% of control or about 15% reduction relative to the PMA control reference. By 2 hrs and persisting at 3 hrs, the MANS peptide significantly attenuated MPO activity in a concentration-dependent manner. At 2 hours, the PMA control reference MPO activity was about 540% of control, the 50 μM MANS (measuring about 375% of control) caused an approximately 30% reduction of MPO release versus the PMA control reference; and 100 μM MANS (measuring about 295% of control) caused an approximately 45% reduction of MPO release versus the PMA control reference. At 3 hours, the PMA control reference MPO activity was about 560% of control, 50 μM MANS (measuring about 375% of control) caused an approximately 33% reduction of MPO release versus the PMA control reference; 100 μM MANS (measuring about 320% of control) caused an approximately 40% reduction of MPO release versus the PMA control reference. The RNS peptide did not affect PMA-induced MPO release at any of the time points or concentrations tested. The data presented in the table below represents 100 μM concentration of test peptides and a two hour incubation with 100 nM PMA.

inhibition of EPO Release from HL-60 Cells

EPO activity in the supernatant of HL-60 clone 15 cells was significantly enhanced at 1 and 2 hrs after PMA stimulation. At 1 hour, relative to EPO activity of the control as 100%, the PMA control reference measured at about 110%; the sample containing 10 μM MANS measured at about 95% to give about 15% reduction in EPO activity relative to the PMA control reference; the sample containing 50 μM MANS measured at about 78% to give about 30% reduction in EPO activity relative to the PMA control reference; and the sample containing 100 μM MANS measured at about 65% to give about 40% reduction in EPO activity relative to the PMA control reference. At 2 hour, relative to EPO activity of the control as 100%, the PMA control reference measured at about 145%; the sample containing 10 μM MANS measured at about 130% to give about 10% reduction in EPO activity relative to the PMA control reference; the sample containing 50 μM MANS measured at about 70% to give about 50% reduction in EPO activity relative to the PMA control reference; and the sample containing 100 μM MANS measured at about 72% to give about 50% reduction in EPO activity relative to the PMA control reference. Thus, at both 1 and 2 hrs, MANS at 50 or 100 μM significantly attenuated EPO release. The RNS peptide did not affect PMA-enhanced EPO release at any of the time points or concentrations tested. The data presented in the table below represents 50 μM concentration of test peptides and a two hour incubation with 100 nM PMA.

Inhibition of Lysozyme Release from U937 Cells

Lysozyme secretion by U937 cells was increased by PMA stimulation by 1 hr after incubation, and increased even more at 2 hrs. At 1 hour, relative to lysozyme secretion by U937 cells of the control as 100%, the PMA control reference measured at about 210%; the sample containing 10 μM MANS measured at about 170% to give about 20% reduction in lysozyme secretion by U937 cells relative to the PMA control reference; the sample containing 50 μM MANS measured at about 170% to give about 20% reduction in lysozyme secretion by U937 cells relative to the PMA control reference; and the sample containing 100 μM MANS measured at about 115% to give about 45% reduction in lysozyme secretion by U937 cells relative to the PMA control reference. At 2 hour, relative to lysozyme secretion by U937 cells of the control as 100%, the PMA control reference measured at about 240%; the sample containing 10 μM MANS measured at about 195% to give about 20% reduction in lysozyme secretion by U937 cells relative to the PMA control reference; the sample containing 50 μM MANS measured at about 185% to give about 25% reduction in lysozyme secretion by U937 cells relative to the PMA control reference; and the sample containing 100 μM MANS measured at about 140% to give about 40% reduction in lysozyme secretion by U937 cells relative to the PMA control reference. Thus, lysozyme secretion was significantly attenuated at both 1 and 2 hours post-stimulation by 100 μM of MANS but not as much by 50 or 10 μM of MANS. The RNS peptide did not affect PMA-enhanced lysozyme secretion at any of the time points or concentrations tested. The data presented in the table below represents 50 μM concentration of test peptides and a two hour incubation with 100 nM PMA.

Inhibition of Granzyme Release from NK-92 Cells

The lymphocyte natural killer cell line NK-92 was used to assess release of granzyme (Gong J H, Maki G, Klingemann H G. Characterization of a human cell line (NK-92) with phenotypical and functional characteristics of activated natural killer cells. Leukemia 8:652-658, 1994; Maki G, Klingemann H G, Martinson J A, Tam Y K. Factors regulating the cytotoxic activity of the human natural killer cell line, NK-92. J. Hematother. Stem Cell Res., 10:369-383, 2001; Takayama H, Trenn G, Sitkovsky M V. A novel cytotoxic T lymphocyte activation assay. J. Immunol. Methods 104:183-190, 1987).

Measurement of NK cell granzyme secretion: Granzyme secreted from NK-92 cells was assayed by measuring hydrolysis of Nα-benzyloxycarbonyl-L-lysine thiobenzyl ester (BLT, EMD Bioscience, Inc.) essentially as described previously (Takayama H, Trenn G, Sitkovsky M V. A novel cytotoxic T lymphocyte activation assay. J. Immunol. Methods 104:183-190, 1987). An aliquot of 50 μL of supernatant was transferred to a 96-well plate, and 150 μL of 0.2 mM solution of BLT and 0.22 mM DTNB (Sigma-Aldrich Co.) in phosphate-buffered saline (PBS, pH 7.2) was added to the supernatant. Absorbance at 410 nm was measured after incubation for 30 min at room temperature. Results were expressed as percentage of total cellular enzyme content, using the amount obtained in the same number of triton X-100-lysed cells.

Because standard granzyme from NK-92 cells was not available to use for quantification, we measured both released and intracellular (from lysed cells) levels of granzyme, and expressed the released granzyme as a percentage of total (intracellular and released) for each. To measure intracellular granzyme from NK-92 cells, appropriate aliquots of 0.1% triton X-100-lysed cells were taken for quantification of the enzyme as described above. All data are expressed as percentage of control to minimize variability between cultures. The data presented in the table below represents 50 μM concentration of test peptides and a two hour incubation with 100 nM PMA.

Cytotoxicity

Because standard None of the treatments generated a toxic response in the cells, as assessed by LDH retention/release (data not shown) (see also Park J-A, He F, Martin L D, Li Y, Adler K B. Human neutrophil elastase induces hypersecretion of mucin from human bronchial epithelial cells in vitro via a PKCδ-mediated mechanism. Am J Pathol 2005; 167: 651-661).

In preliminary experiments, the following peptides which are presented in the table below demonstrate respective percent inhibition of release of MPO from human neutrophils, of EPO from HL-60 clone 15 cells, of lysozyme from U937 cells, and of granzyme from NK-92 cells, wherein MA- signifies the presence of a myristoyl substituent group at the alpha-N-terminal position of the peptide; Ac- signifies the presence of an acetyl substituent group at the alpha-N-terminal position of the peptide; H signifies no group attached to the peptide; and NH2 signifies the presence of an amide at the C-terminal position. Inhibition data are averaged from multiple experiments. Qualitative solubility of the peptides in 0.5 N saline at pH 6.5 is given in mg/mL in Table 3 below. Changing the N-terminal chemical moiety from a myristoyl group can lead to changes in solubility of the peptides disclosed herein in aqueous media. For example, changing the myristoyl group to an acetyl group results in the increased aqueous solubility shown in Table 3.

TABLE 3

Results of Enzyme inhibition assays solubilities for representative peptides and substituted peptides

| SEQ ID NO.: | N-[1] | Amino Acid Sequence | C-[2] | % Inhibition EPO | Lysozyme | MPO | Granzyme | mg/mL Solubility[3] |
|---|---|---|---|---|---|---|---|---|
| 219 | Ac | AKGE | | 87.6 | 7.2 | | | >200 |
| 45 | Ac | AKGEAAAERPGEAAVA | | 72.3 | 34.3 | | | |
| 37 | Ac | GAQFSKTAAKGEAAAE | | 56.6 | 8.4 | | | |
| 239 | Ac | GAQFSKTAAAGE | | 55.8 | 37.2 | | | >50 |
| 248 | Ac | GAQFSKTAAA | | 55.2 | 28.3 | | | >100 |
| 91 | Ac | AAAERPGEAAVA | | 51.2 | 29.5 | | | |
| 11 | Ac | GAQFSKTAAKGEAAAERPGE | | 48.8 | 0.0 | | | |
| 79 | Ac | GAQFSKTAAKGE | | 46.7 | 43.3 | | | >100 |
| 153 | Ac | RPGEAAVA | | 45.8 | 0.0 | | | |
| 219 | Ac | AKGE | NH2 | 45.6 | 26.8 | | | >200 |
| 93 | Ac | AQFSKTAAKGE | NH2 | 42.8 | 51.8 | | | >90 |
| 141 | Ac | SKTAAKGE | NH2 | 42.2 | 0 | | | >200 |
| 241 | Ac | GAQFSKTAAKGA | | 40.9 | 24.1 | | | >50 |
| 143 | Ac | TAAKGEAA | | 40.4 | 0.5 | | | >230 |
| 251 | Ac | AAGE | | 39.1 | 36.9 | | | >200 |
| 106 | Ac | GAQFSKTAAK | | 35.7 | 41.2 | 25.3 | | >100 |
| 249 | Ac | GAQFSATAAA | | 35.7 | 3.2 | | | <10 |
| 1 | Ac | GAQFSKTAAKGEAAAERPGEAAVA | | 33.7 | 39.8 | | | >250 |
| 121 | Ac | GAQFSKTAA | | 33.3 | 28.9 | | | >20 |
| 106 | Ac | GAQFSKTAAK (all d) | | 26.9 | 8.9 | 40.0 | | >100 |
| 124 | Ac | FSKTAAKGE | NH2 | 25.3 | 56.7 | | | >100 |
| 79 | Ac | GAQFSKTAAKGE | NH2 | 24.7 | 38.6 | 26.5 | | >60 |

TABLE 3-continued

Results of Enzyme inhibition assays solubilities for representative peptides and substituted peptides

| SEQ ID NO.: | N-[1] | Amino Acid Sequence | C-[2] | % Inhibition | | | | mg/mL Solubility[3] |
|---|---|---|---|---|---|---|---|---|
| | | | | EPO | Lysozyme | MPO | Granzyme | |
| 108 | Ac | QFSKTAAKGE | NH2 | 15.7 | 60.7 | | | >150 |
| 179 | Ac | AAKGEA | | 10.6 | 9.2 | | | >150 |
| 159 | Ac | KTAAKGE | NH2 | 0 | 24.3 | | | >200 |
| 137 | Ac | GAQFSKTA | | 0 | 0 | | | >200 |
| 79 | H | GAQFSKTAAKGE | | | | 27.9 | | >60 |
| 1 | MA | GAQFSKTAAKGEAAAERPGEAAVA | | 46.1 | 40.8 | 31.2 | 76.0 | <5.0 |
| 106 | MA | GAQFSKTAAK | | 37.4 | 56.6 | | | >10 |
| 11 | MA | GAQFSKTAAKGEAAAERPGE | | 33.6 | | | | |
| 179 | MA | AAKGEA | | 31.4 | 28.6 | | | <1.0 |
| 37 | MA | GAQFSKTAAKGEAAAE | | 30.3 | 99 | | | >2.0 |
| 79 | MA | GAQFSKTAAKGE | | 25.2 | 85.2 | 43.2 | | >2.0 |
| 91 | MA | AAAERPGEAAVA | | 21.6 | 98 | | | <20 |
| 45 | MA | AKGEAAAERPGEAAVA | | 18.1 | 98 | | | >80 |
| 153 | MA | RPGEAAVA | | 0 | 99 | | | |
| 15 | MA | SKTAAKGEAAAERPGEAAVA | | 0 | 99 | | | >80 |
| 143 | MA | TAAKGEAA | | 0 | 80.2 | | | <1.0 |
| 219 | MA | AKGE | | 0 | 28.6 | | | <1.0 |
| 232 | MA | GTAPAAEGAGAEVKRASAEAKQAF | | 0 | 0 | | 29.5 | >15 |
| 234 | MA | GAQFSKTKAKGE | | | | 65.2 | | >3.0 |

[1]N- = N-terminal group
[2]C- = C-terminal group
[3]0.5N Saline, pH 6.5

Example 2

In Vivo Inhibition of Lipopolysaccharide (LPS)-Induced Lung Inflammation by MANS and Related Peptides This example was performed essentially according to methods described by Cox, G, Crossley, J., and Xing, Z.; Macrophage engulfment of apoptotic neutrophils contributes to the resolution of acute pulmonary inflammation in vivo; Am. J. Respir. Cell Mol. Biol. 12:232-237, 1995; Hirano S., Quantitative time-course profiles of bronchioalveolar lavage cells following intratracheal instillation of lipopolysaccharide in mice, Ind. Health 35:353-358, 1997; and Ulrich T R, Watson L R, Yin S M, Guo K Z, Wang P, Thang H, and del Castillo, J. Am. J. Pathol. 138:1485-1496, 1991.

Thus, six to seven week old CD1 female mice weighing 15-20 grams were obtained from Charles River laboratories and housed in groups of 5 mice per cage. The animals received standard rodent diet and filtered water ad libitum. The animals were housed under NIH prescribed guidelines at standard temperature (64° to 79° F.) and relative humidity of 30 to 70%.

Five treatment groups of mice, with 5 animals in each group, were treated either with PBS followed by PBS, with PBS followed by LPS, with (myristoylated) MANS peptide followed by LPS, with acetylated peptide of SEQ ID NO: 1, followed by LPS, or with acetylated peptide of SEQ ID NO: 106, followed by LPS.

Intranasal peptide instillation pre-treatment: A peptide of the invention to be evaluated in vivo for its ability to inhibit or reduce LPS-induced lung inflammation was dissolved in PBS at a concentration of 1 mM. Animals, anesthetized with 0.8% isoflourane by inhalation, were pretreated with 2×10 μL intranasal bolus of the peptide solution into one nostril 30 minutes prior to subsequent instillation with LPS.

Intranasal LPS instillation: Lipopolysaccharide (LPS) Endotoxin (*Escherichia coli* Serotype 011:B4 derived endotoxin; Sigma, St Louis, Mo.; see Sigma product information sheet L4130 titled Lipopolysaccharides from *Escherichia coli* 011:B4) was dissolved into phosphate buffered saline (PBS) at 2,500 μg/mL. To expose animals to endotoxin, a 10 μL intranasal bolus of 2,500 μg/ml endotoxin solution was administered to animals which had been anesthetized with 0.8% isoflourane by inhalation. The 10 μL bolus was applied into one nostril. Animals were monitored for labored breathing, lethargy, and decreased water/food intake following the endotoxin instillations.

Bronchoalveolar Lavage (BAL): Six hours after the last instillation, the animals were anesthetized (90 mg/kg Nembutal) and sacrificed by exsanguination. The lung was serially lavaged 2 times with 1.0 mL aliquots of PBS. The collected BAL fluid was centrifuged to remove the cells for subsequent counting and differential analysis. Recovered lavage fluid was used for analysis of total protein, myeloperoxidase (MPO), LDH, and hemoglobin.

Analysis: Aliquots of the BAL fluid were used immediately to assay for the levels of LDH, total protein, or hemoglobin using the COBAS Fara analyzer (COBAS FARA II automated analyzer; Roche Diagnostic Systems Inc., Montclair, N.J.). An aliquot of BAL fluid was frozen at ~80° C. for subsequent quantitation of myeloperoxidase (MPO) with a mouse-specific ELISA assay (Cell Sciences, Inc., Canton, Mass.). BAL data were analyzed by standard techniques to examine differences between the control and treatment groups. Results demonstrating inhibition or reduction of inflammation by Test peptide are provided in the following tables.

TABLE 4

Average values of markers of inflammation in the presense of MANS peptide, MA-GAQFSKTAAKGEAAAERPGEAAVA, SEQ ID NO.: 1

| Treatment Regime | Total cells counted | Total neutrophils counted | % Neutrophils of total cells | MPO (ng/mL) | Protein (ug/ml) | LDH (units/L) | Hb (g/dl) |
|---|---|---|---|---|---|---|---|
| PBS/PBS n = 5 | 157,020 | 29317 | 18.7 | 3.28 | 125.60 | 68.20 | 0.00 |
| PBS/LPS n = 5 | 264,200 | 110,061 | 41.7 | 28.98 | 272.40 | 60.40 | 0.19 |
| MANS/LPS n = 7 | 208,457 | 64,481 | 30.9 | 9.49 | 175.00 | 68.57 | 0.05 |

TABLE 5

Average values of markers of inflammation in the presence of an N-terminal acetylated analog of MANS peptide, Ac-GAQFSKTAAKGEAAAERPGEAAVA, SEQ ID NO: 1

| Treatment Regime | Total cells counted | Total neutrophils counted | % Neutrophils of total cells | MPO (ng/mL) | Protein (ug/ml) | LDH (units/L) | Hb (g/dl) |
|---|---|---|---|---|---|---|---|
| PBS/PBS n = 5 | 89,440 | 19,770 | 22.1 | 5.45 | 230.6 | 84.0 | 0.00 |
| PBS/LPS n = 5 | 251,360 | 164,578 | 65.5 | 37.90 | 153.4 | 89.9 | 0.01 |
| Ac-SEQ ID NO.: 1/LPS n = 5 | 254,400 | 105,499 | 41.47 | 30.79 | 182.75 | 74.5 | 0.01 |

TABLE 6

Average values of markers of inflammation in the presence of acetylated peptide Ac-GAQFSKTAAK, SEQ ID NO.: 106

| Treatment Regime | Total cells counted | Total neutrophils counted | % Neutrophils of total cells | MPO (ng/mL) | Protein (ug/ml) | LDH (units/L) | Hb (g/dl) |
|---|---|---|---|---|---|---|---|
| PBS/PBS n = 5 | 312,620 | 66,521 | 21.3 | 4.88 | 113.8 | 61.80 | 0.00 |
| PBS/LPS n = 5 | 327,680 | 80,077 | 24.4 | 7.19 | 116.4 | 78.20 | 0.00 |
| Ac-SEQ ID NO.: 106/LPS n = 5 | 305,688 | 9,170 | 3.0 | 1.50 | 131.0 | 106.86 | 0.00 |

TABLE 7

Inhibition of markers of inflammation by MANS peptide (Myr-SEQ ID NO:1), test peptides (Ac-GAQFSKTAAKGEAAAERPGEAAVA), SEQ ID NO: 1, and Ac-GAQFSKTAAK, SEQ ID NO: 106, relative to PBS/LPS treatment:

| Treatment Regime | Inhibition of neutrophil migration | Inhibition of MPO |
|---|---|---|
| MANS/LPS | 41.4% | 67.2% |
| SEQ ID NO:1/LPS | 35.9% | 18.75% |
| Ac-SEQ ID NO. 106/LPS | 88.5% | 79.1% |

PBS/PBS indicates only PBS control was administered, and no LPS endotoxin was added to stimulate chemotactic neutrophil migration; PBS/LPS indicates LPS (endotoxin) was added to stimulate chemotactic neutrophil migration; MANS/LPS indicates pretreatment with MANS peptide in PBS followed by LPS stimulation to induce neutrophil migration. The percent of neutrophils in the total cell count in the LPS treatment groups was reduced from 41.7% to 30.9% by treatment with MANS peptide; from 65.5% to 41.47% by treatment with the peptide Ac-GAQFSKTAAKGEAAAERPGEAAVA, SEQ ID NO. 1; from 24.4% to 3.0% by treatment with the peptide Ac-GAQFSKTAAK, SEQ ID NO. 106. The measured MPO levels in the LPS treatment groups was reduced from 28.98 ng/mL to 9.49 ng/mL by treatment with MANS peptide; from 37.9 ng/mL to 30.79 ng/mL by treatment with the peptide with acetylated SEQ ID NO:1 and from 7.19 ng/mL to 1.50 ng/mL by treatment with the peptide with acetylated SEQ ID NO:106.

Example 3

Mouse Model of Ozone-Induced COPD

Oxidative stress by chemical irritants such as ozone is a widely recognized feature of chronic obstructive respiratory disease (COPD). See: Repine J E, Bast A, Lankhorst I, and the Oxidative Stress Study Group, Am. J. Respir. Crit. Care Med. 156:341-357, 1997; and also Harkema J R and Hotchkiss J A, Toxicology Letters, 68:251-263, 1993.

Ten-week-old Balb/C female mice were obtained from Charles River laboratories and housed under NIH guidelines in groups of 5 per cage. The animals received standard rodent diet and filtered water ad libitum. Three treatment groups of mice, 5 animals in each group, were each anesthetized by intraperitoneal injection of Ketamine (100 mg/kg) and Xylazine (20 mg/kg) and then pretreated by intratracheal administration with 25 µL of either PBS alone, or a solution of 1.0 mM MANS peptide in PBS, or a solution of a 1.0 mM of an acetylated MANS-fragment-peptide Ac-GAQFSKTAAK designated as acetylated SEQ ID NO: 106 in PBS. After 30 minutes, the animals were then placed in the appropriate custom-made chamber for ozone or forced air exposures. The animals were exposed to ozone for 2 hours (at ozone concentrations of 1-10 ppm by a slightly modified method described by Haddad et al, 1995. (Haddad E-B, Salmon M, Sun J, Liu S, Das A, Adcock I, Barnes P J, and Chung K F, FEBS Letters, 363:285-288, 1995). The ozone was generated using an ozone generator apparatus model OL80F/B from OzoneLab, Burton, British Columbia, Canada. Ozone concentration was continuously monitored using a Teledyne Photometric O3 Analyzer (model 400E, Teledyne Instruments, City of Industry, Calif.). Two additional groups of mice, each without any pretreatment, were either exposed to ozone under the same conditions or exposed to forced air under conditions similar to the ozone treatment group but absent ozone. After exposure, the animals were sacrificed by exsanguination and the lungs were serially lavaged 2 times with 1.0 mL aliquots of PBS. The collected bronchioalveolar lavage (BAL) fluid was centrifuged to remove the cells for subsequent counting and differential analysis. Recovered lavage fluid was used for protein and additional analysis of IL-6, IFNγ, and KC (murine IL-8 analog) by ELISA assay (assay kits obtained from R&D Systems, Minneapolis, Minn.).

The percent inhibition of neutrophil migration into the BAL fluid as a function of treatment groups and relative to a control group treated with PBS alone are provided in the table.

TABLE 8

Inhibition of ozone-induced neutrophil migration by MANS peptide and by peptide acetylated SEQ ID NO: 106, Ac-GAQFSKTAAK.

| Treatment Group | % Inhibition of neutrophil migration into BAL fluid |
|---|---|
| MANS + Ozone | 93.0 |
| Ac-SEQ ID NO: 106 + Ozone | 81.2 |
| PBS + Ozone | Not applicable |
| Forced air alone | Not applicable |

Concentrations of IL-6 in pg/mL in BAL fluid, as a function of intratracheal injection pretreatment and subsequent treatment with ozone, were obtained as follows. IL-6 levels were found to be: approximately 364.5 pg/mL in a group of mice pretreated with MANS peptide and then exposed to ozone; approximately 130.4 pg/mL in a group of mice pretreated with acetylated MANS-fragment-peptide, Ac-GAQF-SKTAAK (SEQ ID NO: 106), and then exposed to ozone; approximately 1041.3 pg/mL in a group of mice pretreated with PBS and exposed to ozone; approximately 43.2 pg/mL in a group of mice exposed directly to forced air without any pretreatment.

Concentrations of KC in pg/mL in BAL fluid, as a function of intratracheal injection pretreatment and subsequent treatment with ozone, were obtained as follows. KC levels were found to be: approximately 183.6 pg/mL in a group of mice pretreated with MANS peptide and then exposed to ozone; approximately 159.7 pg/mL in a group of mice pretreated with acetylated MANS-fragment-peptide, Ac-GAQFSK-TAAK (SEQ ID NO:106), and then exposed to ozone; approximately 466.6 pg/mL in a group of mice pretreated with PBS and exposed to ozone; approximately 36.3 pg/ml in a group of mice exposed to forced air without pretreatment.

Concentrations of IFNγ in pg/mL in BAL fluid as a function of intratracheal injection pretreatment and subsequent treatment with ozone were obtained as follows. IFNγ levels were found to be: approximately 7.4 pg/mL in a group of mice pretreated with MANS peptide and then exposed to ozone; approximately 3.6 pg/ml in a group of mice pretreated with acetylated MANS-fragment-peptide, Ac-GAQFSKTAAK (SEQ ID NO:106), and then exposed to ozone; approximately 8.6 pg/mL in a group of mice pretreated with PBS and exposed to ozone; and approximately 5.0 pg/mL in a group of mice exposed to forced air.

Administration of ozone to mice significantly increased infiltrated neutrophil cell numbers, as well as IL-6 and KC levels in the BAL. In comparison to the control group in which the mice were pretreated with PBS, the group pretreated with MANS peptide and the group pretreated with acetylated peptide, Ac-GAQFSKTAAK, acetylated SEQ ID NO:106. each exhibited reduced neutrophil cell infiltration in the BAL fluid after ozone exposure (e.g., 93%±10% and 81%±10%, respectively vs. PBS control). In parallel, MANS peptide and acetylated peptide acetylated SEQ ID NO:106 also markedly diminished KC concentrations (e.g., 65.8%±10% and 71.3%±10%, respectively, vs. PBS control) and IL-6 levels (e.g., 67.8%±15%, MANS and 91.3%±15% acetylated SEQ ID NO: 106 vs. PBS control) after ozone exposure but had little effect on interferon-γ levels. Collectively, these data evidence that MANS peptide and acetylated SEQ ID NO:106 peptides markedly diminish or inhibit ozone-induced neutrophil migration into the airways as well as decrease selective chemokine and cytokine. The IL-6 levels in the BAL fluids from animals pretreated with MANS peptide or acetylated peptide SEQ ID NO:106 showed approximately 68% and 91% inhibition, respectively, compared to those pretreated with PBS. Also the KC levels in the BAL fluids from animals pretreated with MANS peptide or acetylated peptide SEQ ID NO:106 showed approximately 65% and 71% inhibition compared to those pretreated with PBS.

Example 4

Chronic Bronchitis Model

The procedure is described by Voynow J A, Fischer B M, Malarkey D E, Burch L H, Wong T, Longphre M, Ho S B, Foster W M, Neutrophil Elastase induces mucus cell metaplasia in mouse lung, Am. J. Physiol. Lung Cell Mol. Physiol. 287:L1293-L1302, 2004 and is followed to develop a model of chronic bronchitis in the mouse. Specifically, goblet cell hyperplasia, a signature pathological feature of chronic bronchitis, is induced by chronic exposure of mice to human Neutrophil Elastase (NE) instilled into the airways.

Human NE are aspirated intratracheally by male Balb/c mice. A total of 30 mice (about 25-30 g in weight) are obtained commercially from a supplier such as Jackson Laboratories, Bar Harbor, Me. The mice are maintained on a 12 hr diurnal cycle, with food and water provided ad libitum. The animals receive NE by oropharyngeal aspiration on days 1, 4, and 7. Immediately after inhalational anesthesia with isofluorane (IsoFlo from Abbott Laboratories and Open-Circuit Gas Anesthesia System from Stoelting), animals are suspended by their upper incisors on a 60° incline board, and a liquid volume of human NE [50 ug (43.75 units)/40 µL PBS (Elastin Products, Owensville, Mo.) is delivered with the animal's tongue extended to the distal part of the oropharynx. With the tongue extended, the animal is unable to swallow, and the liquid volume is aspirated in the respiratory tract.

At 7 days after the last NE exposure, when the goblet cell hyperplasia modeling the airways in chronic bronchitis is at its maximum (see Voynow et al, 2004), mice (5 animals per group) are instilled intra-tracheally with 50 µL of either PBS (as control), or 100 uM of a solution of MANS peptide, a solution of RNS peptide, or a solution of a peptide such as acetylated peptide SEQ ID NO: 106 dissolved in PBS. Fifteen minutes later, mucus secretion is triggered by administration of methacholine, using a Buxco system Nebulizer to provide a fine aerosol delivering methacholine at approximately 60 mM for 3 min. Fifteen minutes after methacholine administration, mice are sacrificed by inhalational exposure to 100% $CO_2$ gas.

Histochemistry. After exposures described above, lungs from animals are flushed to remove blood, then are inflated with OCT (Optimum Cutting Temperature medium (Sakura Finetck, Torrance, Calif.), half diluted in saline. The lungs are immersed in 10% formaldehyde in PBS overnight at 4° C., and processed to paraffin wax. Five µm sections are treated with Periodic acid Schiff/haematoxylin to stain mucins in the airways, for example as described by Singer M, Vargaftig B B, Martin L D, Park J J, Gruber A D, Li Y, Adler K B, A MARCKS-related peptide blocks mucus hypersecretion in a murine model of asthma, Nature Medicine 10:193-196, 2004.

Histological mucus index. A histological mucus index (Whittaker L, Niu N, Temann U-A. Stoddard A, Flavell R A, Ray A, Homer R J, and Cohn L, Interleukin-13 mediates a fundamental pathway for airway epithelial mucus induced by CD4 T cells and interleukin-9, Am. J. Respir. Cell Mol. Biol. 27:593-602, 2002) is performed on AB/PAS-stained sections that include both central and peripheral airways. The slides are examined with a 10× objective, and images captured with a digital camera. A minimum of four representative cross- or sagittally sectioned airways is imaged per animal. Only airways where the complete circumference of the airway can be visualized and included in the image are analyzed. Airways that open directly in an alveolar space are not included. The extent of PAS-positive staining in each airway imaged will be semi-quantitatively determined by an examiner who does not know the treatment conditions for each section, using the following five-tier grading system: grade 0, no PAS staining; grade 1, 25% or less of the airway epithelium has PAS staining; grade 2, 26-50% of the airway epithelium has PAS staining; grade 3, 51-75% of the airway epithelium has PAS staining; and grade 4, >75% of the airway epithelium has PAS staining. This grading system is used to calculate a mucus index score for each group, and results are presented as means±SE.

All results are presented as means±standard error (n=5 animals, 10-20 sections for each). Significance levels will be calculated using one way ANOVA followed by Scheffe's test, using SPSS 6.1 software (*=significance between data with a threshold of $p<0.05$).

Example 5

In Vivo Assays

The objective of the following set of experiments is to establish the effects of the peptides of this invention after in vivo delivery, either by local instillation at the site of inflammation or i.v. injection, on inflammation compared to the control peptides such as RNS. Two models are useful for this determination: (i) the murine air pouch inflammation model and (ii) the murine thioglycollate induced peritonitis model. Both are well-characterized models of inflammation in which neutrophils have an essential role. The air pouch model enables determination of the effects of the peptides on a short time course of inflammation (approximately 4 hrs) and the peritonitis model is useful with respect to a longer time course of inflammation (approximately 24 hrs).

Overall Experimental Design:

Four studies, two for each model, one testing i.v. delivery of the peptides and one testing local delivery of the peptides are useful for studying the effect of the peptides disclosed in this application. Each study consists of 2 experimental groups, a non-inflamed control (treated with vehicle) and an inflamed group (i.e., treated with an inflammatory stimulus). Each group is divided into 5 and optionally 6 treatment subgroups, n=6 for each subgroup. Treatments subgroups are, for example: vehicle, MANS, RNS, test peptide, optionally a peptide having a scrambled sequence of the test peptide which scrambled sequence are dubbed "peptide-SCR", and dexamethasone. Dexamethasone serves as a reference anti-inflammatory agent. The selection of appropriate doses for i.v. injection or local instillation are determined from preliminary dose response experiments. Tentative doses based on the inhibitory activity of MANS in human neutrophils are: 1 mg/kg for i.v. delivery administered once or a final concentration of 50 µM delivered locally (into the air pouch or i.p.). The dose for i.v. delivery are chosen assuming a volume of distribution of 2 L/kg.

Air Pouch Inflammation Model:

Assays for neutrophil infiltration and inflammation in the mouse air pouch are performed as described in Clish C B, O'Brien J A, Groneit K, Stahl G L, Petasis N A, Serhan C N. Local and systemic delivery of a stable aspirin-triggered lipoxin prevents neutrophil recruitment in vivo. Proc Natl Acad Sci USA. 1999 Jul. 6; 96(14):8247-52. Thus, white male BALB/c mice (6-8 wk) are anesthetized with isoflurane, and dorsal air pouches are raised by injecting 3 ml of sterile air subcutaneously on days 0 and 3. On day 6 and while the mice are anesthetized with isoflurane, vehicle, MANS, RNS, test peptide, or optionally peptide-SCR are delivered as a bolus injection either i.v. into the tail vein in 100 µL of sterile 0.9% saline or locally into the air pouch in 900 µL of PBS –/– (Dulbecco's Phosphate Buffered Saline without magnesium or calcium ions, BioWhittaker). Dexamethasone (Sigma) delivered i.v. as 0.1 mg/kg in 100 µl sterile 0.9% saline or locally as 10 µg in 900 µL of PBS –/–, serves as a reference anti-inflammatory agent. Inflammation in the air pouch is induced by local injection of recombinant murine tumor necrosis factor α (TNF-α, 20 ng) (Boehringer Mannheim) dissolved in 100 µL of sterile PBS. While the mice are anesthetized with isoflurane, the air pouches are lavaged twice with 3 mL of sterile PBS 4 hr after the initial TNF-α injection. Aspirates are centrifuged at 2,000 rpm for 15 min at 23° C. The supernatants are removed, and the cells suspended in 500 µL of PBS. Aliquots of the supernatant are assayed for inflammatory mediator concentrations (optionally except for TNFα), MPO activity, and lipid peroxidation.

Total leukocytes are enumerated in the cell suspension by light microscopy using a hemocytometer. Resuspended aspirate cells (50 µL) are added to 150 µL of 30% BSA and centrifuged onto microscope slides at 2,200 rpm for 4 min by using a cytofuge. Differential leukocyte counts are determined in cytospins stained with Wright Giemsa stain and used to calculate the absolute number of each leukocyte per air pouch exudate. For microscopic analysis, tissues are obtained with a 6-mm tissue biopsy punch (Acu-Punch, Acuderm) and fixed in 10% buffered formaldehyde. Samples are then embedded in paraffin, sliced and stained with hematoxylin-eosin. Neutrophils are enumerated in histological sections by counting number of cells/hpf. Distant dermis serve as a control for the inflamed air pouch dermis.

Data are presented as total number of neutrophils, monocytes, eosinophils, basophils, and lymphocytes per exudate or the number neutrophils per tissue high power field. Values are reported as the mean±SEM (n=6). The significance of any treatment on migration are determined by ANOVA. P<0.05 is to be considered significant.

Example 6

Inflamed Peritoneum Model

Male BALB/c mice (6-8 wk) are used and the thioglycollate-induced peritonitis models performed as described in Tedder T F, Steeber D A, Pizcueta P. L-selectin-deficient mice have impaired leukocyte recruitment into inflammatory sites. J Exp Med. 1995 Jun. 1; 181(6):2259-64. Vehicle, MANS, RNS, test peptide, and optionally peptide-SCR are delivered as a bolus injection either into the tail vein in 100 µL of sterile 0.9% saline or locally into the peritoneum 900 µl of PBS –/– immediately prior to i.p. injection of thioglycollate. Dexamethasone delivered i.v. as 0.1 mg/kg in 100 µL sterile 0.9% saline or locally as 10 µg in 900 µl of PBS –/–, serves as a reference anti-inflammatory agent. Inflammation is induced by injection of 1 mL of thioglycollate solution (3% wt/vol; Sigma Immunochemicals) intrapentoneally into the mice. Mice are humanely euthanized 24 hrs following induction of inflammation and 5 mL of warm (37° C.~medium (RPMI 1640, 2% FCS, and 2 mM EDTA) injected into the peritoneum followed by gentle massage of the abdomen. Aspirates of the abdominal lavage fluid are centrifuged at 2,000 rpm for 15 min at 23° C. The supernatants are removed, and the cells suspended in 500 mL of PBS. Aliquots of the supernatant are assayed for MPO activity, inflammatory mediator concentrations, and lipid peroxidation.

Total leukocytes are enumerated in the cell suspension by light microscopy using a hemocytometer. Resuspended aspirate cells (50 µL) are added to 150 µL of 30% BSA and centrifuged onto microscope slides at 2,200 rpm for 4 min by using a cytofuge. Differential leukocyte counts are determined in cytospins stained with Wright Giemsa stain and used to calculate the absolute number of each leukocyte per air pouch aspirate.

Data are presented as total number of neutrophils, monocytes, eosinophils, basophils, and lymphocytes per exudate. Values are reported as the mean±SEM (n=6). The significance of any treatment on migration is determined by ANOVA. P<0.05 is to be considered significant.

Degranulation:

Myeloperoxidase is used as a marker of degranulation. Myeloperoxidase activity in the cell supernatant obtained from the air pouch or peritoneal lavage fluid is assayed and analyzed as described above using the TMB method.

Inflammatory Mediator Concentrations:

Concentrations of the key pro-inflammatory mediators TNFα, IL-1β, IL-10, IL-6, KC, and PGE2 in air pouch and peritoneal lavage fluid are determined using commercial ELISA kits (R&D Systems) according to the manufactures instructions.

Lipid Peroxidation:

The concentration of F2-isoprostanes is a sensitive and specific measure of oxidative injury resulting from release of reactive oxygen intermediates from neutrophils and other cells {Milne G L, Musiek E S, Morrow J D. F2-isoprostanes as markers of oxidative stress in vivo: an overview. Biomarkers. 2005 November; 10 Suppl 1:S10-23}. F2-isoprostane concentration is determined in air pouch and peritoneal exudate supernatants using a commercially available ELISA (8-Isoprostane EIA, Cayman Chemical) according to the manufactures instructions.

End Point:

The experiment is considered to be successful if either local or systemic delivery of the test peptide reduces inflammation by one or more of the above measures of inhibition of release of inflammatory mediator.

The active fragment peptides of this invention inhibit neutrophil influx into and degranulation in inflamed air pouch or peritoneum, resulting in reduced MPO activity, reduced lipid peroxidation, and reduced inflammatory mediator production.

The foregoing examples are illustrative of the present invention and are not to be construed as limiting thereof. The invention is defined by the following claims, with equivalents of the claims to be included therein.

I claim:

1. A method of inhibiting the MARCKS-related release of at least one inflammatory mediator from a granule in at least one inflammatory cell in a tissue and/or fluid of a subject comprising:
   administration to said tissue and/or fluid a therapeutically effective amount of a pharmaceutical composition comprising a peptide having an amino acid sequence selected from the group consisting of: SEQ ID NOs: 106, 1, 11, 37, 45, 79, 91, 121, 143, 153, 219, 239, 248, 241, 251, 93, 108, 124, and 141, wherein
   the N-terminal amino acid of the peptide is chemically modified by acetylation; and
   wherein said peptide, optionally combined with a pharmaceutically acceptable carrier, and in a therapeutically effective inflammatory mediator release-reducing amount, reduces the amount of an inflammatory mediator released from at least one inflammatory cell as compared to release of said inflammatory mediator from at least one of the same type of inflammatory cell that would occur in the absence of said peptide.

2. The method according to claim 1, wherein said peptide consists of acetyl-peptide 106 (SEQ ID NO: 106).

3. The method according to claim 1, wherein the inflammatory mediator is released from a granule in an inflammatory cell in a tissue and/or fluid of a subject.

4. The method according to claim 1, wherein said inflammatory cell is selected from the group consisting of a leukocyte, a granulocyte, a neutrophil, a basophil, an eosinophil, a monocyte, a macrophage and a combination thereof.

5. The method according to claim 1, wherein said inflammatory mediator is selected from the group consisting of myeloperoxidase (MPO), eosinophil peroxidase (EPO), major basic protein [MBP], lysozyme, granzyme, histamine, proteoglycan, protease, a chemotactic factor, cytokine, a metabolite of arachidonic acid, defensin, bactericidal permeability-increasing protein (BPI), elastase, cathepsin G, cathepsin B, cathepsin D, beta-D-glucuronidase, alpha-mannosidase, phospholipase $A_2$, chondroitin-4-sulphate, proteinase 3, lactoferrin, collagenase, complement activator, complement receptor, N-formylmethionyl-leucyl-phenylalanine (FMLP) receptor, laminin receptor, cytochrome $b_{558}$, monocyte-chemotactic factor, histaminase, vitamin B12 binding protein, gelatinase, plasminogen activator, beta-D-glucuronidase, and a combination thereof.

6. The method according to claim 1, wherein said effective inflammatory mediator release-reducing amount of said peptide comprises a degranulation-inhibiting amount of peptide that reduces the amount of an inflammatory mediator released from at least one inflammatory cell from about 1% to about 99% as compared to the amount released from at least one inflammatory cell in the absence of the peptide.

7. The method according to claim 1, wherein said inflammatory mediator is associated with a respiratory disease or lung inflammation.

8. The method according to claim 7, wherein said respiratory disease is selected from the group consisting of asthma, chronic bronchitis, COPD and cystic fibrosis.

9. The method according to claim 1, wherein said administration is selected from the group consisting of topical administration, parenteral administration, rectal administration, pulmonary administration, nasal administration, and oral administration.

10. The method according to claim 9, wherein said pulmonary administration comprises an aerosol.

11. The method according to claim 10, wherein said aerosol is generated from a dry powder inhaler, a metered dose inhaler or nebulizer.

12. The method according to claim 1, further comprising administration to said subject of a second molecule selected from the group consisting of an antibiotic, an antiviral compound, an antiparasitic compound, an anti-inflammatory compound, and an immunomodulator.

13. The method according to claim 1, wherein said inflammatory mediator is associated with a disease selected from the group consisting of a bowel disease, a skin disease, an autoimmune disease, a pain syndrome, and combinations thereof.

14. The method according to claim 13, wherein said bowel disease is selected from the group consisting of ulcerative colitis, Crohn's disease and irritable bowel syndrome.

15. The method according to claim 13, wherein said skin disease is selected from the group consisting of rosacea, eczema, psoriasis and severe acne.

16. The method according to claim 1, wherein said inflammatory mediator is associated with arthritis.

17. The method according to claim 7, wherein said lung inflammation is associated with adult respiratory distress syndrome (ARDS), acute pulmonary inflammation, or acute thermal injury.

* * * * *